United States Patent
Yamamoto et al.

(10) Patent No.: US 10,377,759 B2
(45) Date of Patent: Aug. 13, 2019

(54) BRK INHIBITORY COMPOUND

(71) Applicant: ONO PHARMACEUTICAL CO., LTD., Osaka-shi, Osaka (JP)

(72) Inventors: Shingo Yamamoto, Osaka (JP); Hiroshi Tokura, Osaka (JP); Masakuni Kurono, Osaka (JP); Yoshinori Nomura, Osaka (JP); Shingo Hotta, Osaka (JP)

(73) Assignee: ONO PHARMACEUTICAL CO., LTD., Osaka-Shi, Osaka (JP)

( * ) Notice: Subject to any disclaimer, the term of this patent is extended or adjusted under 35 U.S.C. 154(b) by 0 days.

(21) Appl. No.: 15/738,485

(22) PCT Filed: Jun. 21, 2016

(86) PCT No.: PCT/JP2016/068429
§ 371 (c)(1),
(2) Date: Dec. 20, 2017

(87) PCT Pub. No.: WO2016/208595
PCT Pub. Date: Dec. 29, 2016

(65) Prior Publication Data
US 2018/0186800 A1    Jul. 5, 2018

(30) Foreign Application Priority Data

Jun. 22, 2015   (JP) .................. 2015-124315

(51) Int. Cl.
| | |
|---|---|
| *A01N 43/00* | (2006.01) |
| *A61K 31/00* | (2006.01) |
| *C07D 487/04* | (2006.01) |
| *A61K 39/395* | (2006.01) |
| *A61K 45/00* | (2006.01) |
| *A61K 31/519* | (2006.01) |
| *A61K 31/53* | (2006.01) |
| *A61K 45/06* | (2006.01) |
| *A61P 35/00* | (2006.01) |

(52) U.S. Cl.
CPC .......... *C07D 487/04* (2013.01); *A61K 31/519* (2013.01); *A61K 31/53* (2013.01); *A61K 39/395* (2013.01); *A61K 45/00* (2013.01); *A61K 45/06* (2013.01); *A61P 35/00* (2018.01)

(58) Field of Classification Search
None
See application file for complete search history.

(56) References Cited

U.S. PATENT DOCUMENTS

2014/0200206 A1* 7/2014 Calabrese ............ C07D 471/04
514/210.18

FOREIGN PATENT DOCUMENTS

| JP | 2009-531443 A | 9/2009 |
|---|---|---|
| JP | 2011-503103 A | 1/2011 |
| JP | 2011-518219 A | 6/2011 |
| WO | WO-2007/126841 A2 | 11/2007 |
| WO | WO-2009/062118 A2 | 5/2009 |
| WO | WO-2009/131687 A2 | 10/2009 |

OTHER PUBLICATIONS

Harvey A et al. (2011), "Chapter 20: Future Therapeutic Strategies: Implications for Brk Targeting", Breast Cancer—Current and Alternative Therapeutic Modalities, pp. 413-434.
Brauer P M et al. (2010), "Building a better understanding of the intracellular tyrosine kinase PTK6—BRK by BRK", Biochim Biophys Acta., 1806(1): 66-73.
Brauer P M et al. (2009), "RAKing in AKT: A Tumor Suppressor Function for the Intracellular Tyrosine Kinase FRK", Cell Cycle, 8(17): 2728-2732.
Regan Anderson TM et al. (2013), "Breast Tumor Kinase (Brk/PTK6) is a Mediator of Hypoxia-Associated Breast Cancer Progression", Cancer Research, 73(18), pp. 5810-5820.
Zheng Y et al. (2013), "PTK6 Activation at the Membrane Regulates Epithelial-Mesenchymal Transition in Prostate Cancer", Cancer Research, 73(17), pp. 5426-5437.
Zhao C et al. (2013), "Expression of protein tyrosine kinase 6 (PTK6) in nonsmall cell lung cancer and their clinical and prognostic significance", OncoTargets and Therapy, vol. 6, pp. 183-188.

(Continued)

*Primary Examiner* — Jared Barsky
(74) *Attorney, Agent, or Firm* — Foley & Lardner LLP

(57) ABSTRACT

The present invention relates to a compound represented by general formula (I) (wherein, all symbols represent the same meanings as the symbols set forth in the specification), a salt thereof, a solvate thereof, an N-oxide thereof, or a prodrug of any of these. Since the compound has a Brk inhibitory activity, the compound is useful as a drug ingredient for the prevention and/or treatment of Brk-related diseases such as cancer, for example.

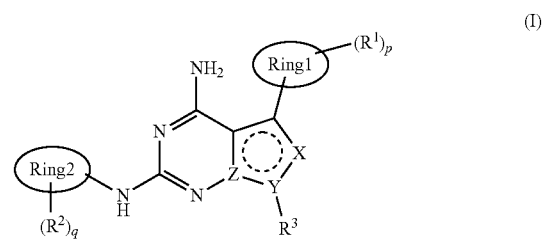

3 Claims, No Drawings

(56) References Cited

OTHER PUBLICATIONS

Liu X et al. (2013), "Low expression of PTK6/Brk predicts poor prognosis in patients with laryngeal squamous cell carcinoma", Journal of Translational Medicine, 11:59.
International Search Report for PCT/JP2016/068429 dated Jun. 21, 2016.
Extended European Search Report dated Nov. 13, 2018 in corresponding application No. 16814365.9.
Zeng et al, Discovery of novel imidazo [1,2-a] pyrazine-8-amines as Brk/PTK6 inhibitors, Bioorganic & Medicinal Chemistry Letters, 2011, pp. 5870-5875.

* cited by examiner

BRK INHIBITORY COMPOUND

CROSS-REFERENCE TO RELATED APPLICATIONS

The present application is a U.S. National Phase of International Patent Application No. PCT/JP2016/068429, filed Jun. 21, 2016, which claims priority to Japanese Patent Application No. 2015-124315, filed Jun. 22, 2015, the entireties of which are incorporated herein by reference.

TECHNICAL FIELD

The present invention relates to a Brk inhibitory compound represented by the following general formula (I):

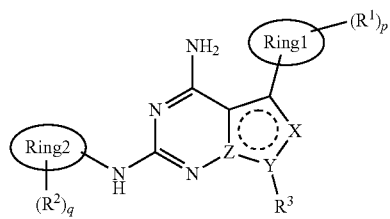

(wherein, all the symbols have the same meanings as described below), a salt thereof, a solvate thereof an N-oxide thereof, or a prodrug of any of these (hereinafter, referred to as the compound of the present invention), and a medicament comprising the same as an active ingredient.

BACKGROUND ART

Brk (Breast tumor kinase) is also referred to as PTK6 (protein tyrosine kinase 6), and is a non-receptor tyrosine kinase which belongs to FRK (Fyn-related kinase)/PTK6 family kinases which are tyrosine kinases. Brk is coded by 451 amino acids. Brk was identified from human normal melanocytes in the first place, and immediately after that, Brk was identified in breast cancer. Brk is highly expressed in a lot of tumors including breast cancer, ovarian cancer, colon cancer, pancreatic cancer, bladder cancer, esophageal cancer, gastric cancer, non-small-cell lung cancer, prostate cancer, oral squamous cell cancer, head and neck squamous cell cancer, melanoma, B-cell lymphoma, and T-cell lymphoma. In particular, Brk is a poor prognostic factor in breast cancer, prostate cancer, nasopharyngeal cancer, and non-small-cell lung cancer. In addition, it is thought that Brk plays important roles in tumorigenesis such as promotion of proliferation, migration, and invasion of cancer cells, and avoidance of cell death (see Non Patent Literatures 1 to 7).

Accordingly, it is thought that a compound which inhibits activation of Brk is useful for treating various types of cancer.

On the other hand, it has been described in Patent Literature 1 that, a compound of the following general formula (A) or a pharmaceutically acceptable salt or a derivative thereof is used for treatment or amelioration of one or more symptoms of α-synuclein toxicity, ca-synuclein mediated diseases, or diseases in which α-synuclein fibrils are a symptom or cause of the disease.

The general formula (A) is as follows:

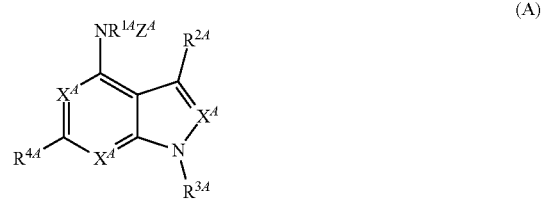

(wherein:
each $X^A$ is independently N or CH;
$R^{1\ A}$ and $Z^A$ are each independently $R^{5\ A}$, $C(O)R^{5\ A}$ or the like;
$R^{2\ A}$ and $R^{3\ A}$ are each independently H, halo, $R^{5\ A}$, $OR^{5\ A}$, $OC(O)R^{5\ A}$ or the like;
$R^{4\ A}$ is independently H, halo, $NR^{5\ A}R^{5\ A}$, $NR^{5\ A}R^{6\ A}$ or the like; or optionally substituted alkyl, aryl, aralkyl, heteroaryl, or heteroaralkyl; and each of $R^{5\ A}$ and $R^{6\ A}$ is independently H, or optionally substituted alkyl, alkenyl, alkynyl, cycloalkyl, cycloalkenyl, aryl, heteroaryl, or heterocyclyl (the definition of groups is partly extracted)).

In addition, it has been described in Patent Literature 2 a method of treating a subject for a disorder characterized by impaired protein trafficking, comprising administering to the subject an effective amount of a compound represented by general formula (B) or a pharmaceutically acceptable salt thereof, wherein the disorder is not a synucleinopathy.

The general formula (B) is as follows:

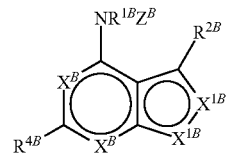

(wherein:
each $X^B$ is independently N, CH or $C(C_1$-$C_4$ alkyl);
each $X^{1\ B}$ is independently N, $NR^{3\ B}$, CH or $C(C_1$-$C_4$ alkyl);
$R^{1\ B}$ and $Z^B$ are each independently $R^{5\ B}$, $C(O)R^{5\ B}$ or the like; or, $NR^{1\ B}\ Z^B$, taken together, is N=CH—$NR^{5\ B}R^{5\ B}$;
$R^{2\ B}$ and $R^{3\ B}$ are each independently H, halo, $R^{5\ B}$ or the like;
$R^{4\ B}$ is independently H, halo, $NR^{5\ B}R^{5\ B}$, $NR^{5\ B}R^{6\ B}$ or the like;
or optionally substituted alkyl, aryl, aralkyl, heteroaryl or heteroaralkyl;
and each of $R^{5\ B}$ and $R^{6\ B}$ is independently H, or optionally substituted alkyl, alkenyl, alkynyl, cycloalkyl, cycloalkenyl, aryl, heteroaryl or heterocyclyl (the definition of groups is partly extracted)).

Further, it has been described in Patent Literature 3 that a compound of the following formula (C) or a tautomer or pharmaceutically acceptable salt thereof is used for treating Syk and/or JAK related diseases such as cardiac disease, inflammatory disease, immune-related disease, and cell proliferative disorder.

The general formula (C) is as follows:
a compound having:

$$\text{(C)}$$

([wherein,
$Y^{1\,a\,C}$ is selected from the group consisting of N, CH and C;
$Z^{1\,a\,C}$ is selected from the group consisting of a bond, $-SO_2-$, $-CO-$, and the like;
$R^{1\,a\,C}$ is selected from the group consisting of: (a) H, (b) $C_{1-8}$ alkyl that may be substituted with 1 to 3 substituents selected from the group consisting of amino, hydroxy, $C_{1-8}$ alkoxy and the like, (c) $C_{3-8}$ cycloalkyl that may be substituted with 1 to 3 amino substituents, (d) aryl that may be substituted with 1 to 3 substituents selected from the group consisting of $C_{1-8}$ alkyl, $C_{1-8}$ alkoxy, $C_{1-8}$ alkylamino and the like, (e) heterocyclyl, halogen, cyano that may be substituted with 1 to 3 substituents selected from the group consisting of: $C_{1-8}$ alkyl, oxo and the like, cyano $C_{1-6}$ alkylcarbonyl, aminocarbonyl and the like, and (f) heteroaryl that may be substituted with 1 to 3 substituents selected from the group consisting of $C_{1-8}$ alkyl, $C_{1-8}$ alkylsulfonyl and the like;
$R^{2\,a\,C}$ is H or $C_{1-8}$ alkyl or the like;
$R^{3\,a\,C}$ is H or $C_{1-8}$ alkyl or the like;
$R^{4\,a\,C}$ is selected from the group consisting of: (a) aryl that may be substituted with 1 to 3 substituents $R^{4\,c\,C}$, each of which is independently selected from the group consisting of: $C_{1-8}$ alkoxy, amino, $C_{1-8}$ alkylcarbonyl and aminocarbonyl $C_{1-8}$ alkoxy, (b) heteroaryl, heterobicyclic $C_{1-8}$ alkyl, halo, hydroxyl that may be substituted with 1 to 3 substituents $R^{4\,c\,C}$, each of which is independently selected from the group consisting of: $C_{1-8}$ alkyl, halogen, hydroxyl, oxo $C_{1-8}$ alkoxy and =S, (c) heterocyclyl that may be substituted with 1 to 3 substituents $R^{4\,c\,C}$, each of which is independently selected from the group consisting of: $C_{1-8}$ alkyl and oxo;
$R^{4\,b\,C}$ is selected from the group consisting of: H, $C_{1-8}$ alkyl, $C_{1-8}$ alkylcarbonyl, $C_{1-8}$ alkylcarbonylamino, $C_{1-8}$ alkylsulfonyl, $C_{1-8}$ alkylsulfinyl, $C_{1-8}$ alkylthio, $C_{1-8}$ alkoxy, $C_{1-8}$ alkoxycarbonylamino, $C_{1-8}$ alkoxycarbonyl, amino, aminocarbonyl, aminosulfonyl, aminocarbonyl $C_{1-8}$ alkoxy, amino $C_{1-8}$ alkylene, carboxy, $C_{3-8}$ cycloalkylcarbonylamino, $C_{3-8}$ cycloalkylcarbonyl, halo, hydroxy and heterocyclyl;
when $R^{4\,b\,C}$ is heterocyclyl, it may be substituted with 1 to 3 substituents $R^{4\,d\,C}$ independently selected from the group consisting of: $C_{1-8}$ alkyl, $C_{1-8}$ alkoxy, hydroxy, amino, halo, cyano, oxo and the like;
$R^{5\,a\,C}$ is selected from the group consisting of H, $C_{1-8}$ alkyl and the like;
$R^{6\,a\,C}$ is selected from the group consisting of H, $C_{1-8}$ alkyl and the like;
$R^{7\,a\,C}$ is selected from the group consisting of H, $C_{1-8}$ alkyl, $C_{3-8}$ cycloalkyl, and aryl and the like, each of aryl and heteroaryl may be substituted with halo, $C_{1-8}$ alkyl, $C_{1-8}$ alkoxy, cyano, amino, hydroxyl, heteroaryl; and the dashed line indicates a double bond or a single bond] or a tautomer or a pharmaceutically acceptable salt thereof (the definition of groups is partly extracted)).

However, none of the Patent Literatures describe or suggest a compound which is selective for Brk.

CITATIONS LISTS

Patent Literatures

Patent Literature 1: WO 2007/126841 A
Patent Literature 2: WO 2009/062118 A
Patent Literature 3: WO 2009/131687 A Non Patent Literatures Non Patent Literature 1: Breast Cancer-Current and Alternative Therapeutic Modalities, pages 413-434, 2011
Non Patent Literature 2: Biochimica et Biophysica Acta, Vol. 1806, pages 66-73, 2010
Non Patent Literature 3: Cell Cycle, Vol. 8, pages 2728-2732, 2009
Non Patent Literature 4: Cancer Research, Vol. 73, pages 5810-5820, 2013
Non Patent Literature 5: Cancer Research, Vol. 73, pages 5426-5437, 2013
Non Patent Literature 6: OncoTargets and Therapy, Vol. 6, pages 183-188, 2013
Non Patent Literature 7: Journal of Translational Medicine, Vol. 11, 59, 2013

SUMMARY OF INVENTION

Technical Problems

An object of the present invention is to find out a compound useful as a preventive and/or therapeutic agent for various cancer diseases by creating a compound having an inhibitory activity on Brk.

Solutions to Problems

The present inventors have carried out intensive studies to find a compound having an inhibitory activity on Brk in order to achieve the above-described object. As a result, the present inventors have found that a compound represented by general formula (I) described below has Brk inhibitory action and high Brk selectivity as compared with other kinases, and have completed the present invention.

In other words, the present invention relates to the followings:

[1] A compound represented by general formula (I):

$$\text{(I)}$$

(wherein:

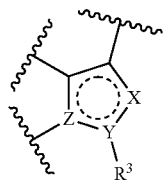

represents

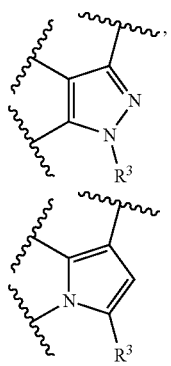

Ring 1 represents a 3- to 15-membered ring;
$R^1$ represents a halogen, an oxo group, a hydroxyl group, a cyano group, $NR^4R^5$, a C1-4 alkyl group, or a C1-4 alkoxy group, said C1-4 alkyl group or C1-4 alkoxy group may be substituted with a halogen;
$R^4$ and $R^5$ each independently represent a hydrogen atom, a C1-4 alkyl group, or a C1-4 acyl group;
p represents an integer of 0 to 7;
$R^3$ represents a C1-4 alkyl group, a C2-4 alkenyl group, a C2-4 alkynyl group, a (C3-6 cycloalkyl)-$(CH_2)_r$— group, or a (3- to 6-membered saturated heterocycle)-$(CH_2)_s$— group, said $R^3$ may be substituted with a halogen;
r represents an integer of 0 to 4;
s represents an integer of 0 to 4;
Ring 2 represents a 3- to 15-membered ring;
$R^2$ represents a halogen, an oxo group, a hydroxyl group, a cyano group, $C(O)R^6$, $SO_2R^7$, a C1-4 alkyl group, or a C1-4 alkoxy group,
said C1-4 alkyl group or C1-4 alkoxy group may be substituted with a substituent selected from the group consisting of a halogen, a hydroxyl group, a cyano group, $C(O)R^8$, $NR^9R^{10}$, and $SO_2R^{11}$;
$R^6$ represents a hydroxyl group, a C1-4 alkyl group, a C1-4 alkoxy group, or $NR^{12}R^{13}$;
$R^7$ and $R^{11}$ each independently represent a hydroxyl group, a C1-4 alkyl group, or a C3-6 cycloalkyl group, said C1-4 alkyl group may be substituted with a halogen or $CO_2R^{14}$;
$R^8$ represents a hydroxyl group, a C1-4 alkoxy group, or $NR^{15}R^{16}$;
$R^9$, $R^{10}$, $R^{12}$, and $R^{13}$ each independently represent a hydrogen atom, a C1-4 acyl group, or a C1-4 alkyl group that may be substituted with $NR^{15}R^{16}$;
$R^9$ and $R^{10}$, as well as $R^{12}$ and $R^{13}$, taken together with the nitrogen atom to which they are attached, may form a 5- to 6-membered saturated cyclic amine;
$R^{14}$ represents a hydrogen atom or a C1-4 alkyl group;
$R^{15}$ or $R^{16}$ each independently represents a hydrogen atom, a C1-4 alkyl, or a C1-4 acyl group;
$R^{15}$ and $R^{16}$, taken together with the nitrogen atom to which they are attached, may form a 5- to 6-membered saturated cyclic amine;
q represents an integer of 0 to 7;
provided that when p and q each represent an integer of 2 or more, $R^1$ and $R^2$ each independently may be the same or different);
a salt thereof, a solvate thereof, an N-oxide thereof, or a prodrug of any of these;

[2] The compound according to the above item [1], wherein q is 2 or 3;

[3] The compound according to the above item [1] or [2], wherein:

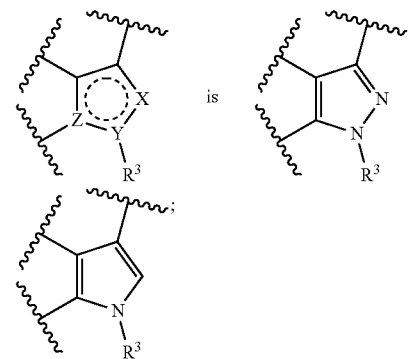

[4] The compound according to any one of the above items [1] to [3], which is represented by general formula (I-1):

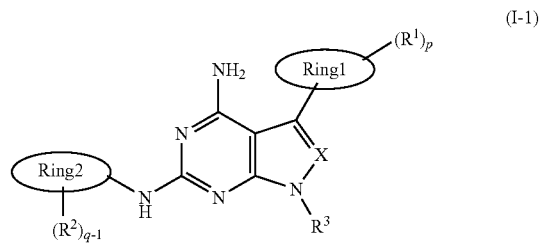

(wherein:
X represents CH or N;
q-1 represents 2 or 3;
all the other symbols represent the same meanings as symbols set forth in the above item [1]);

[5] The compound according to any one of the above items [1] to [4], wherein X is N;

[6] The compound according to any one of the above items [1] to [5], wherein Ring 1 is a 5- to 6-membered monocyclic aromatic ring or a 9- to 10-membered bicyclic aromatic ring that may be partially saturated;

[7] The compound according to any one of the above items [1] to [6], wherein Ring 2 is a 5- to 6-membered monocyclic aromatic ring or a 9- to 10-membered bicyclic aromatic ring that may be partially saturated;

[8] The compound according to the above item [1], wherein q is an integer of 1 or more;

[9] The compound according to the above item [1] or [8], which is represented by general formula (I-a):

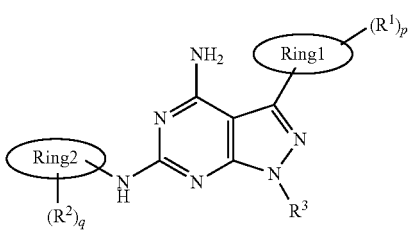

(wherein, all symbols represent the same meanings as symbols set forth in the above item [1]);

[10] The compound according to the above item [1] or [8], which is represented by general formula (I-b):

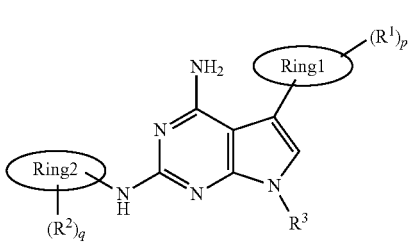

(wherein, all symbols represent the same meanings as symbols set forth in the above item [1]);

[11] The compound according to any one of the above items [1], [8], and [10], wherein $R^3$ is a C3-4 branched alkyl group that may be substituted with a halogen;

[12] The compound according to any one of the above items [1], [8], [10], and [11], wherein Ring 2 is a benzene ring, and when q represents an integer of 1 or more, at least one $R^2$ is a halogen;

[13] The compound according to any one of the above items [1], [8], [10], and [11], wherein Ring 2 is a 5- to 6-membered monocyclic aromatic heterocycle;

[14] The compound according to the above item [1], which is represented by general formula (I-c):

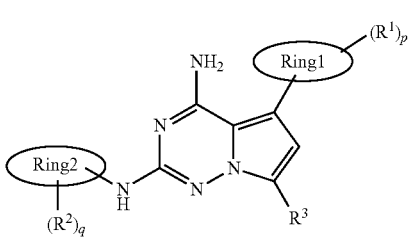

(wherein, all symbols represent the same meanings as symbols set forth in the above item [1]);

[15] A compound, which is:
(1) $N^6$-(1,3-dimethyl-1H-pyrazol-4-yl)-3-(1H-indol-5-yl)-1-isopropyl-1H-pyrazolo[3,4-d]pyrimidine-4,6-diamine;
(2) $N^6$-(1,3-dimethyl-1H-pyrazol-4-yl)-3-(7-fluoro-1H-indazol-4-yl)-1-isopropyl-1H-pyrazolo[3,4-d]pyrimidine-4,6-diamine;
(3) 3-(7-chloro-1H-indazol-4-yl)-$N^6$-[2-fluoro-4-(methylsulfonyl)phenyl]-1-isopropyl-1H-pyrazolo[3,4-d]pyrimidine-4,6-diamine;
(4) $N^6$-[2-fluoro-4-(methylsulfonyl)phenyl]-3-(1H-indazol-4-yl)-1-isopropyl-1H-pyrazolo[3,4-d]pyrimidine-4,6-diamine;
(5) 3-(7-fluoro-1H-indazol-4-yl)-$N^6$-[2-fluoro-4-(methylsulfonyl)phenyl]-1-isopropyl-1H-pyrazolo[3,4-d]pyrimidine-4,6-diamine; or
(6) 4-(4-amino-2-{[2-fluoro-4-(methylsulfonyl)phenyl]amino}-7-isopropyl-7H-pyrrolo[2,3-d]pyrimidin-5-yl)-1H-indazole-7-carbonitrile;

[16] A compound, which is:
(1) $N^6$-(1,3-dimethyl-1H-pyrazol-4-yl)-3-(1H-indol-5-yl)-1-isopropyl-1H-pyrazolo[3,4-d]pyrimidine-4,6-diamine;
(2) $N^6$-(1,3-dimethyl-1H-pyrazol-4-yl)-3-(7-fluoro-1H-indazol-4-yl)-1-isopropyl-1H-pyrazolo[3,4-d]pyrimidine-4,6-diamine;
(3) 3-(7-chloro-1H-indazol-4-yl)-$N^6$-[2-fluoro-4-(methylsulfonyl)phenyl]-1-isopropyl-1H-pyrazolo[3,4-d]pyrimidine-4,6-diamine;
(4) $N^6$-[2-fluoro-4-(methylsulfonyl)phenyl]-3-(1H-indazol-4-yl)-1-isopropyl-1H-pyrazolo[3,4-d]pyrimidine-4,6-diamine;
(5) 3-(7-fluoro-1H-indazol-4-yl)-$N^6$-[2-fluoro-4-(methylsulfonyl)phenyl]-1-isopropyl-1H-pyrazolo[3,4-d]pyrimidine-4,6-diamine; or
(6) 4-(4-amino-2-{[2-fluoro-4-(methylsulfonyl)phenyl]amino}-7-isopropyl-7H-pyrrolo[2,3-d]pyrimidin-5-yl)-1H-indazole-7-carbonitrile;
a salt thereof, a solvate thereof, an N-oxide thereof, or a prodrug of any of these;

[17] A pharmaceutical composition comprising the compound represented by general formula (I) according to the above item [1], a salt thereof, a solvate thereof, an N-oxide thereof, or a prodrug of any of these as an active ingredient;

[18] The composition according to the above item [17], which is a Brk inhibitor;

[19] The composition according to the above item [18], which is an agent for preventing and/or treating cancer.

[20] The composition according to the above item [19], wherein the cancer is breast cancer, ovarian cancer, large bowel cancer, lung cancer, prostate cancer, head and neck cancer, melanoma, pancreatic cancer, bladder cancer, esophageal cancer, gastric cancer, or lymphoma;

[21] The composition according to the above item [19], wherein the cancer is breast cancer, ovarian cancer, large bowel cancer, lung cancer, prostate cancer, head and neck cancer, lymphoma, brain tumor, glioma, pituitary adenoma, uveal malignant melanoma, meningioma, thymoma, mesothelioma, esophageal cancer, gastric cancer, duodenal cancer, hepatocellular cancer, bile duct cancer, gallbladder cancer, pancreatic cancer, renal cell cancer, renal pelvis-ureteral cancer, bladder cancer, penile cancer, testicular cancer, uterine cancer, vaginal cancer, vulvar cancer, skin cancer, malignant bone tumor, soft tissue sarcoma, chondrosarcoma, leukemia, myelodysplastic syndrome, and multiple myeloma.

[22] A medicament comprising the compound represented by general formula (I) according to the above item [1], a salt thereof, a solvate thereof, an N-oxide thereof, or a prodrug of any of these in combination with at least one kind selected from an alkylating agent, an antimetabolite, an anticancer antibiotic, a plant-derived preparation, a hormone preparation, a platinum compound, a topoisomerase inhibitor, a kinase inhibitor, an immune checkpoint inhibitor, an anti-CD20 antibody, an anti-HER2 antibody, an anti-EGFR antibody, and an anti-VEGF antibody;

[23] A method for preventing and/or treating cancer comprising administering an effective amount of the compound represented by general formula (I) according to the above item [1], a salt thereof, a solvate thereof, an N-oxide thereof, or a prodrug of any of these to a patient in need of the prevention and/or treatment of cancer,

[24] A method for preventing and/or treating cancer comprising administering an effective amount of the compound represented by general formula (I) according to the above item [1], a salt thereof, a solvate thereof, an N-oxide thereof, or a prodrug of any of these to a patient in need of the prevention and/or treatment of cancer, in combination with at least one kind selected from radiation therapy, chimeric antigen receptor T cell therapy (CAR-T), thermotherapy, NK cell therapy, or NKT cell therapy;

[25] A method for inhibiting Brk comprising administering an effective amount of the compound represented by general formula (I) according to the above item [1], a salt thereof, a solvate thereof, an N-oxide thereof, or a prodrug of any of these to a patient in need of the inhibition of Brk;

[26] The compound represented by general formula (I) according to the above item [1], a salt thereof, a solvate thereof, an N-oxide thereof, or a prodrug of any of these for preventing and/or treating cancer; and

[27] Use of the compound represented by general formula (I) according to the above item [1], a salt thereof, a solvate thereof, an N-oxide thereof, or a prodrug of any of these for the manufacture of an agent for preventing and/or treating cancer.

Advantageous Effects of Invention

The compound of the present invention has a Brk inhibitory activity and high Brk selectivity as compared with other kinases, and therefore, is a preventive/therapeutic agent with excellent safety for diseases in which Brk involves, for example, cancer.

DESCRIPTION OF EMBODIMENTS

The present invention is described in details hereinbelow.

In the description in translation of the present specification and claims into a language such as English, unless otherwise defined, a term in a singular form encompasses that in a plural form, and a term in a plural form encompasses that in a singular form.

In the present specification, a "3- to 15-membered ring" refers to a "3- to 15-membered carbocycle" and a "3- to 15-membered heterocycle".

In the present specification, a "3- to 15-membered carbocycle" refers to, for example, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene, heptalene, perhydroheptalene, biphenylene, as-indacene, s-indacene, acenaphthylene, acenaphthene, fluorene, phenalene, phenanthrene, anthracene, spiro[4.4]nonane, spiro[4.5]decane, spiro[5.5]undecane, bicyclo[2.2.1]heptane, bicyclo[22.1]hept-2-ene, bicyclo[3.1.1]heptane, bicyclo[3.1.1]hept-2-ene, bicyclo[2.2.2]octane, bicyclo[2.2.2]oct-2-ene, bicyclo[4.2.0]octa-1,3,5-triene, 2,3-dihydro-1H-indene, 1,2,3,4-tetrahydronaphthalene, 6,7,8,9-tetrahydro-5H-benzo[7]annulene, 5,6,7,8,9,10-hexahydrobenzo[8]annulene, 2',3'-dihydrospirocyclopropane-1,1'-indene, 3',4'-dihydro-2'H-spirocyclopropane-1,1'-naphthalene, adamantane, noradamantane, cubane rings and the like.

In the present specification, a "3- to 15-membered heterocycle" refers to, for example, pyrrole, imidazole, triazole, tetrazole, pyrazole, pyridine, pyrazine, pyrimidine, pyridazine, azepine, diazepine, furan, pyran, oxepin, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepin, benzoxazepine, benzoxadiazepine, benzothiepine, benzothiazepine, benzothiadiazepine, benzazepine, benzodiazepine, benzofurazan, benzothiadiazole, benzotriazole, carbazole, β-carboline, acridine, phenazine, dibenzofuran, xanthene, dibenzothiophene, phenothiazine, phenoxazine, phenoxathiin, thianthrene, phenanthridine, phenanthroline, perimidine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepin, tetrahydrooxepin, perhydrooxepin, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroiobenzothiophcne, perhydroisobenzothiophene, dihydroindazole, perhydroindazole, dihydroquinoline, tetrahydroqunoline, perhydroqunoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoine, dihydrocinoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindane, benzodioxane, chromane, benzodithiolane, benzodithiane, azaspiro[4.4]nonane, oxazaspiro[4.4]nonane, dioxaspiro[4.4]nonane, azaspiro[4.5]decane, thiaspiro[4.5]decane, dithiaspiro[4.5]decane, dioxaspiro[4.5]decane, oxazaspiro[4.5]decane, azaspiro[5.5]undecane, oxaspiro[5.5]undecane, dioxaspiro[5.5]undecane, azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane, and diazabicyclo[2.2.2]octane rings and the like.

In the present specification, a "halogen" refers to fluorine, chlorine, bromine, and iodine.

In the present specification, a "C1-4 alkyl group" refers to, for example, methyl, ethyl, n-propyl, isopropyl, n-butyl, sec-butyl, tert-butyl, and isobutyl groups.

In the present specification, a "C2-4 alkenyl group" refers to, for example, vinyl, 1-propenyl, 2-propenyl, 1-butenyl, 2-butenyl, 3-butenyl groups and the like.

In the present specification, a "C2-4 alkynyl group" refers to, for example, ethinyl, 1-propynyl, 2-propynyl, 1-butynyl, 2-butynyl, 3-butynyl groups and the like.

In the present specification, a "C3-6 cycloalkyl group" refers to cyclopropyl, cyclobutyl, cyclopentyl, and cyclohexyl groups.

In the present specification, a "C1-4 alkoxy group" refers to methoxy, ethoxy, n-propoxy, isopropoxy, n-butoxy, sec-butoxy, tert-butoxy, and isobutoxy groups.

In the present specification, a "C1-4 acyl group" refers to methanoyl, ethanoyl, propanoyl, butanoyl groups, and isomers thereof.

In the present specification, a "C3-4 branched alkyl group" refers to isopropyl, sec-butyl, tert-butyl, and isobutyl groups.

In the present specification, a "3- to 6-membered saturated heterocycle" refers to, for example, aziridine, azetidine, pyrrolidine, piperidine, oxirane, oxetane, oxolane (tetrahydrofuran), oxane (tetrahydropyran), thiirane, thietane, thiolane (tetrahydrothiophene), thiane (tetrahydrothiopyran), pyrazolidine, imidazolidine, dioxolane, dithiolane, oxazolidine, isoxazolidine, thiazolidine, isothiazolidine, hexahydropyridazine, piperazine, dioxane, dithiane, morpholine, thiomorpholine rings and the like.

In the present specification, a "5- to 6-membered monocyclic aromatic ring" refers to, for example, pyrrole, furan, thiophene, imidazole, pyrazole, oxazole, isoxazole, thiazole, isothiazole, triazole, oxadiazole, thiadiazole, furazan, tetrazole, benzene, pyridine, pyridazine, pyrimidine, pyrazine, triazine, tetrazine rings and the like.

In the present specification, a "5- to 6-membered monocyclic aromatic heterocycle" refers to, for example, pyrrole, imidazole, triazole, tetrazole, pyrazole, furan, thiophene, oxazole, isoxazole, thiazole, isothiazole, furazan, oxadiazole, thiadiazole, pyridine, pyrazine, pyrimidine, pyridazine rings and the like.

In the present specification, a "9- to 10-membered bicyclic aromatic ring" refers to, for example, naphthalene, benzofuran, isobenzofuran, benzothiophene, isobenzothiophene, indole, isoindole, indolizine, benzoxazole, benzisoxazole, benzothiazole, benzisothiazole, indazole, benzimidazole, benzofurazan, benzothiadiazole, benzotriazole, purine, quinoline, isoquinoline, phthalazine, pteridine, naphthyridine, quinoxaline, quinazoline, cinnoline, chromene, pyrrolopyridine, pyrazolopyridine, pyrrolopyrimidine, pyrazolopyrimidine, pyridopyrimidine, triazolopyridine, triazolopyrimidine, pyrazolotriazine rings and the like.

In the present specification, a "9- to 10-membered bicyclic aromatic ring that may be partially saturated" refers to, for example, naphthalene, benzofuran, isobenzofuran, benzothiophene, isobenzothiophene, indole, isoindole, indolizine, benzoxazole, benzisoxazole, benzothiazole, benzisothiazole, indazole, benzimidazole, benzofurazan, benzothiadiazole, benzotriazole, purine, quinoline, isoquinoline, phthalazine, pteridine, naphthyridine, quinoxaline, quinazoline, cinnoline, chromene, pyrrolopyridine, pyrazolopyridine, pyrrolopyrimidine, pyrazolopyrimidine, pyridopyrimidine, triazolopyridine, triazolopyrimidine, pyrazolotriazine, indane, 2,3-dihydrobenzofuran, 2,3-dihydrobenzothiophene, indoline, 2,3-dihydro-1H-indazole rings and the like.

In the present specification, a "9- to 10-membered aromatic heterocycle" refers to, for example, indole, isoindole, indazole, purine, benzimidazole, benzotriazole, quinoline, isoquinoline, phthalazine, pteridine, naphthyridine, quinoxaline, quinazoline, cinnoline rings and the like.

In the present specification, a "5- to 6-membered saturated cyclic amine" refers to, for example, pyrrolidine, imidazolidine, triazolidine, tetrazolidine, piperidine, pyrazolidine, perhydropyrimidine, piperazine, perhydropyridazine, tetrahydrooxazole (oxazolidine), tetrahydroisoxazole (isoxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, tetrahydrothiadiazole (thiadiazolidine), tetrahydrothiazine, tetrahydrothiadiazine, morpholine, thiomorpholine rings and the like.

In the present specification,

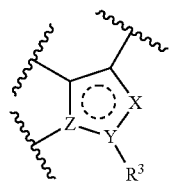

is preferably,

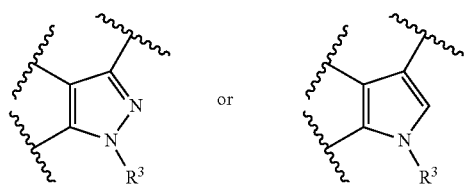

and is more preferably,

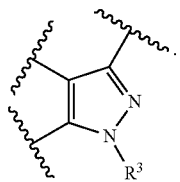

In the present specification, Ring 1 is preferably a 5- to 6-membered monocyclic aromatic ring or a 9- to 10-membered bicyclic aromatic ring that may be partially saturated, is more preferably an imidazole, pyrazole, oxazole, isoxazole, thiazole, isothiazole, benzene, pyridine, pyridazine, pyrimidine, pyrazine, benzofuran, benzothiophene, indole, isoindole, benzoxazole, benzothiazole, indazole, benzimidazole, quinoline, isoquinoline, phthalazine, naphthyridine, quinoxaline, quinazoline, pyrrolopyridine, pyrazolopyridine, pyrrolopyrimidine, pyrazolopyrimidine, 2,3-dihydrobenzofuran, or pyridopyrimidine ring, is furthermore preferably a benzene, pyridine, benzofuran, indole, indazole, benzothiazole, quinoline, isoquinoline, 2,3-dihydrobenzofuran or pyrrolopyridine ring, is especially preferably a 9- to 10-membered aromatic heterocycle where heteroatoms contained therein are only nitrogen, and is the most preferably an indole or indazole ring.

In the present specification, Ring 2 is preferably a 5- to 6-membered monocyclic aromatic ring or a 9- to 10-membered bicyclic aromatic ring that may be partially saturated, is more preferably an imidazole, pyrazole, oxazole, isoxazole, thiazole, isothiazole, benzene, pyridine, pyridazine, pyrimidine, pyrazine, benzofuran, benzothiophene, indole, indolizine, benzoxazole, benzothiazole, indazole, benzimidazole, benzofurazan, quinoline, isoquinoline, phthalazine, naphthyridine, quinoxaline, indane, indoline or quinazoline ring, is furthermore preferably a pyrazole, thiazole, benzene, pyridine, indane, indoline or pyrimidine ring, is especially preferably a benzene or a 5- to 6-membered monocyclic aromatic heterocycle, and is the most preferably a benzene or pyrazole ring.

In the present specification, a benzene ring of Ring 2 is preferably a benzene ring where in the case where q is an integer of 1 or more, at least one $R^2$ is a halogen, and is more preferably a benzene ring where in the case where q is an integer of 2 or more, $R^2$ is at least one halogen and $SO_2 R^7$.

In the present specification, $R^1$ is preferably a halogen, oxo, hydroxy, cyano, amino, methyl, ethyl, isopropyl, difluoromethyl, trifluoromethyl, methoxy, ethoxy, isopropoxy, difluoromethoxy, or trifluoromethoxy group, is more preferably a halogen, oxo, hydroxy, cyano, amino, methyl, trifluoromethyl, methoxy, difluoromethoxy, or trifluoromethoxy group, and is the most preferably a halogen or cyano group.

In the present specification, p is preferably an integer of 0 to 4, and is more preferably 0 or 1.

In the present specification, $R^3$ is preferably a methyl, ethyl, isopropyl, tert-butyl, difluoromethyl, trifluoromethyl, 2,2,2-trifluoroethyl, cyclopropyl, cyclopropylmethyl, cyclobutyl, cyclobutylmethyl, cyclopentyl, cyclopentylmethyl, cyclohexyl, cyclohexylmethyl, oxetanyl, oxetanylmethyl, oxolanyl, or oxolanylmethyl group, is more preferably a difluoromethyl, isopropyl, tert-butyl, 2,2,2-trifluoroethyl, cyclobutyl, cyclopentyl, or oxetanyl group, is furthermore preferably a C3-4 branched alkyl group that may be substituted with a halogen, and is especially preferably an isopropyl group.

In the present specification, a C3-6 cycloalkyl in $R^3$ group is preferably a cyclobutyl or cyclopentyl group.

In the present specification, a 3- to 6-membered saturated heterocycle in $R^3$ group is preferably an aziridine, azetidine, pyrrolidine, piperidine, oxirane, oxetane, oxolane (tetrahydrofuran), oxane (tetrahydropyran), thiirane, thietane, thiolane (tetrahydrothiophene), or thiane (tetrahydrothiopyran) ring, is more preferably an aziridine, azetidine, pyrrolidine, oxirane, oxetane, or oxolane (tetrahydrofuran) ring, and is especially preferably an oxetane ring.

In the present specification, r is preferably 0 or 1, and is more preferably 0.

In the present specification, s is preferably 0 or 1, and is more preferably 0.

In the present specification, $R^2$ is preferably a halogen, oxo, $C(O)R^6$, $SO_2 R^7$, a C1-4 alkyl or a C1-4 alkoxy group, the C1-4 alkyl or the C1-4 alkoxy group may be substituted with a substituent selected from the group consisting of a halogen, a hydroxyl group, a cyano group, $C(O)R^8$, $NR^9R^{10}$ and $SO_2 R^{11}$, is more preferably a halogen, oxo, acetyl, methylaminocarbonyl, dimethylaminocarbonyl, dimethylaminoethoxy, 4-morpholinylmethyl, dimethylaminocarbonylmethyl, 4-morpholinylcarbonylmethyl, piperidine-1-carbonyl, 2-(dimethylamino)ethylcarbamoyl, carboxy, carboxymethyl, 2-carboxypropan-2-yl, methyl, difluoromethyl, cyanomethyl, dimethylaminoethyl, morpholine-4-carbonyl, 2-hydroxy-2-methylpropyl, 1,3-dihydroxy-2-methylpropan-2-yl, methoxy, 2-amino-2-oxoethyl, 2-methoxy-2-oxoethyl, methylsulfonyl, methylsulfonylmethyl, cyclopropylsulfonyl, carboxymethylsulfonyl, or 3-(carboxymethyl)sulfonyl group, and is especially preferably methyl, a halogen or a methylsulfonyl group.

In the present specification, $R^4$ and $R^5$ are preferably each independently a hydrogen atom.

In the present specification, $R^6$ is preferably a hydroxyl group, a C1-4 alkyl, or $NR^{12}R^{13}$, is more preferably methyl, a hydroxyl group, amine, methylamine, dimethylamine, piperidine, piperazine, dimethylaminoethylamine, or morpholine, and is especially preferably methyl, a hydroxyl group, methylamine, dimethylamine, or piperazine.

In the present specification, $R^7$ is preferably a C1-4 alkyl group or a C3-6 cycloalkyl group, is more preferably a methyl, ethyl, cyclopropyl, or cyclobutyl group, and is especially preferably a methyl or cyclopropyl group. Meanwhile, the above-described preferable $R^7$, more preferable $R^7$, and especially preferable $R^7$ may be each independently substituted with $CO_2R^{14}$.

In the present specification, $R^8$ is preferably a hydroxyl group, methoxy, ethoxy, amine, methylamine, dimethylamine, piperidine, piperazine, or morpholine, and is more preferably a hydroxyl group, methoxy, amine, dimethylamine, or morpholine.

In the present specification, $R^9$ and $R^{10}$ are preferably each independently a hydrogen atom or methyl.

In the present specification, a 5- to 6-membered saturated cyclic amine that is formed by $R^9$ and $R^{10}$, taken together with the nitrogen atom to which they are attached, is preferably morpholine.

In the present specification, $R^{11}$ is preferably a methyl, ethyl, or cyclopropyl group, and is more preferably a methyl group.

In the present specification, $R^{12}$ and $R^{13}$ are preferably each independently a hydrogen atom, methyl, or ethyl, and preferable $R^{12}$ and $R^{13}$ may be each independently substituted with $NR^{15}R^{16}$ In the present specification, a 5- to 6-membered saturated cyclic amine formed by $R^{12}$ and $R^{13}$, taken together with the nitrogen atom to which they are attached, is preferably piperazine.

In the present specification, $R^{15}$ and $R^{16}$ are preferably each independently, a hydrogen atom, a methyl, or ethyl group.

In the present specification, a 5- to 6-membered saturated cyclic amine formed by $R^{15}$ and $R^{16}$, taken together with the nitrogen atom to which they are attached, is preferably morpholine.

In the present specification, q is preferably an integer of 1 or more, is more preferably an integer of 1 to 4, is furthermore preferably 2 or 3, and is especially preferably 2.

In the present specification, X is preferably N.

In the present specification, general formula (I) is preferably a combination of the above-described preferable meaning of each of Ring 1, Ring 2, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{15}$, $R^{16}$, p, q, r, s, and

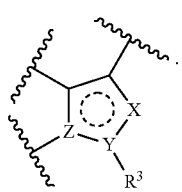

In the present specification, general formula (I) is preferably a compound represented by general formula (I-a):

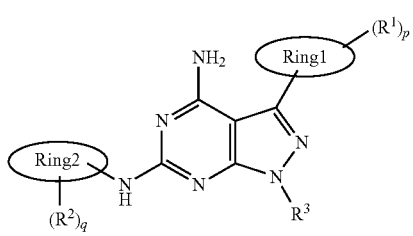

(I-a)

(wherein, all symbols represent the same meanings as symbols set forth in the above item [1]), a salt thereof, a solvate thereof, an N-oxide thereof, or a prodrug of any of these. Another preferable aspect is a compound represented by general formula (I-b):

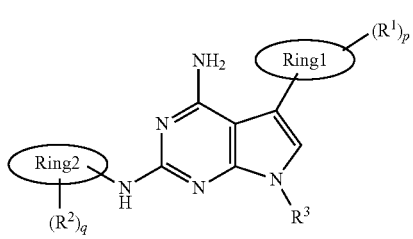

(I-b)

(wherein, all symbols represent the same meanings as symbols set forth in the above item [1]), a salt thereof, a solvate thereof, an N-oxide thereof, or a prodrug of any of these. Another preferable aspect is a compound represented by general formula (I-c):

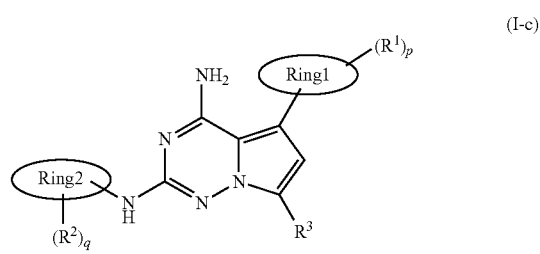

(I-c)

(wherein, all symbols represent the same meanings as symbols set forth in the above item [1]), a salt thereof, a solvate thereof, an N-oxide thereof, or a prodrug of any of these.

In the present specification, another preferable aspect of general formula (I) is a compound represented by general formula (I-1):

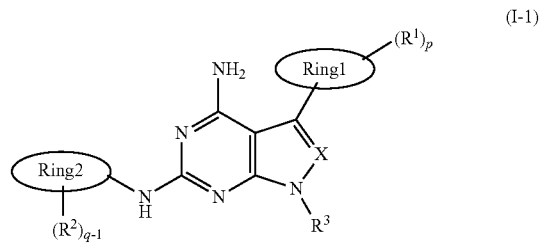

(I-1)

(wherein, all symbols represent the same meanings as symbols set forth in the above item [1] or [4]), a salt thereof, a solvate thereof, an N-oxide thereof, or a prodrug of any of these, and a preferable aspect of general formula (I-1) is a compound represented by general formula (I-d):

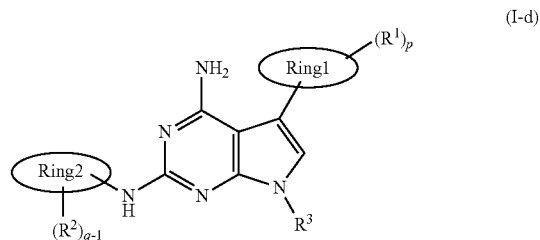

(I-d)

(wherein, all symbols represent the same meanings as symbols set forth in the above item [1] or [4]), a salt thereof, a solvate thereof, an N-oxide thereof, or a prodrug of any of these. Another preferable aspect of general formula (I-1) is a compound represented by general formula (I-e):

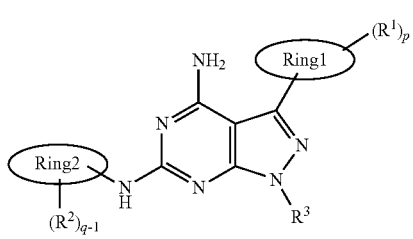

(I-e)

(wherein, all symbols represent the same meanings as symbols set forth in the above item [1] or [4]), a salt thereof, a solvate thereof, an N-oxide thereof, or a prodrug of any of these, and a more preferable aspect is a compound represented by general formula (I-f):

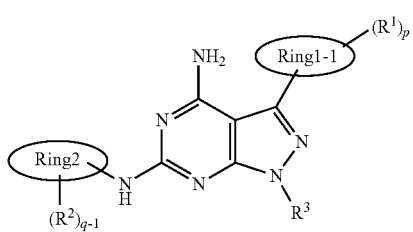

(I-f)

(wherein, Ring 1-1 represents a 5- to 6-membered monocyclic aromatic ring or a 9- to 10-membered bicyclic aromatic ring that may be partially saturated, and all the other symbols represent the same meanings as symbols set forth in the above item [1] or [4]) a salt thereof, a solvate thereof, an N-oxide thereof, or a prodrug of any of these.

Another more preferable aspect is a compound represented by general formula (I-g):

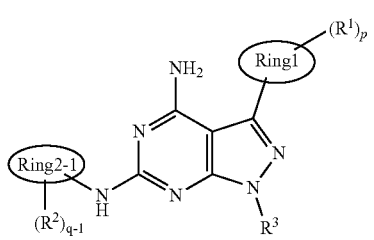

(I-g)

(wherein, Ring 2-1 represents a 5- to 6-membered monocyclic aromatic ring or a 9- to 10-membered bicyclic aromatic ring that may be partially saturated, and all the other symbols represent the same meanings as symbols set forth in the above item [1] or [4]), a salt thereof, a solvate thereof, an N-oxide thereof, or a prodrug of any of these, and is furthermore preferably a compound represented by general formula (I-h):

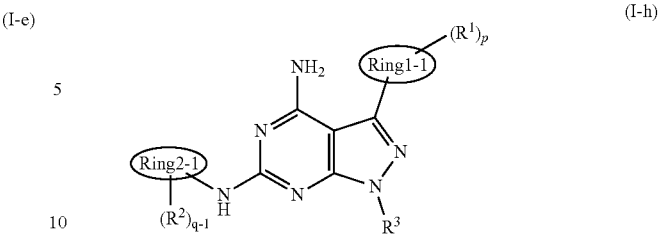

(I-h)

(wherein, Ring 1-1 represents a 5- to 6-membered monocyclic aromatic ring or a 9- to 10-membered bicyclic aromatic ring that may be partially saturated, Ring 2-1 represents a 5- to 6-membered monocyclic aromatic ring or a 9- to 10-membered bicyclic aromatic ring that may be partially saturated, and all the other symbols represent the same meanings as symbols set forth in the above item [1] or [4]), a salt thereof, a solvate thereof, an N-oxide thereof, or a prodrug of any of these.

In the present specification, in general formula selected from the group of the above-described general formula (I-a), general formula (I-b), general formula (I-c), general formula (I-1), general formula (I-d), general formula (I-e), general formula (I-f), general formula (I-g), and general formula (I-h), $R^3$ is preferably each independently C1-4 alkyl, C3-6 cycloalkyl, and a 3- to 6-membered saturated heterocycle, is more preferably methyl, ethyl, isopropyl, tert-butyl, cyclobutanyl, and cyclooxetanyl, is furthermore preferably a C3-4 branched alkyl group that may be substituted with a halogen, and is especially preferably an isopropyl group. The above-described preferable $R^3$ and more preferable $R^3$ may be substituted with a halogen.

In the present specification, another aspect of general formula (I) is the most preferably all the compounds of the present invention described in the following Examples, a salt thereof, a solvate thereof, an N-oxide thereof, or a prodrug of any of these.

In the present specification, unless otherwise specifically indicated, all isomers are included in the present invention. For example, an alkyl group, an alkenyl group, an alkynyl group, an alkoxy group and the like include linear and branched ones. In addition, all of isomers due to ring(s) and fused ring(s) ((E)-, (Z)-, cis- and trans-forms), isomers due to the presence of asymmetric carbon(s) and the like (R-, S-, α- and, β-forms, enantiomer(s) and diastereomer(s)), optically active substances having optical rotation (D-, L-, d- and l-forms), polar substances by chromatographic separation (more polar and less polar substances), compounds in equilibrium, rotational isomers, a mixture thereof in any proportion and a racemic mixture are included in the present invention. In addition, isomers due to tautomerism are all included in the present invention.

In the present specification, unless otherwise specified, the symbol:

represents that a substituent binds to the back side on the paper surface (in other words, α-configuration), the symbol:

represents that a substituent binds to the front side on the paper surface (in other words, β-configuration), and the symbol:

represents an arbitrary mixture of α-configuration and β-configuration, as would be apparent to those skilled in the art.

[Salts]

The compound represented by general formula (I) can be converted into a salt by a known method.

The salt is preferably a pharmaceutically acceptable salt.

The salt is preferably a water-soluble salt.

Examples of the salt include an acid addition salt, an alkali metal salt, an alkaline earth metal salt, an ammonium salt, an amine salt and the like.

Examples of the acid addition salt include an inorganic acid salt such as a hydrochloride, a hydrobromide, a hydroiodide, a sulfate, a phosphate and a nitrate as well as an organic acid salt such as an acetate, a lactate, a tartrate, a benzoate, a citrate, a methanesulfonate, an ethanesulfonate, a trifluoroacetate, a benzenesulfonate, a toluenesulfonate, an isethionate, a glucuronate and a gluconate.

Examples of the alkali metal salt include a potassium salt, a sodium salt and the like.

Examples of the alkaline earth metal salt include a calcium salt, a magnesium salt and the like.

Examples of the ammonium salt include a tetramethyl ammonium salt and the like.

Examples of the amine salt include a triethylamine salt, a methylamine salt, a dimethylamine salt, a cyclopentylamine salt, a benzylamine salt, phenethylamine salt, a piperidine salt, a monoethanolamine salt, a diethanolamine salt, a tris(hydroxymethyl)aminomethane salt, a lysine salt, an arginine salt, an N-methyl-D-glucamine salt and the like.

In addition, the compound of the present invention can be converted into an N-oxide by an arbitrary method. An N-oxide represents a compound obtained by oxidating a nitrogen atom in the compound represented by general formula (I). Specifically, an N-oxide refers to, when X, Y, and Z shown in general formula (I) each independently represent a nitrogen atom, a compound in which at least one of the nitrogen atom and nitrogen atoms in the pyrimidine is oxidized, when Ring 1, Ring 2, and a substituent $R^3$ are a nitrogen-containing heterocycle, a compound in which the nitrogen atom is oxidized, and when substituents $R^1$ and $R^2$ contain a nitrogen atom, a compound in which the nitrogen atom is oxidized.

The compound represented by general formula (I) and a salt thereof can be also converted into a solvate.

The solvate is preferably a nontoxic and water-soluble solvate. Examples of the appropriate solvate include a solvate of water and a solvate of an alcohol based solvent (such as a solvate of ethanol). When a solvate is formed, the compound may be coordinated with an arbitrary number of solvent molecules.

[Prodrugs]

A prodrug of the compound represented by general formula (I) refers to a compound which is converted to the compound represented by general formula (I) by a reaction caused by an enzyme, gastric acid and the like in vivo. Examples of the prodrug of the compound represented by general formula (I) include the followings: when the compound represented by general formula (I) has an amino group, a compound obtained by making the amino group in the compound represented by general formula (I) be acylated, alkylated, or phosphorylated (for example, a compound obtained by making an amino group of the compound represented by general formula (I) be eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated and the like); when the compound represented by general formula (I) has a hydroxyl group, a compound obtained by making the hydroxy group in the compound represented by general formula (I) be acylated, alkylated, phosphorylated or borated (for example, a compound obtained by making the hydroxy group in the compound represented by general formula (I) be acetylated, palmitoylated, propanoylated, pivaloylated, succinylated, fumarylated, alanylated, dimethylaminomethylcarbonylated and the like); and when the compound represented by general formula (I) has a carboxy group, a compound obtained by making the carboxy group in the compound represented by general formula (I) be esterified or amidated (for example, a compound obtained by making the carboxy group in the compound represented by general formula (I) be an ethyl ester, a phenyl ester, a carboxymethyl ester, a dimethylaminomethyl ester, a pivaloyloxymethyl ester, a 1-{(ethoxycarbonyl)oxy}ethyl ester, a phthalidyl ester, a (5-methyl-2-oxo-1,3-dioxolen-4-yl)methyl ester, a 1-{[(cyclohexyloxy)carbonyl]oxy}ethyl ester, a methylamide or the like); and the like. These compounds can be prepared by a known method per se. In addition, the prodrug of the compound represented by general formula (I) may be either a solvate or a non-solvate. Further, the prodrug of the compound represented by general formula (I) may be a compound which is converted to the compound represented by general formula (I) under a physiological condition as described in "Iyakuhin no kaihatsu (Development of Medicaments)", Vol. 7, "Bunshi sekkei (Molecular Design)", pages 163-198, published by Hirokawa-Shoten Ltd. in 1990.

Furthermore, each atom constituting the compound represented by general formula (I) may also be replaced by an isotope (such as $^2H$, $^3H$, $^{13}C$, $^{14}C$, $^{15}N$, $^{16}N$, $^{17}O$, $^{18}O$, $^{18}F$, $^{35}S$, $^{36}Cl$, $^{77}Br$, and $^{125}I$) and the like.

[Processes for the Preparation of the Compound of the Present Invention]

The compound of the present invention represented by general formula (I) can be prepared by a known method. For example, the compound of the present invention can be prepared by appropriately improving methods described in Comprehensive Organic Transformations: A Guide to Functional Group Preparations, 2nd Edition (Richard C. Larock, John Wiley & Sons Inc, 1999), methods equivalent thereto, or the methods described in Examples and the like or combining these methods. Meanwhile, in each of the following processes for the preparation, a raw material compound may be used as a salt. Examples of the salt used include those described as a pharmaceutically acceptable salt of the compound represented by general formula (I).

Among the compounds of the present invention represented by general formula (I), a compound in which:

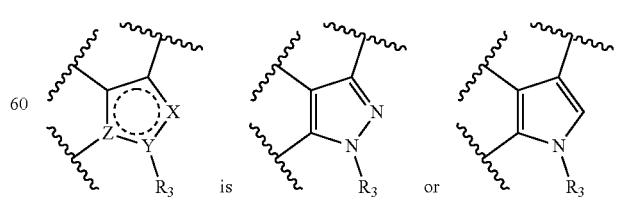

can be prepared by a method shown by the following Reaction Scheme I.

Reaction Scheme I

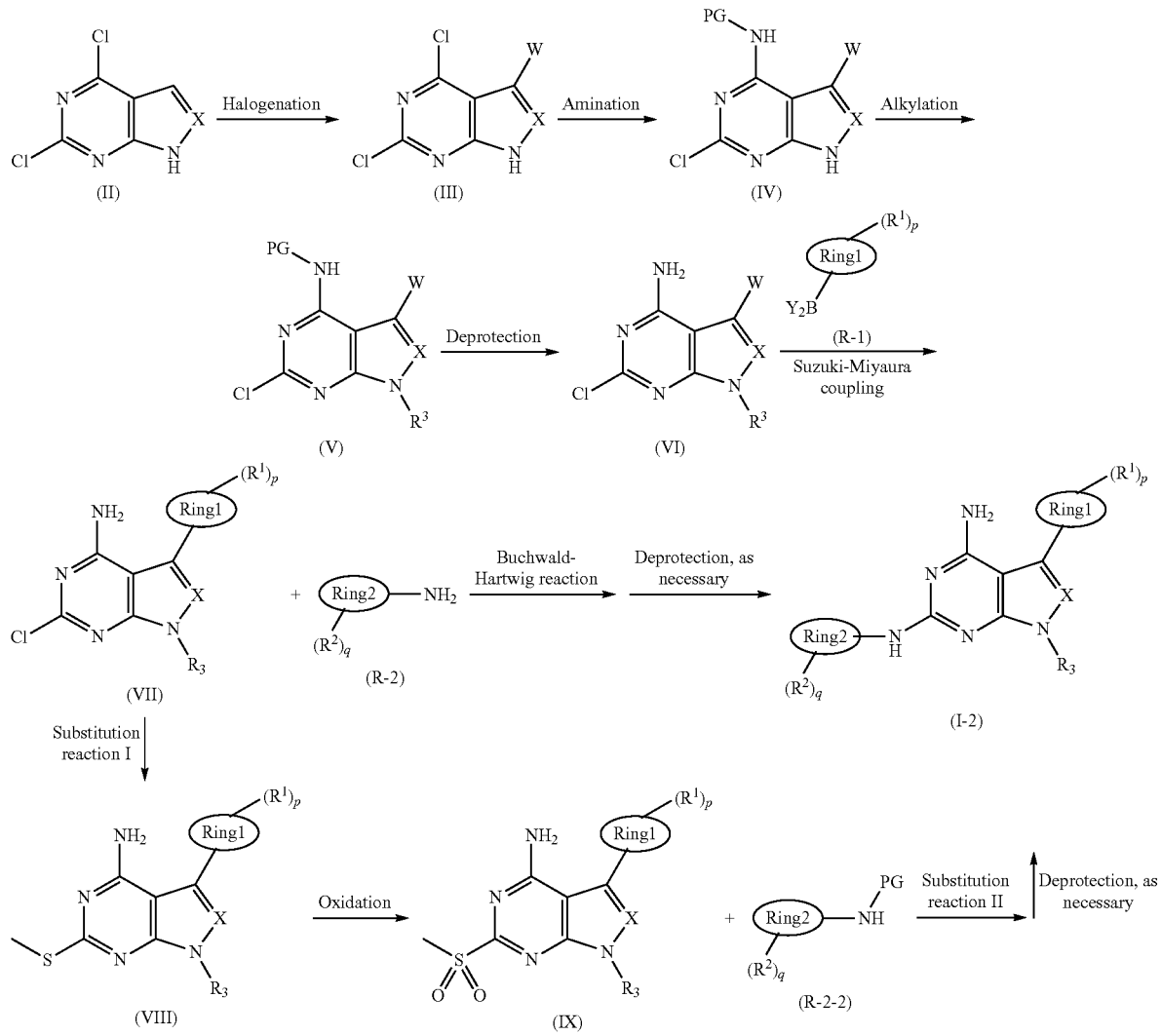

(wherein, W represents a halogen, PG represents a protecting group of an amino group, $BY_2$ represents a boronic acid or a boronate ester, and the other symbols represent the same meanings as symbols set forth in the above item [1] or [4]).

The compound of the present invention having an amino group, a carboxyl group, or a hydroxyl group can be prepared as follows. The reactions to Buchwald-Hartwig reaction, or substitution reaction II shown in the above-described Reaction Scheme I are conducted by using, as necessary, a compound protected by a protecting group which is generally used to these groups, for example, a protecting group described in "Comprehensive Organic Transformations: A Guide to Functional Group Preparations 2nd Edition (Richard C. Larock, John Wiley & Sons Inc, 1999)", and thereafter, a known deprotection reaction, or, for example, a deprotection reaction described in "Comprehensive Organic Transformations: A Guide to Functional Group Preparations 2nd Edition (Richard C. Larock, John Wiley & Sons Inc, 1999)" is conducted.

In the present specification, examples of the "protecting group of an amino group" when PG is a protecting group of an amino group include a protecting group described in "Comprehensive Organic Transformations: A Guide to Functional Group Preparations 2nd Edition (Richard C. Larock, John Wiley & Sons Inc, 1999)".

In Reaction Scheme I, a reaction step (halogenation) to prepare the compound represented by general formula (III) from the compound represented by general formula (II) can be performed by the method described in the present specification or a known method.

In Reaction Scheme I, a reaction step (amination) to prepare the compound represented by general formula (IV) from the compound represented by general formula (III) can be performed by the method described in the present specification or a known method.

In Reaction Scheme I, a reaction step (alkylation) to prepare the compound represented by general formula (V) from the compound represented by general formula (VI) can be performed by the method described in the present specification or a known method.

In Reaction Scheme I, a reaction step (deprotection) to prepare the compound represented by general formula (VI) from the compound represented by general formula (V) can be performed by the method described in the present specification or a known method.

In Reaction Scheme I, a reaction step (Suzuki-Miyaura coupling) to prepare the compound represented by general formula (VII) from the compound represented by general formula (VI) can be performed by the method described in the present specification or a known method.

In Reaction Scheme I, a reaction step (Buchwald-Hartwig reaction) to prepare the compound represented by general formula (I-2) from the compound represented by general formula (VII) can be performed by the method described in the present specification or a known method.

On the other hand, in Reaction Scheme I, the compound represented by general formula (I-2) can be also prepared through a reaction step (substitution reaction I) to prepare the compound represented by general formula (VIII) from the compound represented by general formula (VII), a reaction step (oxidation reaction) to prepare the compound represented by general formula (IX) from the compound represented by general formula (VIII), substitution reaction II from the compound represented by general formula (IX), and a deprotection reaction performed as necessary. The above-described substitution reaction I, oxidation reaction, and substitution reaction II can be performed by the method described in the present specification or a known method.

Among the compounds of the present invention represented by general formula (I), a compound in which:

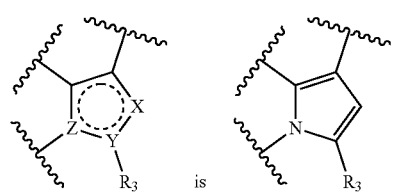

is can be prepared by a method shown by the following Reaction Scheme II.

Reaction Scheme II

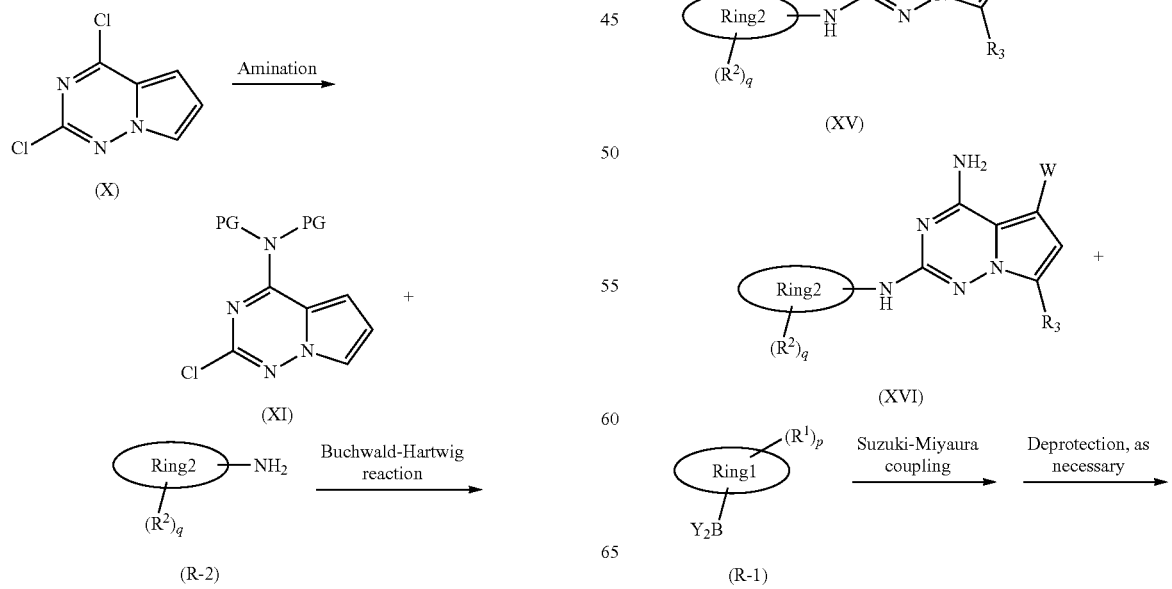

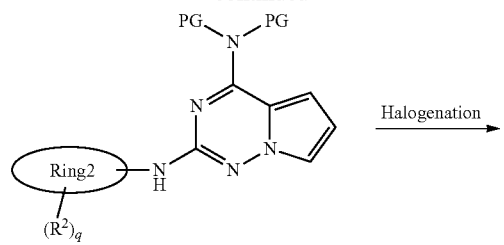

(XII)

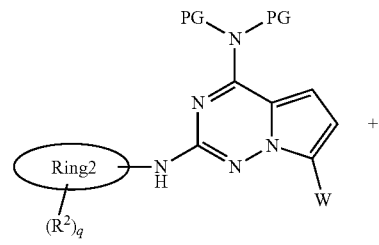

(XIII)

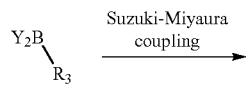

(R-3)

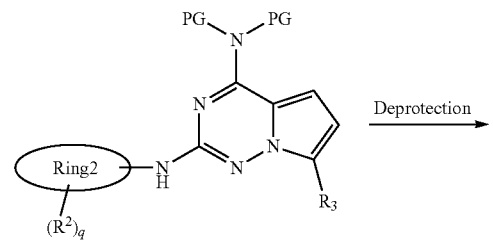

(XIV)

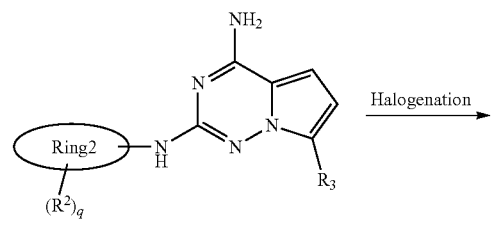

(XV)

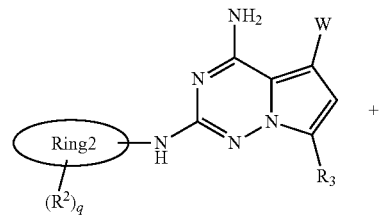

(XVI)

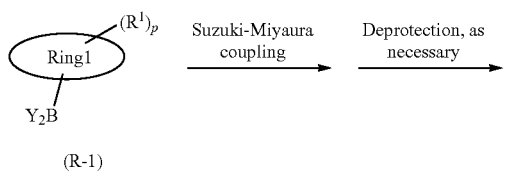

(R-1)

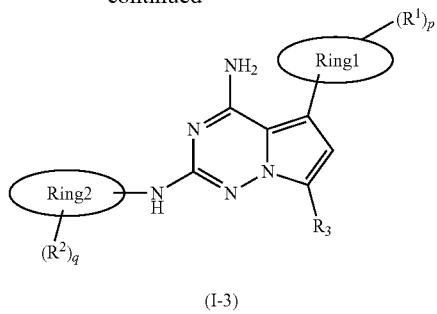

(I-3)

(wherein, W represents a halogen, P represents a protecting group of an amino group, BY$_2$ represents each independently a boronic acid or a boronate ester, and the other symbols represent the same meanings as symbols set forth in the above item ([1]).

The compound of the present invention having an amino group, a carboxyl group, or a hydroxyl group can be prepared as follows. Suzuki-Miyaura coupling reaction described in the above-described Reaction Scheme is conducted by using as necessary, a compound protected by a protecting group which is generally used to these groups, for example, a protecting group described in "Comprehensive Organic Transformations: A Guide to Functional Group Preparations 2nd Edition (Richard C. Larock, John Wiley & Sons Inc, 1999)", and thereafter, a known deprotection reaction, or, for example, a deprotection reaction described in "Comprehensive Organic Transformations: A Guide to Functional Group Preparations 2nd Edition (Richard C. Larock, John Wiley & Sons Inc, 1999)" is conducted.

In Reaction Scheme II, a reaction step (amination reaction) to prepare the compound represented by general formula (XI) from the compound represented by general formula (X) can be performed by the method described in the present specification or a known method.

In Reaction Scheme II, a reaction step (Buchwald-Hartwig reaction) to prepare the compound represented by general formula (XII) from the compound represented by general formula (XI) can be performed by the method described in the present specification or a known method.

In Reaction Scheme II, a reaction step (halogenation reaction) to prepare the compound represented by general formula (XIII) from the compound represented by general formula (XII) can be performed by the method described in the present specification or a known method.

In Reaction Scheme II, a reaction step (Suzuki-Miyaura coupling reaction) to prepare the compound represented by general formula (XVI) from the compound represented by general formula (XIII) can be performed by the method described in the present specification or a known method.

In Reaction Scheme II, a reaction step (deprotection reaction) to prepare the compound represented by general formula (XV) from the compound represented by general formula (XIV) can be performed by the method described in the present specification or a known method.

In Reaction Scheme II, a reaction step (halogenation reaction) to prepare the compound represented by general formula (XVI) from the compound represented by general formula (XV) can be performed by the method described in the present specification or a known method.

In Reaction Scheme II, a reaction step (Suzuki-Miyaura coupling reaction) to prepare the compound represented by general formula (I-3) from the compound represented by general formula (XVI) can be performed by the method described in the present specification or a known method.

In Reaction Schemes I and II, an amination reaction is known, and for example, is performed by using a corresponding amine compound, in an organic solvent (such as methanol, ethanol, isopropanol, N,N-dimethylformamide, dimethylsulfoxide, tetrahydrofuran, dioxane, dichloromethane and chloroform) or in the absence of a solvent, in the presence or absence of a base (such as triethylamine, diisopropylethylamine, cesium carbonate, potassium carbonate, and sodium carbonate), at 0° C. to under reflux.

In Reaction Schemes I and II, a halogenation reaction is known, and for example, is performed by using a halogenating agent (such as N-iodosuccinimide, N-bromosuccinimide, N-chlorosuccinimide, 1,3-diiodo-5,5-dimethylhydantoin, 1,3-dibromo-5,5-dimethylhydantoin, and 1,3-dichloro-5,5-dimethylhydantoin), in an organic solvent (such as dichloromethane, chloroform, methanol, tetrahydrofuran, N,N-dimethylformamide, acetonitrile, and ethyl acetate), in the presence or absence of an acid (such as sulfuric acid, and acetic acid), at a temperature of −70° C. to 120° C.

In Reaction Schemes I and II, an alkylation reaction is known, and for example, alkylation can be performed by subjecting the compound to Mitsunobu reaction. Mitsunobu reaction is known, and for example, is performed by using a corresponding alcohol compound, in an organic solvent (such as dichloromethane, diethyl ether, tetrahydrofuran, acetonitrile, benzene, toluene, or a mixed solvent of 2 or more of them), in the presence of an azo compound (such as diethyl azodicarboxylate (DEAD), diisopropyl azodicarboxylate, 1,1'-(azodicarbonyl)dipiperidine, and 1,1'-azobis(N,N-dimethylformamide)) and a phosphine compound (such as triphenylphosphine, tributylphosphine, trimethylphosphine, and polymer-supported triphenylphosphine) at 0 to 60° C.

In addition, alkylation can be also performed by using an alkyl halide. Alkylation using an alkyl halide is known, and is performed by using a corresponding alkyl halide (such as an iodide, a bromide, and a chloride), in an organic solvent (such as dichloromethane, chloroform, tetrahydrofuran, acetonitrile, and N,N-dimethylformamide), in the presence of a base (such as triethylamine, diisopropylamine, potassium carbonate, and cesium carbonate), at 0° C. to under reflux.

In Reaction Schemes I and II, a deprotection reaction is known, and can be performed as follows.

Examples of the protecting group of an amino group include a benzyloxycarbonyl group, a t-butoxycarbonyl group, an allyloxycarbonyl (Alloc) group, a 1-methyl-1-(4-biphenyl)ethoxycarbonyl (Bpoc) group, a trifluoroacetyl group, a 9-fluorenylmethoxycarbonyl group, a benzyl (Bn) group, a p-methoxybenzyl group, a benzyloxymethyl (BOM) group, a 2-(trimethylsilyl)ethoxymethyl (SEM) group and the like.

The protecting group is not particularly limited to those described above as long as the protecting group can be eliminated easily and selectively. For example, protecting groups described in Green's Protective Groups in Organic Synthesis, Fifth Edition (Peter G. M. Wuts, John Wiley & Sons Inc, 2014) are used.

A deprotection reaction of a protecting group is well known and examples of the deprotection reaction include,
(1) alkaline hydrolysis;
(2) a deprotection reaction under an acidic condition;
(3) a deprotection reaction by hydrogenolysis;
(4) a deprotection reaction by using a fluoride ion;

(5) a deprotection reaction by using a metal;
(6) a deprotection reaction by using a metal complex; and the like.

These methods are described specifically as follows:

(1) A deprotection reaction by alkaline hydrolysis is performed, for example, in an organic solvent (such as methanol, tetrahydrofuran and dioxane), by using a hydroxide of an alkali metal (such as sodium hydroxide, potassium hydroxide, and lithium hydroxide), a hydroxide of an alkaline earth metal (such as barium hydroxide and calcium hydroxide), a carbonate (such as sodium carbonate and potassium carbonate), an aqueous solution thereof or a mixture thereof at a temperature of 0 to 40° C.

(2) A deprotection reaction under an acidic condition is performed, for example, in an organic solvent (such as dichloromethane, chloroform, dioxane, ethyl acetate, and anisole), in an organic acid (such as acetic acid, trifluoroacetic acid, methanesulfonic acid, and p-tosic acid), an inorganic acid (such as hydrochloric acid, and sulfuric acid) or a mixture thereof (such as hydrobromic acid/acetic acid) at a temperature of 0 to 100° C.

(3) A deprotection reaction by hydrogenolysis is performed, for example, in a solvent (such as an ethereal solvent (such as tetrahydrofuran, dioxane, dimethoxyethane and diethyl ether), an alcohol based solvent (such as methanol and ethanol), a benzene based solvent (such as benzene and toluene), a ketone based solvent (such as acetone and methyl ethyl ketone), a nitrile based solvent (such as acetonitrile), an amide based solvent (such as dimethylformamide), water, ethyl acetate, acetic acid or a mixed solvent of two or more of them), in the presence of a catalyst (such as palladium on carbon, palladium black, palladium hydroxide, platinum oxide and Raney nickel), under a hydrogen atmosphere at a normal pressure or under pressurization or in the presence of ammonium formate, at a temperature of 0 to 200° C.

(4) A deprotection reaction using a fluoride ion is performed, for example, in a water-miscible organic solvent (such as tetrahydrofuran, and acetonitrile), by using tetrabutylammonium fluoride at a temperature of 0 to 40° C.

(5) A deprotection reaction by using a metal is performed, for example, in an acidic solvent (such as acetic acid, a buffer solution of pH 4.2 to 7.2 or a mixed solution of such a solution and an organic solvent such as tetrahydrofuran), in the presence of powdery zinc at a temperature of 0 to 40° C., if necessary, while applying an ultrasonic wave.

(6) A deprotection reaction by using a metal complex is performed, for example, in an organic solvent (such as dichloromethane, dimethylformamide, tetrahydrofuran, ethyl acetate, acetonitrile, dioxane, and ethanol), water or a mixed solvent thereof, in the presence of a trapping reagent (such as tributyltin hydride, triethylsilane, dimedone, morpholine, diethylamine and pyrrolidine), an organic acid (such as acetic acid, formic acid and 2-ethylhexanoic acid) and/or an organic acid salt (such as sodium 2-ethylhexanoate and potassium 2-ethylhexanoate), in the presence or absence of a phosphine-based reagent (such as triphenylphosphine), by using a metal complex (such as tetrakistriphenylphosphinepalladium(0), bis(triphenylphosphine)palladium(II) dichloride, palladium(II) acetate and chlorotris(triphenylphosphine)rhodium(I)), at a temperature of 0 to 40° C.

In addition to the above-described methods, a deprotection reaction can be performed, for example, by a method described in Green's Protective Groups in Organic Synthesis, Fifth Edition (Peter G. M. Wuts, John Wiley & Sons Inc, 2014).

As those skilled in the art could easily understand, the compound of the present invention of interest can be easily prepared by using these deprotection reactions properly.

In Reaction Schemes I and II, Suzuki-Miyaura coupling reaction is known, and for example, is performed by conducting the reaction by using a corresponding boron compound, in an organic solvent (such as benzene, toluene, dimethylformamide, dioxane, tetrahydrofuran, methanol, acetonitrile, dimethoxyethane, and acetone), in the presence of a base (such as sodium ethylate, sodium hydroxide, potassium hydroxide, triethylamine, sodium carbonate, sodium bicarbonate, potassium carbonate, cesium carbonate, thallium carbonate, tripotassium phosphate, cesium fluoride, barium hydroxide, and tetrabutylammonium fluoride), an aqueous solution thereof, or a mixture thereof, in the presence of a catalyst (such as (tetrakis(triphenylphosphine)palladium ($Pd(PPh_3)_4$), bis(triphenylphosphine)palladium dichloride ($PdCl_2$ $(PPh_3)_2$), palladium acetate (Pd $(OAc)_2$), palladium black, [1,1'-bis(diphenylphosphino)ferrocene]dichloropalladium ($PdCl_2$ $(dppf)_2$), diallylpalladium dichloride ($PdCl_2$ $(allyl)_2$), and phenylbis(triphenylphosphine)palladium iodide ($PhPdI(PPh_3)_2$)) at room temperature to 120° C.

In Reaction Schemes I and II, Buchwald-Hartwig reaction is known, and for example, is performed by conducting the reaction by using a corresponding amine compound, in an organic solvent (such as dioxane, toluene, dimethylformamide, N-methylpyrrolidone, dimethylsulfoxide, tert-butanol, or an appropriate mixed solvent of these organic solvents), in the presence of a palladium catalyst (such as palladium acetate, allylpalladium(II) chloride dimer ($Pd_2$ $Cl_2$ $(allyl)_2$), and tris(dibenzylideneacetone)dipalladium(0) ($Pd_2$ $(dba)_3$)), and a phosphorus ligand (such as triphenylphosphine, tributylphosphine, tricyclohexylphosphine, Xantphos, and Xphos), in the presence of a base (such as potassium carbonate, cesium carbonate, sodium butoxide, and tripotassium phosphate), at a temperature of room temperature to about 180° C.

In Reaction Scheme I, substitution reaction I is known, and is performed, for example, by using a corresponding thiol or a corresponding metal thioalkoxide, in an organic solvent (such as dimethylsulfoxide, N,N-dimethylformamide, methanol, ethanol, isopropanol, and tetrahydrofuran), in water, or in a mixed solvent thereof, in the presence or absence of a base (such as triethylamine, and diisopropylethylamine), at 0° C. to under reflux.

In Reaction Scheme I, an oxidation reaction of sulfur is known, and is performed, for example, in an organic solvent (such as dichloromethane, chloroform, benzene, hexane, methanol, t-butyl alcohol, acetone, acetonitrile, tetrahydrofuran, acetic acid, and N,N-dimethylformamide), in water or in a mixed solvent thereof, in the presence of an excess oxidizing agent (such as hydrogen peroxide, sodium periodate, acyl nitrite, sodium perborate, sodium hypochlorite, a peracid (such as 3-chloroperbenzoic acid, and peracetic acid), oxone (trade name, hereinafter abbreviated as oxone; potassium peroxymonosulfate), potassium permanganate, chromic acid, and dimethyldioxolane), in the presence or absence of an oxidation catalyst (such as hexaammonium heptamolybdate tetrahydrate (($NH_4)_6$ $Mo_7$ $O_{24}$·$4H_2$ O)) at a temperature of 20 to 60° C.

In Reaction Scheme I, substitution reaction II is known, and is performed, for example, by using a corresponding amine, in an organic solvent (such as N,N-dimethylformamide, dimethylsulfoxide, ethanol, isopropanol, acetonitrile, and tetrahydrofuran), in the presence or absence of a base (such as triethylamine, diisopropylamine, and sodium tert-butoxide), at 0° C. to under reflux.

In Reaction Schemes, the compounds represented by general formula (II), general formula (X), general formula (R-1), general formula (R-2), general formula (R-2-2), and general formula (R-3) used as the starting materials are known or can be easily prepared by using a known method, for example, a method described in "Comprehensive Organic Transformations: A Guide to Functional Group Preparations 2nd Edition (Richard C. Larock, John Wiley & Sons Inc, 1999)".

Among the compounds of the present invention represented by general formula (I), compounds other than those described above can be prepared by combining the methods described in Examples in the present specification or a known method, for example, a method described in "Comprehensive Organic Transformations: A Guide to Functional Group Preparations 2nd Edition (Richard C. Larock, John Wiley & Sons Inc, 1999)".

In the present specification, a reaction which involves heating in each of the reactions can be performed by using a water bath, an oil bath, a sand bath or a microwave as apparent to those skilled in the art.

In the present specification, a solid phase-supported reagent which is supported by a macromolecular polymer (such as polystyrene, polyacrylamide, polypropylene and polyethylene glycol) may be used appropriately, in each of the reactions.

In the present specification, the reaction product in each of the reactions can be purified by a conventional purification means. Examples of the purification means include distillation under a normal pressure or a reduced pressure, high performance liquid chromatography which uses silica gel or magnesium silicate, thin-layer chromatography, an ion exchange resin, a scavenger resin, column chromatography, or methods such as washing, recrystallization and the like. The purification may be performed at each of reactions or may be performed after the completion of several reactions.

[Toxicity]

The toxicity of the compound of the present invention is low, and therefore, the compound of the present invention can be used as a medicine safely.

[Application to Pharmaceuticals]

The compound of the present invention has a Brk inhibitory activity, and therefore, the compound of the present invention is useful as an agent for preventing and/or treating Brk-related diseases, for example, cancer and the like.

More specific examples of cancer include breast cancer, ovarian cancer, large bowel cancer (such as, colon cancer), lung cancer (such as non-small-cell lung cancer), prostate cancer, head and neck cancer (such as oral squamous cell cancer, head and neck squamous cell cancer, pharyngeal cancer, laryngeal cancer, tongue cancer, thyroid cancer, and acoustic schwannoma), lymphoma (such as B-cell lymphoma, and T-cell lymphoma), brain tumor, glioma, pituitary adenoma, uveal malignant melanoma, meningioma, thymoma, mesothelioma, esophageal cancer, gastric cancer, duodenal cancer, hepatocellular cancer, bile duct cancer, gallbladder cancer, pancreatic cancer, renal cell cancer, renal pelvis-ureteral cancer, bladder cancer, penile cancer, testicular cancer, uterine cancer, vaginal cancer, vulvar cancer, skin cancer (such as malignant melanoma (melanoma)), malignant bone tumor, soft tissue sarcoma, chondrosarcoma, leukemia (such as acute myeloid leukemia, acute lymphocytic leukemia, chronic myeloid leukemia, and chronic lymphocytic leukemia), myelodysplastic syndrome, multiple myeloma and the like.

The compound of the present invention may be administered as a combined agent by being combined with other drug(s) for the purpose of:
1) complementation and/or enhancement of the preventing and/or treating effect of the compound,
2) improvement in kinetics•absorption, and reduction of the dose of the compound, and/or
3) reduction of the side effect of the compound.

The combined agent of the compound of the present invention with other drug(s) may be administered in the form of a compounding agent in which both ingredients are compounded in a preparation or may be administered by means of separate preparations. The case of being administered by means of separate preparations includes concomitant administration and administrations with a time difference. In addition, in the case of the administrations with a time difference, the compound of the present invention may be firstly administered, followed by administration of the other drug(s). Alternatively, the other drug(s) may be firstly administered, followed by administration of the compound of the present invention. A method for administering the compound of the present invention and that for administering the other drug(s) may be the same or different.

The disease against which the above-described combined agent exhibits the preventing and/or treating effect is not particularly limited as long as the disease is that against which the preventing and/or treating effect of the compound of the present invention is complemented and/or enhanced.

Examples of the other drug(s) for complementation and/or enhancement of the preventing and/or treating effect of the compound of the present invention on cancer include an alkylating agent, an antimetabolite, an anticancer antibiotic, a plant-derived preparation, a hormone preparation, a platinum compound, a topoisomerase inhibitor, a kinase inhibitor, an immune checkpoint inhibitor, an anti-CD20 antibody, an anti-HER2 antibody, an anti-EGFR antibody, an anti-VEGF antibody, other anticancer drugs and the like.

Examples of the alkylating agent include cyclophosphamide, ifosfamide, dacarbazine, nimustine hydrochloride, ranimustine, bendamustine, thiotepa, carboquone and the like.

Examples of the antimetabolite include methotrexate, pemetrexed, fluorouracil, tegafur, tegafur/uracil, tegafur/gimestat/potassium otastat, doxifluridine, capecitabine, cytarabine, gemcitabine hydrochloride, fludarabine, nelarabine, carmofur, procarbazine hydrochloride and the like.

Examples of the anticancer antibiotic include mitomycin C, doxorubicin hydrochloride, aclarubicin hydrochloride, pirarubicin hydrochloride, epirubicin, chromomycin A3, bleomycin, peplomycin sulfate, therarubicin and the like.

Examples of the plant-derived preparation include irinotecan hydrochloride, etoposide, vincristine sulfate, vinblastine sulfate, vindesine sulfate, vinorelbine ditartrate, docetaxel hydrate, eribulin mesylate, paclitaxel and the like.

Examples of the hormone preparation include estramustine phosphate sodium, flutamide, bicalutamide, goserelin acetate, leuprorelin acetate, tamoxifen citrate, toremifene citrate, anastrozole, letrozole, exemestane, mepitiostane, medroxyprogesterone acetate, epitiostanol, fosfestrol, fadrozole hydrochloride hydrate, abiraterone, fulvestrant, aminoglutethimide and the like.

Examples of the platinum compound include carboplatin, cisplatin, nedaplatin, oxaliplatin and the like.

Examples of the topoisomerase inhibitor include topotecan, sobuzoxane and the like.

Examples of the kinase inhibitor include an EGFR inhibitor including erlotinib, gefitinib, and afatinib, an HER2 inhibitor including lapatinib, a BCR-ABL inhibitor including imatinib, an ALK inhibitor including crizotinib, a multikinase inhibitor including regorafenib, and dasatinib and the like.

Examples of the immune checkpoint inhibitor include an anti-CTLA-4 antibody including ipilimumab, an anti-PD-1 antibody including nivolumab, and pembrolizumab, an anti-PD-L1 antibody including RG7446/MPDL3280A, MSB0010718C, and MEDI4736 and the like.

Examples of the anti-CD20 antibody include rituximab, ibritumomab, ibritumomab tiuxetan, ocrelizumab and the like.

Examples of the anti-HER2 antibody include trastuzumab, trastuzumab emtansine, pertuzumab and the like.

Examples of the anti-EGFR antibody include cetuximab, panitumumab and the like.

Examples of the anti-VEGF antibody include bevacizumab and the like.

A mass ratio of the compound of the present invention and other drug(s) is not particularly limited.

Arbitrary two or more kinds of other drugs may be administered in combination.

In addition, other drug(s) for complementation and/or enhancement of the preventing and/or treating effect of the compound of the present invention includes not only that which has been found up to now but also that which will be found in future based on the above-described mechanism.

Examples of other methods of treating to be combined with the compound of the present invention for preventing and/or treating cancer include radiation therapy (such as X-ray, γ-ray, electron beam, proton beam, and heavy ion), chimeric antigen receptor T cell therapy (CAR-T), thermotherapy, NK cell therapy, NKT cell therapy and the like.

In order to use the compound of the present invention as a single agent or as a combined agent which combines the compound of the present invention with other drug(s) for the purpose of the prevention and/or treatment of the above-described disease, the substance which is an active ingredient is normally formulated with various types of pharmaceutically acceptable carriers such as additives and solvents and is administered systemically or locally in the form of an oral preparation or a parenteral preparation. Here, a pharmaceutically acceptable carrier means a substance other than an active ingredient which is generally used for formulation of a medicine. It is preferable that the pharmaceutically acceptable carrier does not exhibit a pharmacological action in a dose of the formulation, is harmless, and does not interfere with a therapeutic effect of the active ingredient. In addition, the pharmaceutically acceptable carrier may also be used for the purpose of enhancing utility of the active ingredient and the formulation, making formulation easy, stabilizing quality, improving usability or the like. Specifically, a substance described in "Iyakuhin tenkabutsujiten (Japanese Pharmaceutical Excipients Directory)" (edited by Japan pharmaceutical Excipients Council), YAKUJI NIPPO LIMITED published in 2000 or the like may be selected appropriately according to a purpose.

Dosage forms for administration includes, for example, oral preparation (e.g.: tablets, capsules, granules, powders, oral solutions, syrups, oral jelly agents, etc.), oro-mucosal preparation (e.g.: tablets for oro-mucosal application, sprays for oro-mucosal application, semi-solid preparations for oro-mucosal application, gargles, etc.), preparations for injection (e.g.: injections, etc.), preparations for dialysis (e.g.: dialysis agents, etc.), preparation for inhalation (e.g.: inhalations, etc.), preparation for ophthalmic application (e.g.: ophthalmic liquids and solutions, ophthalmic ointments, etc.), preparation for otic application (e.g.: ear preparation, etc.), preparations for nasal application (nasal preparations, etc.), preparation for recta (e.g.: suppositories, semi-solid preparations for rectal application, enemas for rectal application, etc.), preparations for vaginal application (e.g.: tablets for vaginal use, suppositories for vaginal use, etc.) and preparation for cutaneous application (e.g.: solid preparations for cutaneous application, liquids and solutions for cutaneous application, sprays, ointment, creams, gels, patches, etc.).

[Oral Preparation]

Oral preparation include, for example, tablets, capsules, granules, powders, liquids and solution for oral administration, syrups, Jellies for oral administration, etc. As oral preparation, there are Immediate-release dosage forms showing a release pattern of active substances that is not intentionally modified and modified-release dosage forms are preparations showing modified pattern of active substances that is suitably modified for the desired purpose by means of a specific formulation design and/or manufacturing methods. Modified-release dosage forms include enteric-coated and extended-release preparations. Enteric-coated (delayed-release) preparations release the bulk of the active substances not in stomach but mainly in small intestine, in order to prevent degradation or decomposition of the active substances in stomach or to decrease the irritation of the active substances on stomach. Enteric-coated preparations are generally coated with an acid-insoluble enteric film. Extended-release preparations are designed to control the release rate and release period of active substances and to restrict the release to appropriate sites in the gastrointestinal tracts in order to decrease the dosing frequency and/or to reduce adverse or side effects. Extended-release preparations are generally prepared by using suitable agents that prolong the release of the active substances. Oral dosage forms such as capsules, granules and tablets can be coated with appropriate coating agents, such as sugars, sugar alcohols, or polymers, for the purpose of enabling the ingestion easy or of preventing degradation of the active substances.

(1) Tablets

Tablets are solid preparation having a desired shape and size, intended for oral administration, and include orally disintegrating tablets, chewable tablets, effervescent tablets, dispersible tablets, soluble tablets besides generally called tablets such as plain tablets, film-coated tablets, sugar-coated tablets, multi-layered tablets and pressure-coated tablets, etc. Plain tables are usually prepared according to the following methods (a), (b) and (c):

(a) Mix homogeneously active substances and excipients such as diluents, binders and disintegrators, granulate with water or a binder solution by suitable methods, mix with a lubricant, and then compress into a desired shape and size;

(b) Mix homogeneously active substances and excipients such as diluents, binders, and disintegrators, and then directly compress, or compress after adding active substances and lubricant to granules previously prepared from excipients and then mixing homogeneously;

(c) Mix homogeneously active substances and excipients such as diluents and binders, moisten with a solvent, form into a certain shape and size, and then dry by suitable methods;

Film-coated tablets can be prepared, usually, by coating plain tablets using suitable coating agents such as polymers. Sugar-coated tablets can be prepared, usually, by coating plain tablets using suitable coating agents including sugars and sugar alcohols. Multiple-layer tablets can be prepared by compressing granules of different compositions to form layered tablets by a suitable method. Pressure-coated tablets can be prepared by compressing granules to cover inner core tablets with different compositions. In addition, tablets can be prepared as enteric coated tablets or timed-release tablet by suitable well-known methods. Orally disintegrating tablets, chewable tablets, effervescent tablets, dispersible tablets, soluble tablets are tablets which are added distinct role by selecting suitable excipients, and can be prepared according to said methods. Orally disintegrating tablets are tablets which are quickly dissolved or disintegrated in the oral cavity; Chewable tablets are tablets which are administered by chewing; Effervescent tablets are tablets which are quickly dissolved or dispersed with bubbles in water; Dispersible tablets are tablets which are administered after having been dispersed in water; Soluble tablets are tablets which are administered after having been dissolved in water. Effervescent tablets can be prepared using suitable acidic substances and carbonates or hydrogen carbonates as excipients.

(2) Capsules

Capsules are preparations enclosed in capsules or wrapped with capsule bases, intended for oral administration. Capsules are classified into hard capsules and soft capsules. Hard capsules can be prepared by a method where a homogeneous mixture of active substances with diluents and other suitable excipients, or granules or formed masses prepared by a suitable methods, are filled into capsule shells as they are or after slight compression. Soft capsules can be prepared by a method where active substances and suitable excipients are mixed, enclosed by a suitable capsule base such as gelatin plasticized by addition of glycerin, D-sorbitol, etc. and molded in a suitable shape and size. Capsules can be prepared as enteric-coated or extended-release capsules by a suitable well-known method. Coloring agents and preservatives, etc. may be added to the capsule bases.

(3) Granules

Granules are preparations prepared by granulation, and include effervescent granules besides generally called granules. Granules can be prepared by the following methods (a), (b), and (c);
(a) To powdery active substances add diluents, binders, disintegrators, or other suitable excipients, mix to homogenize, and granulate by a suitable method;
(b) To previously granulated active substances add excipients such as diluents, and mix to homogenize;
(c) To previously granulated active substances add excipients such as diluents, and granulate by a suitable method; Granules can be coated if necessary, and can be prepared as enteric-coated or extended-release granules. Effervescent granules can be prepared using suitable acidic substances and carbonates or hydrogen carbonates. Effervescent granules are granules which are quickly dissolved or dispersed with bubbles in water. Granules can be prepared as fine grain agents by adjusting particle size.

(4) Powders

Powders are preparations in powder form, and are usually prepared by homogeneously mixing active substances with diluents or other suitable excipients.

(5) Liquids and Solution for Oral Administration

Liquids and solution for oral administration are preparations in liquid form or flowable and viscous gelatinous state, and elixirs, suspensions, emulsions and lemonades are included in this category besides generally called Liquids and solution for oral administration. Liquids and solution for oral administration are usually prepared by dissolving, emulsifying or suspending active substances in purified water together with excipients, and by filtering if necessary.

Elixirs are clear, sweetened and aromatic liquid preparations, containing ethanol, and are usually prepared by dissolving solid active substances or their extractives in ethanol and purified water, adding aromatic agents and sucrose, other sugars or sweetening agents, and clarifying by filtration or other procedure. Suspensions are liquid preparations of active substances suspended finely and homogeneously in a vehicle, and are usually prepared by adding suspending agent or other suitable excipients and purified water or oil to solid active substances, and suspending homogeneously as the whole by a suitable method. Emulsions are liquid preparations of active substances emulsified finely and homogeneously in a liquid vehicle, and are usually prepared by adding emulsifying agents and purified water to liquid active substances, and emulsifying finely and homogeneously by a suitable method. In addition, Lemonades are sweet and sour, clear liquid preparations, intended for oral administration.

(6) Syrups

Syrups are viscous liquid or solid preparations containing sugars or sweetening agents, and include preparation for syrups. Syrups are usually prepared by dissolving, mixing, suspending or emulsifying active substances in a solution of sucrose, other sugars or sweetening agents, or in simple syrup. Where necessary, the mixture is boiled, and filtered while hot. Preparations for syrups are preparations in form of granules or powders, which becomes syrups by adding water. They may be termed "dry syrups". Preparations for syrups are usually prepared with sugars or sweetening agents according to said preparation method of granules or powders.

(7) Jellies for Oral Administration

Jellies for oral administration are non-flowable gelatinous preparations having a certain shape and size, and usually prepared by mixing active substances with suitable excipients and polymer gel base, gelatinizing and forming into a certain shape and size by a suitable method.

[Preparation for Oro-Mucosal Application]

(1) Tablets for Oro-Mucosal Application

Tablets for oro-mucosal application are solid preparations having a certain form, and include troches/lozenges, sublingual tablets, buccal tablets, mucoadhesive tablets and medicated chewing gums. Preparations for oro-mucosal application are usually prepared according to said method of tablets. Troches/lozenges are tablets for oro-mucosal application, which are gradually dissolved or disintegrated in the mouth; Sublingual tablets are tablets for oro-mucosal application, from which active substances are quickly dissolved sublingually and absorbed via the oral mucosa; Buccal tablets are tablets for oro-mucosal applications, from which the active substances are dissolved gradually between the cheek and teeth, and absorbed via the oral mucosa; Mucoadhesive tablets are tablets for oro-mucosal application that are applied by adhesion to the oral mucosa; Medicated chewing gums are tablets for oro-mucosal application, releasing active substances by chewing.

(2) Spray for Oro-Mucosal Application

Spray for oro-mucosal application are preparation that are applied active substances by spraying into the oral cavity in mist, powder, foam or paste forms, and are usually prepared by dissolving or suspending active substances and suitable excipients in a solvent, filter, where necessary, and fill into a container together with liquefied or compressed gas, or dissolving or suspending active substances and suitable excipients in a solvent, and fill into a container, and fit with a pump for spraying.

(3) Semi-Solid Preparations for Oro-Mucosal Application

Semi-solid preparations for oro-mucosal application are preparation in cream, gel or ointment forms, intended for application to the oral mucosa. Semi-solid preparations for oro-mucosal application are usually prepared by emulsifying active substances together with excipients using purified water and oil component such as petrolatum, or by homogenizing active substances together with suitable excipients using polymer gel or oil and fats as the base. Creams are semi-solid preparations, which are in the form of oil-in-water or water-in-oil emulsions. Hydrophobic preparations in the form of water-in-oil emulsions may be termed "Oily creams". Creams are usually prepared by mixing homogeneously and emulsifying an oil-phase component and a water-phase component, both warmed, of which either one contains the active substances. These components have the following constituents. Oil-phase component: Vaseline, fatty alcohols, etc., with or without emulsifying agents or other suitable excipients. Water-phase component: purified water with or without emulsifying agents or other suitable excipients. Gels are gelatinous preparations. There are aqueous gels and oily gels. Aqueous gels are usually prepared by adding polymers, other excipients and purified water to active substances, dissolving or suspending, and gelatinizing by warming and cooling or by adding gelatinizing agents. Oily gels are usually prepared by adding liquid oily bases such as glycols, fatty alcohols and other excipients to active substances and mixing. Ointments are semi-solid preparations, which dissolve or disperse active substances in a base. There are two types, hydrophobic ointments and hydrophilic ointments. Hydrophobic ointments are usually prepared by warming to melt hydrophobic bases such as fatty oils, waxes or paraffin, adding and mixing active substances in the base to be dissolved or dispersed, and kneading the whole to make homogeneous. Hydrophilic ointments are usually prepared by warming to melt hydrophilic bases such as macrogol, adding and mixing active substances in the bases, and kneading the whole to make homogenous.

(4) Preparations for Gargle

Preparations for gargle are liquid preparations intended to apply locally to the oral and throat cavities. Solid type preparations to be dissolved in water before use are also included in this category. Preparations for gargle are usually prepared by dissolving active substances in a solvent together with suitable excipients, and filtering where necessary. Solid preparations are prepared according to said method of tablets or granules.

[Preparation for Injection]

(1) Injections

Injections are sterile preparations to be administered directly into the body through skin, muscle or blood vessel, usually in form of a solution, a suspension or an emulsion of active substances, or of a solid that contains active substances to be dissolved or suspended before use, and include freeze-dried injections, powders, prefilled syringes, cartridges, parenteral infusions, implants/pellets and prolonged-release injections besides generally called injections. Injections are prepared by the following method (a) and (b):
(a) Dissolve, suspend or emulsify active substances with or without excipients in water for injection or an aqueous or non-aqueous vehicle homogeneously, fill into containers for injection, seal, and sterilize.
(b) Dissolve, suspend or emulsify active substances with or without excipients in water for injection or an aqueous or non-aqueous vehicle, and filtrate aseptically, or prepare aseptically a homogeneous liquid, fill into containers for injection, and seal; Freeze-dried injections are usually prepared by dissolving active substances with or without excipients such as diluents in water for injection, sterilizing the solution by aseptic filtration, filling the filtrate directly into individual containers for injection and being freeze-dried, or dividing the filtrate in special containers, being freeze-dried and transferred into individual containers for injection. Powder for injections are usually prepared by filtrating aseptically a solution of active substances, obtaining powders by crystallization from the solution or mixing additionally the powders with sterilized excipients, and filling the powders into individual containers for injections. Prefilled syringes for injections are usually prepared by dissolving, suspending or emulsifying active substances with or without excipients in a vehicle, and filling into syringes. Cartridges are used by fixing in an injection device for exclusive use. Cartridges for injection are usually prepared by dissolving, suspending or emulsifying active substances with or without excipients in a vehicle, and filling into cartridges. Parenteral infusions are usually injections of not less than 100 mL, intended for intravenous administration. Implants/Pellets are solid or gel-like form injections, intended for subcutaneous or intramuscular administration by means of an implant device or operative treatment, for the purpose of releasing active substances for a long period of time. Implants/Pellets are usually prepared in a form of pellet, microsphere or gel using biodegradable polymers. Prolonged release injections are injections to be used for intramuscular administration, for the purpose of releasing active substances for a long period of time, and usually prepared by dissolving or suspending active substances in a non-aqueous vehicle such as vegetable oil, or by suspending microspheres prepared with biodegradable polymers.

[Preparations for Dialysis]

(1) Dialysis Agents

Dialysis agents are preparations in liquid, or in solid which are to be dissolved before use, intended for peritoneal dialysis or hemodialysis, and include peritoneal dialysis agents and hemodialysis agents. Peritoneal dialysis agents are sterile dialysis agents, intended to be used for peritoneal dialysis, and are usually prepared by dissolving active substances with suitable excipients in a vehicle to make a certain volume, or by filling active substances combined with suitable excipients in a container, and sealing it.

Sterilize if necessary. In the case of solid preparations to be dissolved before use, it can be prepared according to said preparation method of tablets or granules. Hemodialysis agents are dialysis agents to be used for hemodialysis, and are usually prepared by dissolving active substances with excipients in a vehicle to make a certain volume, or by filling active substances with excipients in a container. In the case of the solid preparations to be dissolved before use, it can be prepared according to said preparation method of tablets or granules.

[Preparation for Inhalation]

(1) Inhalations

Inhalations are preparations intended for administration as aerosols to the bronchial tubes or lung. Inhalations are classified to dry powder inhalers, inhalation liquid preparations and metered-dose inhalers. Dry powder inhalers are preparations which deliver a constant respiratory intake, intended for administration as solid particle aerosols, and are usually prepared by pulverizing active substances into fine particles. Where necessary, lactose or other suitable excipients are added to make homogeneous mixture. Inhalation liquid preparations are liquid inhalations which are administered by an inhalation device such as operating nebulizer. Inhalation liquid preparations are usually prepared by mixing active substances with a vehicle and suitable isotonic agents and/or pH adjusting agents to make a solution or suspension, and by filtering where necessary. Metered-dose inhalers are preparations which deliver a constant dose of active substances from the container together with propellant filled in. Metered-dose inhalers are usually prepared by dissolving active substances with a suitable dispersing agents and stabilizers in a vehicle to make a solution or suspension, and by filling in pressure-resistant containers together with liquid propellant, and setting metering valves.

[Preparation for Ophthalmic Application]

(1) Ophthalmic Liquids and Solutions

Ophthalmic liquids and solutions are sterile preparations of liquid, or solid to be dissolved or suspended before use, intended for application to the conjunctival sac or other ocular tissues. Ophthalmic liquids and solutions are usually prepared by dissolving, suspending active substances in a vehicle after adding excipients to make a constant volume, or mixing active substances and excipients, and filling into containers.

(2) Ophthalmic Ointments

Ophthalmic ointments are sterile preparations of semi-solid, intended for application to the conjunstival sac and other ocular tissues. Ophthalmic ointments are usually prepared by mixing homogeneously solution of or finely powdered active substances with petrolatum or other bases, and filling into containers.

[Preparation for Otic Application]

(1) Ear Preparation

Ear preparations are liquid, semi-solid, or solid preparations which are to be dissolved or suspended before use, intended for application to the external or internal ear. Ear preparations are usually prepared by filling in containers with liquids in which active substances and excipients are dissolved or suspended in a vehicle to make a constant volume, or with powders in which active substances and excipients are mixed.

[Preparations for Nasal Application]

(1) Nasal Preparations

Nasal preparations are preparations intended for application to the nasal cavities or nasal mucous membrane. Nasal preparations are classified into Nasal dry powder inhalers and Nasal liquid preparations. Nasal dry powder inhalers are fine powdered preparations, intended for application to the nasal cavities. Nasal dry powder inhalers are usually prepared by pulverizing active substances into moderately fine particles, or by mixing homogeneously with excipients where necessary. Nasal liquids and solutions are liquid preparations, or solid preparations to be dissolved or suspended before use, intended for application to the nasal cavities. Nasal liquids and solutions are usually prepared by dissolving or suspending active substances in a vehicle together with excipients, and filtering where necessary. Isotonic agents and/or pH adjusting agents may be used.

[Preparations for Rectal Application]

(1) Suppositories for Rectal Application

Suppositories for rectal application are semi-solid preparations of a desired shape and size, intended for intrarectal application, which release active substances by melting at body temperature or dissolving or dispersing gradually in the secretions. Suppositories for rectal application are usually prepared by mixing homogeneously active substances and excipients such as dispersing agents and emulsifying agents, dissolving or suspending uniformly in a base which is liquefied by warming, filling a constant volume of the resultant material into containers, and molding it into a shape and size. Lipophilic bases or hydrophilic bases are usually used.

(2) Semi-Solid Preparations for Rectal Application

Semi-solid preparations for rectal application are preparations which are in a form of cream, gel or ointment intended for application to around or inside of the anus. Semi-solid preparations for rectal application are usually prepared by emulsifying active substances with excipients in purified water and oil component such as Vaseline, or by homogeneously mixing active substances and excipients in a base of polymer gel or grease. Creams for rectal application are usually prepared by mixing homogeneously and emulsifying an oil-phase component (such as vaseline, fatty alcohols, etc.) and a water phase component (such as purified water with or without emulsifying agents or other suitable excipients), both warmed, of which either one contains the active substances. Gels for rectal application are gelatinous preparation. There are aqueous gels and oily gels. Aqueous gels are prepared adding polymers, other excipients and purified water to active substances, and dissolving or suspending, and gelatinizing by warming and cooling or by adding gelatinizing agents. Oily gels are prepared by adding liquid oily bases such as glycols, fatty alcohols and other excipients to active substances and mixing. Ointments for rectal application are semi-solid preparations, which dissolve or disperse active substances in a base. There are two types, hydrophobic ointment and hydrophilic ointments. Hydrophobic ointments are usually prepared by warming to melt hydrophobic bases such as fatty oils, waxes or paraffin, adding and mixing active substances in the bases to be dissolved or dispersed, and kneading the whole to make homogeneous. Hydrophilic ointments are usually prepared by warming to melt hydrophilic bases such as macrogol, adding and mixing active substances in the bases, and kneading the whole to make homogeneous.

(3) Enemas for Rectal Application

Enemas for rectal application are preparations in liquid form or viscous and gelatinous state, intended for applications via anus. Enemas for rectal application are preparations are usually prepared by dissolving or suspending active substances in purified water or suitable aqueous vehicle to make a given volume, and filling in containers. Dispersing agents, stabilizers and/or pH adjusting agents may be used.

[Preparations for Vaginal Application]

(1) Tablets for Vaginal Use

Tablets for vaginal use are solid preparations of a desired shapes and size, intended for application to the vagina, which release active substances by dissolving or dispersing gradually in the secretions. Tablets for vaginal use are usually prepared according to said preparation method of tablets.

(2) Suppositories for Vaginal Use

Suppositories for vaginal use are semi-solid preparations of a desired shapes and size, intended for application to the vagina, which release active substances by melting at body temperature or by dissolving or dispersing gradually in the secretions.

Suppositories for vaginal use are usually prepared according to said preparation method of suppositories for rectal applications.

[Preparation for Cutaneous Application]

(1) Solid Preparations for Cutaneous Application

Solid preparations for cutaneous application are solid preparations intended for application to the skin (including scalp) or nails. Powders for cutaneous application are included in this category. Powders for cutaneous application are powdery solid preparations intended for external application. Powders for cutaneous application are usually prepared by mixing homogeneously active substances and excipients such as diluents and pulverizing the mixture.

(2) Liquids and Solutions for Cutaneous Application

Liquids and solutions for cutaneous application are liquid preparations intended for application to the skin (including scalp) or nails. Liniments and lotions are included in this category. Liquids and solutions for cutaneous application are usually prepared by mixing active substances and excipients in a vehicle, and filtering if necessary. Liniments are liquid or muddy preparations intended for external application to the skin by rubbing. Lotions are external liquids in which active substances are dissolved, emulsified or finely dispersed in an aqueous vehicle. Lotions are usually prepared by dissolving, suspending or emulsifying active substances in purified water with excipients and making homogeneous as a whole.

(3) Spray for Cutaneous Application

Spray for cutaneous application are preparations intended for spraying active substances onto the skin in mists, powders, forms or paste state. Spray for cutaneous application are classified into aerosols for cutaneous application and pump sprays for cutaneous application. Spray for cutaneous applications are usually prepared by dissolving or suspending active substances in a vehicle, filtering where necessary, and filling in containers. Aerosols for cutaneous application are sprays which atomize active substances together with liquefied or compressed gas filled in containers. Aerosols for cutaneous application are usually prepared by dissolving or suspending active substances in a vehicle, filling with liquefied propellants in pressure-resistant containers, and setting a continuous spray valve. If necessary, dispersing agents and stabilizer may be used. Pump sprays for cutaneous application are sprays which atomize active substances in containers by pumping. Pump sprays for cutaneous application are usually prepared by dissolving or suspending active substances with excipients in a vehicle, filling in containers and setting pumps to the containers.

(4) Ointments

Ointments are semi-solid preparations to be applied to the skin, which dissolve or disperse active substances in a base. There are two types, hydrophobic ointments and hydrophilic ointments. Hydrophobic ointments are usually prepared by warming to melt hydrophobic bases such as fatty oils, waxes or paraffin, adding and mixing active substances in the base to be dissolved or dispersed, and Kneading the whole to make homogeneous. Hydrophilic ointments are usually prepared by warming to melt hydrophilic bases such as macrogol, adding and mixing active substances in the bases, and kneading the whole to make homogenous.

(5) Creams

Creams are semi-solid preparations to be applied to the skin, which are in the form of oil-in-water or water-in-oil emulsions. Hydrophobic preparations in the form of water-in-oil emulsions may be termed "Oily creams". Creams are usually prepared by mixing homogeneously and emulsifying an oil-phase component and a water-phase component, both warmed, of which either one contains the active substances. There components have the following constituents. Oil-phase component: Vaseline, fatty alcohols, etc., with or without emulsifying agents or other suitable excipients. Water-phase component: purified water with or without emulsifying agents or other suitable excipients.

(6) Gels

Gels are gelatinous preparations intended for application to the skin. There are aqueous gels and oily gels. Aqueous gels are usually prepared by adding polymers, other excipients and purified water to active substances, dissolving or suspending, and gelatinizing by warming and cooling or by adding gelatinizing agents. Oily gels are usually prepared by adding liquid oily bases such as glycols, fatty alcohols and other excipients to active substances and mixing.

(7) Patches

Patches are preparations intended to be attached on the skin. Patches are classified into Tapes/Plasters and Cataplasms/Gel patches. Patches are usually prepared by mixing active substances homogeneously with a base such as a polymer or a mixture of polymers, spreading on a backing layer or liner, and cutting into a given size. Percutaneous absorption type preparations may be prepared by using a release rate-controlling membrane. Where necessary, adhesive agents or penetration enhancers may be used. Tapes/Plasters are patches which are prepared with bases of practically no water contain. Tapes/Plasters are usually prepared by mixing homogeneously active substances with or without excipients and a base of non-water-soluble natural or synthetic polymers such as resins, plastics or rubber, and spreading on a cloth or spreading and sealing on a cloth or plastic film, cutting into a given size. The preparations may be also prepared by filling a mixture of active substances and a base with or without other excipients in releasers composed with a release-controlling film, supporter and liner. Cataplasms/Gels are patches using water containing bases. Cataplasms/Gels patches are usually prepared by mixing active substances, purified water, and glycerin or other liquid materials, or by mixing and kneading natural or synthetic polymers, which are soluble in water or absorbent of water, with purified water, adding active substances, mixing the whole homogeneously, spreading on a cloth or film, and cutting into a given size.

EXAMPLES

The present invention is described in details by referring to Examples hereinbelow, but the present invention is not limited to Examples.

Concerning chromatographic separation and TLC, a solvent in parentheses corresponds to an eluting solvent or a developing solvent employed and a ratio is expressed by volume ratio.

Concerning NMR, a solvent in parentheses corresponds to a solvent used for the measurement.

Silica gel column chromatography was performed by using Yamazen Automated Purification Equipment or Isco Combiflash Companion MPLC system.

HPLC preparative purification was performed under the following condition: [mobile phase (A): 0.1% trifluoroacetic acid aqueous solution; mobile phase (B): 0.1% trifluoroacetic acid-acetonitrile].

LC-MS/ELSD was performed under the following condition:
[column: Waters ACQUITY $C_{1\,8}$ (particle size: $1.7\times10^{-6}$ m; column length: 30×2.1 mm I.D.); flow rate: 1.0 mL/min; column temperature: 40° C.; mobile phase (A): 0.1% formic acid aqueous solution; mobile phase (B): 0.1% formic acid-acetonitrile solution; gradient (the ratio of mobile phase (A):mobile phase (B) is described): [0 min] 95:5; [0.1 min] 95:5; [1.2 min] 5:95; [1.4 mini] 5:95; [1.41 min] 95:5; [1.5 min] 95:5; Detector: UV(PDA), ELSD, MS].

A compound name used in the present specification was given by using a computer program ACD/Name (registered trademark) which generally denominates a compound according to the IUPAC nomenclature, by using Chemdraw Ultra (Version 12.0, supplied by Cambridge Soft) or by denominating according to the IUPAC nomenclature.

Reference Example 1: N-(1,3-dimethyl-1H-pyrazol-4-yl)formamide

To a solution of 1,3-dimethylpyrazol-4-amine hydrochloride (2 g) in formic acid (10.2 mL), sodium formate (1.84 g) was added, and the mixture was stirred at room temperature for 18 hours. To the reaction solution, a saturated sodium bicarbonate aqueous solution was added, and thereafter, the solution was extracted with ethyl acetate. The obtained organic layer was washed with water and a saturated saline solution. To the aqueous layer, sodium chloride was added, and the mixture was extracted with a mixed solution of dichloromethane and tetrahydrofuran. The organic layers were combined, and thereafter, were dried over anhydrous sodium sulfate, and were concentrated under a reduced pressure. The obtained residue was washed with methyl tert-butyl ether, and thereafter, was filtrated to give the title compound (1.41 g) having the following physical properties.

TLC: Rf 0.33 (ethyl acetate:methanol=20:1);
$^1$H-NMR (CDCl$_3$): δ 2.20-2.24, 3.81-3.83, 6.60-6.94, 7.86, 8.30.

Reference Example 2: 4,6-Dichloro-3-iodo-1H-pyrazolo[3,4-d]pyrimidine

To a solution of 4,6-dichloro-1H-pyrazolo[3,4-d]pyrimidine (5.0 g) in acetonitrile (265 mL)/N,N-dimethylformamide (50 mL), N-iodosuccinimide (7.74 g) was added and the mixture was stirred at 80° C. for 16 hours. To the reaction solution, acetic acid (0.5 mL) was added, and the solution was stirred for 9 hours. After acetonitrile was distilled off under a reduced pressure, the residue was diluted with ethyl acetate. To the solution, a small amount of hexane, water, and a sodium sulfite aqueous solution were added and the solution was stirred. To the obtained solution, water was added and the mixture was subjected to a liquid separation. The obtained organic layer was washed with water and a saline solution, and was dried over anhydrous sodium sulfate. To the obtained organic layer, a small amount of silica gel was added, and the mixture was stirred and was filtrated. The filtrate was concentrated under a reduced pressure to give the title compound (7.58 g) having the following physical properties.

TLC: Rf 0.36 (hexane:ethyl acetate=4:1);
$^1$H-NMR (DMSO-d$_6$): δ11.13.

Reference Example 3: 6-Chloro-3-iodo-N-(4-methoxybenzyl)-1H-pyrazolo[3,4-d]pyrimidin-4-amine To a suspended solution of the compound (6.5 g) prepared in Reference Example 2 in ethanol (50 mL), 4-methoxybenzylamine (2.97 mL) and diisopropylethylamine (7.14 mL) were added at 0° C., and the mixture was stirred at room temperature for 2 hours. The reaction solution was concentrated under a reduced pressure, and thereafter, ethyl acetate was added to the residue. The obtained solution was washed with water, a saturated sodium bicarbonate aqueous solution and a saturated saline solution. The obtained organic layer was dried over anhydrous sodium sulfate, and thereafter, was concentrated under a reduced pressure to give the title compound (6.5 g) having the following physical properties.

TLC: Rf 0.16 (hexane:ethyl acetate=4:1);
$^1$H-NMR (DMSO-d$_6$): δ3.76, 4.70-4.75, 6.92-6.98, 7.34-7.40, 7.51-7.59.

Reference Example 4: 6-Chloro-3-iodo-N-(4-methoxybenzyl)-1-(propan-2-yl)-1H-pyrazolo[3,4-d]pyrimidin-4-amine To a solution of triphenylphosphine (3.91 g) in tetrahydrofuran (50 mL), diisopropyl azodicarboxylate (1.9 mol/L, 5.9 mL) was added at 0° C., and the mixture was stirred for 10 minutes. To the reaction solution, isopropanol (0.86 mL) was added, and the solution was stirred at 0° C. for 10 minutes. To the reaction solution, the compound (3.1 g) prepared in Reference Example 3 was added, and the mixture was stirred at room temperature for 16 hours. The reaction solution was concentrated under a reduced pressure, and thereafter, the obtained residue was purified by silica gel column chromatography to give the title compound (3.0 g) having the following physical properties.

TLC: Rf 0.51 (hexane:ethyl acetate=4:1);
$^1$H-NMR (CDCl$_3$): δ1.47-1.53, 3.82, 4.75-4.78, 4.97-5.09, 6.42-6.52, 6.89-6.95, 7.30-7.36.

Reference Example 5: 6-Chloro-3-iodo-1-(propan-2-yl)-1H-pyrazolo[3,4-d]pyrimidin-4-amine The compound (3.0 g) prepared in Reference Example 4 was dissolved in trifluoroacetic acid (9.8 mL), and the solution was stirred at 60° C. for 16 hours. The reaction solution was concentrated under a reduced pressure, and thereafter, was azeotroped with toluene. The residue was neutralized with 2 N sodium hydroxide aqueous solution, and the mixture was extracted with ethyl acetate. The obtained organic layer was washed with a saturated saline solution, and thereafter, was dried over anhydrous sodium sulfate. The organic layer was concentrated under a reduced pressure, and thereafter, the residue was washed with methyl tert-butyl ether. The obtained solid was taken by filtering to give the title compound (1.9 g) having the following physical properties.

TLC: Rf 0.26 (hexane:ethyl acetate=4:1);
$^1$H-NMR (CDCl$_3$): δ1.48-1.56, 4.99-5.09, 5.75-6.10.

Reference Example 6: 3-Iodo-6-(methylsulfanyl)-1-(propan-2-yl)-1H-pyrazolo[3,4-d]pyrimidin-4-amine To a solution of the compound (1.9 g) prepared in Reference Example 5 in dimethylsulfoxide (50 mL), sodium thiomethoxide (473 mg) was added, and the mixture was stirred at room temperature for 3 hours. To the reaction solution, water was added, and the mixture was extracted with ethyl acetate. The obtained organic layer was washed with water and a saturated saline solution, and was dried over anhydrous sodium sulfate. The solvent was distilled off under a reduced pressure to give the title compound (1.9 g) having the following physical properties.

TLC: Rf 0.29 (hexane:ethyl acetate=4:1);
$^1$H-NMR (CDCl$_3$): δ1.48-1.55, 2.56, 4.97-5.09, 5.63-5.81.

Reference Example 7: 3-Iodo-6-(methylsulfonyl)-1-(propan-2-yl)-1H-pyrazolo[3,4-d]pyrimidin-4-amine To a solution of the compound (1.97 g) prepared in Reference Example 6 in acetonitrile (50 mL), ammonium molybdate tetrahydrate (348 mg) and hydrogen peroxide water (30% aqueous solution, 3.16 mL) were added at 0° C., and the mixture was stirred at room temperature for 18 hours. The reaction solution was diluted with ethyl acetate, and thereafter, was washed with water, and a saturated saline solution. The obtained organic layer was dried over anhydrous sodium sulfate, and was concentrated under a reduced pressure. The residue was washed with methyl tert-butyl ether, and thereafter, the solid was taken by filtering to give the title compound (1.62 g) having the following physical properties.

TLC: Rf 0.23 (hexane:ethyl acetate=1:1);

$^1$H-NMR (CDCl$_3$): δ1.53-1.60, 3.33, 5.05-5.20, 6.10-6.45.

Reference Example 8: $N^6$-(1,3-dimethyl-1H-pyrazol-4-yl)-3-iodo-1-(propan-2-yl)-1H-pyrazolo[3,4-d]pyrimidine-4,6-diamine To a solution of the compound (1.62 g) prepared in Reference Example 7 in N,N-dimethylformamide (43 mL), the compound (1.18 g) prepared in Reference Example 1 and sodium tert-butoxide (817 mg) were added at 0° C., and the mixture was stirred at 60° C. for 16 hours. To the reaction solution, 2 N sodium hydroxide aqueous solution (21.2 mL) was added, and the solution was stirred at room temperature for 1 hour. The reaction solution was neutralized with 1 N hydrochloric acid, and thereafter, was extracted with ethyl acetate. The obtained organic layer was washed with a saturated saline solution, and was dried over anhydrous sodium sulfate. The solvent was distilled off under a reduced pressure, and the residue was purified by silica gel column chromatography to give the title compound (1.2 g) having the following physical properties.

TLC: Rf 0.43 (ethyl acetate);

$^1$H-NMR (CDCl$_3$): δ1.49-1.55, 2.24, 3.86, 4.82-4.95, 5.47-5.62, 6.33, 7.81.

Reference Example 9: 3-{1-[tert-Butyl(dimethyl)silyl]-1H-indol-5-yl}-$N^6$-(1,3-dimethyl-1H-pyrazol-4-yl)-1-(propan-2-yl)-1H-pyrazolo[3,4-d]pyrimidine-4,6-diamine To a solution of the compound (250 mg) prepared in Reference Example 8 in dimethylacetamide (5 mL), tripotassium phosphate (0.61 mL, 2 M aqueous solution) and 1-(tert-butyldimethylsilyl)-1H-indol-5-ylboronic acid (CAS No. 913835-68-4) (200 mg) were added. The reaction solution was deaerated, and thereafter, to the solution, chloro(2-dicyclohexylphosphino-2',4',6'-triisopropyl-1,1'-biphenyl)[2-(2'-amino-1,1'-biphenyl)]palladium(II) (a second generation XPhos precatalyst, CAS No. 1310584-14-5) (38 mg) was added under an argon atmosphere and the mixture was stirred at 80° C. for 2 hours. The reaction solution was diluted with ethyl acetate, and was washed with water, and a saturated saline solution. The obtained organic layer was dried over anhydrous sodium sulfate, and was concentrated under a reduced pressure. The residue was purified by silica gel column chromatography to give the title compound (250 mg) having the following physical properties.

TLC: Rf 0.25 (ethyl acetate);

$^1$H-NMR (CDCl$_3$): δ0.09-0.12, 0.88-0.94, 1.55-1.63, 2.27, 3.87, 4.96-5.04, 5.18-5.24, 6.32, 6.60-6.64, 7.26-7.30, 7.51-7.53, 7.90-7.96.

Example 1: $N^6$-(1,3-dimethyl-1H-pyrazol-4-yl)-3-(1H-indol-5-yl)-1-isopropyl-1H-pyrazolo[3,4-d]pyrimidine-4,6-diamine

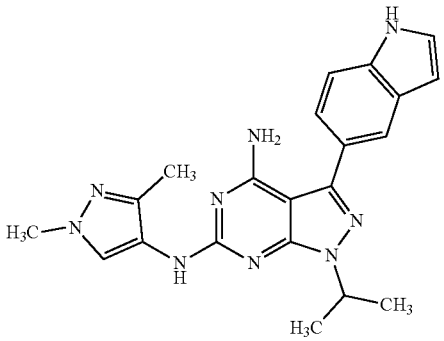 [SMILES: Cc1nn(C)cc1Nc1nc(N)c2c(-c3ccc4[nH]ccc4c3)nn(C(C)C)c2n1]

To a solution of the compound (250 mg) prepared in Reference Example 9 in tetrahydrofuran (5 mL), tetra-n-butylammonium fluoride (0.97 mL, 1 M tetrahydrofuran solution) was added, and the mixture was stirred at room temperature for 2 hours. The reaction solution was diluted with ethyl acetate, and was washed with a saturated ammonium chloride aqueous solution and a saturated saline solution. The obtained organic layer was dried over anhydrous sodium sulfate, and was concentrated under a reduced pressure. The residue was purified by silica gel column chromatography to give the compound of the present invention (115 mg) having the following physical properties.

TLC: Rf 0.41 (ethyl acetate:methanol=10:1);

$^1$H-NMR (CDCl$_3$): δ1.58-1.64, 2.26, 3.87, 4.95-5.05, 5.18-5.26, 6.34, 6.61-6.64, 7.25-7.30, 7.51, 7.90-7.95, 8.34.

Reference Example 10: 4-Bromo-7-fluoro-1-(tetrahydro-2H-pyran-2-yl)-1H-indazole

To a solution of 4-bromo-7-fluoro-1H-indazole (918 mg) in methylene chloride (14 mL), 3,4-dihydro-2H-pyran (1.56 mL) and p-toluenesulfonic acid monohydrate (81 mg) were added, and the mixture was stirred at 40° C. for 1.5 hours. To the reaction solution, a saturated sodium bicarbonate aqueous solution was added, and the solution was extracted with ethyl acetate. The obtained organic layer was washed with a saturated saline solution, and thereafter, was dried over anhydrous sodium sulfate, and was concentrated under a reduced pressure. The residue was purified by silica gel column chromatography to give the title compound (1.24 g) having the following physical properties.

TLC: Rf 0.61 (hexane:ethyl acetate=5:1);

$^1$H-NMR (CDCl$_3$): δ 1.48-1.82, 2.03-2.23, 2.51-2.68, 3.69-3.80, 4.00-4.08, 5.83-5.90, 6.91-7.00, 7.17-7.23, 8.03-8.06.

Reference Example 11: [7-Fluoro-1-(tetrahydro-2H-pyran-2-yl)-1H-indazol-4-yl]boronic acid Under a nitrogen atmosphere, the compound (1.24 g) prepared in Reference Example 10 and triisopropylborate (3.8 mL) were dissolved in tetrahydrofuran (16.6 mL), and the solution was cooled to −78° C. To the solution, n-butyllithium (8.02 mL, 1.55 M/hexane) was added dropwise, and thereafter, the solution was stirred at −40° C. for 1 hour. To the reaction solution, water was added, and the organic layer was back-extracted with 0.5 N sodium hydroxide aqueous solution. To the obtained aqueous layer, ammonium acetate (1.39 g) was added, and the mixture was stirred at room temperature for 30 minutes. The reaction solution was cooled to 0° C., and thereafter, to the solution, sodium dihydrogenphosphate was added, and the pH was adjusted to 4 to 5. The precipitated solid was taken by filtering, and thereafter, was washed with cold water. The obtained solid was dried to give the compound of the present invention (710 mg) having the following physical properties.

TLC: Rf 0.34 (hexane:ethyl acetate=2:1);

$^1$H-NMR (DMSO-d$_6$): δ 1.47-1.60, 1.63-1.82, 1.97-2.10, 2.35-2.54, 3.58-3.69, 3.83-3.94, 5.79-5.85, 7.18-7.27, 7.58-7.64, 8.27, 8.34-8.37.

Reference Example 12: $N^6$-(1,3-dimethyl-1H-pyrazol-4-yl)-3-[7-fluoro-1-(tetrahydro-2H-pyran-2-yl)-1H-indazol-4-yl]-1-(propan-2-yl)-1H-pyrazolo[3,4-d]pyrimidine-4,6-diamine A similar procedure to Reference Example 9 was carried out by using the compound prepared in Reference Example 11 instead of 1-(tert-butyldimethylsilyl)-1H-indol-5-ylboronic acid to give the title compound having the following physical properties.

TLC: Rf 0.51 (ethyl acetate, NH silica);

$^1$H-NMR (CDCl$_3$): δ1.54-1.64, 1.72-1.83, 2.06-2.23, 2.26, 2.55-2.70, 3.73-3.83, 3.88, 4.03-4.12, 4.98-5.16, 5.92-5.98, 6.34, 7.16-7.23, 7.31-7.36, 7.88, 8.25-8.26.

Example 2: $N^6$-(1,3-dimethyl-1H-pyrazol-4-yl)-3-(7-fluoro-1H-indazol-4-yl)-1-isopropyl-1H-pyrazolo[3,4-d]pyrimidine-4,6-diamine

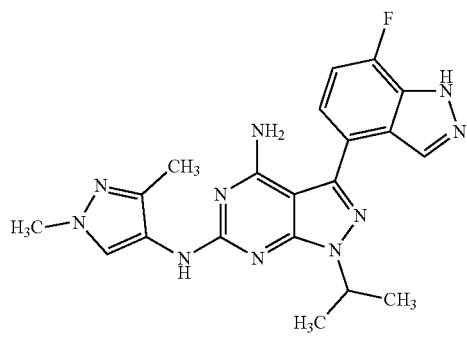 [SMILES: Cc1nn(C)cc1Nc1nc(N)c2c(-c3ccc(F)c4[nH]ncc34)nn(C(C)C)c2n1]

To a solution of the compound (61 mg) prepared in Reference Example 12 in dichloromethane (1 mL), trifluoroacetic acid (0.9 mL) was added at room temperature, and the mixture was stirred for 3 hours. To the reaction solution, a saturated sodium bicarbonate aqueous solution was added, and the solution was extracted with ethyl acetate. The obtained organic layer was washed with a saturated saline solution, and thereafter, was dried over anhydrous sodium sulfate, and was concentrated under a reduced pressure. The residue was purified by silica gel column chromatography to give the compound of the present invention (34 mg) having the following physical properties.

TLC: Rf 0.27 (ethyl acetate, NH silica);

$^1$H-NMR (CDCl$_3$): δ1.60-1.66, 2.27, 3.88, 5.00-5.09, 5.12-5.22, 6.39, 7.17-7.25, 7.34-7.40, 7.90, 8.33-8.36.

Example 3: 3-(2,3-Dihydro-1-benzofuran-5-yl)-$N^6$-(1,3-dimethyl-1H-pyrazol-4-yl)-1-isopropyl-1H-pyrazolo[3,4-d]pyrimidine-4,6-diamine

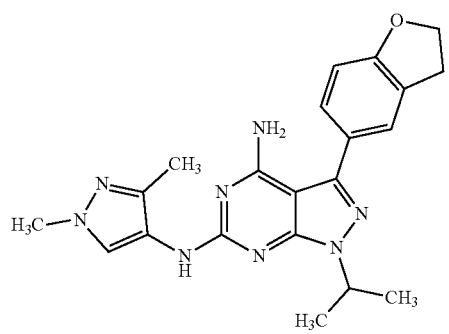 [SMILES: Cc1nn(C)cc1Nc1nc(N)c2c(-c3ccc4c(c3)CCO4)nn(C(C)C)c2n1]

A similar procedure to Reference Example 9 was carried out by using 2,3-dihydrobenzofuran-5-boronic acid instead of 1-(tert-butyldimethylsilyl)-1H-indol-5-ylboronic acid to give the compound of the present invention having the following physical properties.

$^1$H-NMR (DMSO-d$_6$): δ1.41-1.46, 2.12, 3.24-3.30, 3.73, 4.57-4.62, 4.84-4.92, 6.10-6.40, 6.87-6.90, 7.32-7.36, 7.48, 7.93, 8.15.

Purity (LC-MS/ELSD): 99.3% (Retention time: 0.77 minutes);

MASS (ESI, Pos.): 405 (M+H)$^+$.

Reference Example 13: $N^6$-[2-fluoro-4-(methylsulfonyl)phenyl]-3-iodo-1-(propan-2-yl)-1H-pyrazolo[3,4-d]pyrimidine-4,6-diamine A similar procedure to Reference Example 1→Reference Example 8 was carried out by using 2-fluoro-4-(methylsulfonyl)aniline instead of 1,3-dimethylpyrazol-4-amine hydrochloride to give the title compound having the following physical properties.

TLC: Rf 0.34 (hexane:ethyl acetate=1:1);

$^1$H-NMR (CDCl$_3$): δ1.54-1.62, 3.05, 4.89-5.03, 5.58-5.82, 7.37-7.43, 7.63-7.69, 7.75-7.79, 8.89-8.97.

Examples 4-1 to 4-4

A similar procedure to Reference Example 9→Example 2 was carried out by using the compound prepared in Reference Example 13 instead of the compound prepared in Reference Example 8, and using a corresponding boronic acid instead of 1-(tert-butyldimethylsilyl)-1H-indol-5-ylboronic acid to give the compound of the present invention having the following physical properties.

Example 4-1: 3-(7-Chloro-1H-indazol-4-yl)-N⁶-[2-fluoro-4-(methylsulfonyl)phenyl]-1-isopropyl-1H-pyrazolo[3,4-d]pyrimidine-4,6-diamine

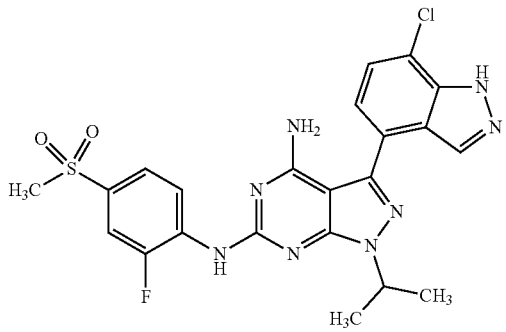 [SMILES: CC(C)n1nc(-c2ccc(Cl)c3[nH]ncc23)c2c(N)nc(Nc3ccc(S(C)(=O)=O)cc3F)nc21]

TLC: Rf 0.55 (hexane:ethyl acetate=1:2);
¹H-NMR (DMSO-d₆): δ1.49-1.60, 3.23, 4.97-5.06, 6.38-7.15, 7.31-7.35, 7.56-7.61, 7.68-7.79, 8.25, 8.66-8.73, 8.86, 13.74.

Example 4-2: N⁶-[2-fluoro-4-(methylsulfonyl)phenyl]-3-(1H-indazol-4-yl)-1-isopropyl-1H-pyrazolo[3,4-d]pyrimidine-4,6-diamine

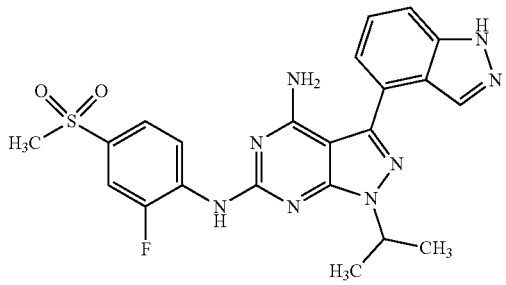 [SMILES: CC(C)n1nc(-c2cccc3[nH]ncc23)c2c(N)nc(Nc3ccc(S(C)(=O)=O)cc3F)nc21]

TLC: Rf 0.43 (hexane:ethyl acetate=1:2);
¹H-NMR (CDCl₃): δ1.65-1.71, 3.08, 5.08-5.20, 5.32-5.42, 7.42-7.47, 7.51-7.62, 7.65-7.71, 7.77-7.82, 8.33, 9.01-9.08.

Example 4-3: 3-(7-Fluoro-1H-indazol-4-yl)-N⁶-[2-fluoro-4-(methylsulfonyl)phenyl]-1-isopropyl-1H-pyrazolo[3,4-d]pyrimidine-4,6-diamine

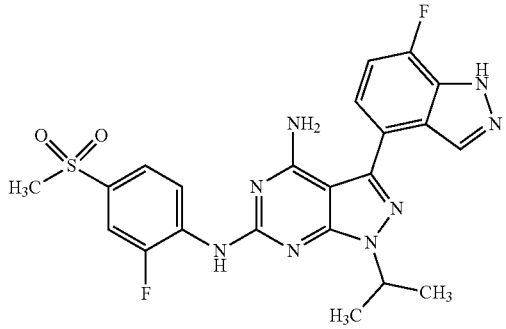 [SMILES: CC(C)n1nc(-c2ccc(F)c3[nH]ncc23)c2c(N)nc(Nc3ccc(S(C)(=O)=O)cc3F)nc21]

TLC: Rf 0.48 (hexane:ethyl acetate=1:2);
¹H-NMR (CDCl₃): δ1.63-1.71, 3.08, 5.04-5.20, 5.27-5.40, 7.20-7.25, 7.35-7.40, 7.41-7.43, 7.66-7.71, 7.79-7.85, 8.34-8.36, 9.00-9.07, 10.35-10.50.

Example 4-4: 4-(4-Amino-6-{[2-fluoro-4-(methylsulfonyl)phenyl]amino}-1-isopropyl-1H-pyrazolo[3,4-d]pyrimidin-3-yl)-1H-indazole-7-carbonitrile

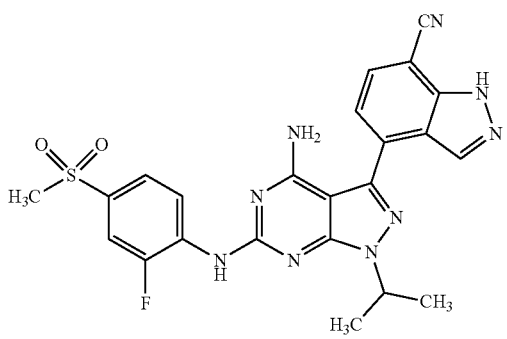 [SMILES: CC(C)n1nc(-c2ccc(C#N)c3[nH]ncc23)c2c(N)nc(Nc3ccc(S(C)(=O)=O)cc3F)nc21]

TLC: Rf 0.44 (hexane:ethyl acetate=1:2);
¹H-NMR (DMSO-s): δ1.48-1.60, 3.22, 4.98-5.10, 7.44-7.48, 7.63-7.70, 8.02-8.07, 8.35, 8.63-8.70, 8.90, 14.13.

Examples 5-1 to 5-5

A similar procedure to Reference Example 1→Reference Example 8→Reference Example 9→Example 2 was carried out by using a corresponding amine compound instead of 1,3-dimethylpyrazol-4-amine hydrochloride and using a corresponding boronic acid instead of 1-(tert-butyldimethylsilyl)-1H-indol-5-ylboronic acid to give the compound of the present invention having the following physical properties. In Example 5-5, HPLC preparative purification was performed instead of silica gel column chromatography in Example 2.

Example 5-1: 3-(7-Fluoro-1H-indazol-4-yl)-1-isopropyl-N⁶-{3-methyl-1-[(methylsulfonyl)methyl]-1H-pyrazol-4-yl}-1H-pyrazolo[3,4-d]pyrimidine-4,6-diamine

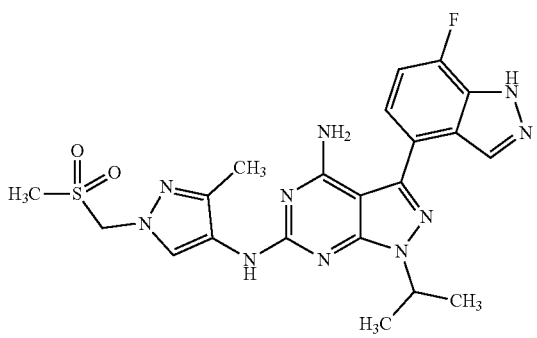 [SMILES: Cc1nn(CS(C)(=O)=O)cc1Nc1nc(N)c2c(-c3ccc(F)c4[nH]ncc34)nn(C(C)C)c2n1]

TLC: Rf 0.27 (ethyl acetate);
¹H-NMR (CDCl₃): δ1.60-1.66, 2.31, 2.90, 5.00-5.12, 5.24-5.36, 6.61, 7.17-7.25, 7.34-7.40, 8.30-8.36.

Example 5-2: 3-(7-Fluoro-1H-indazol-4-yl)-1-isopropyl-N⁶-[2-methoxy-4-(methylsulfonyl)phenyl]-1H-pyrazolo[3,4-d]pyrimidine-4,6-diamine

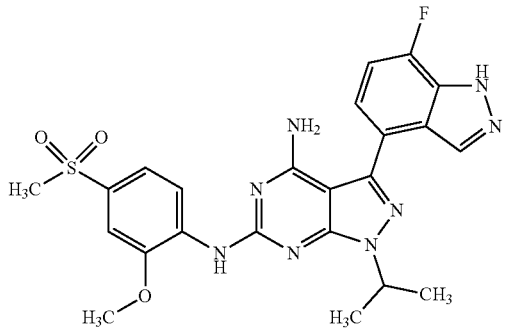 [SMILES: COc1cc(S(C)(=O)=O)ccc1Nc1nc(N)c2c(-c3ccc(F)c4[nH]ncc34)nn(C(C)C)c2n1]

TLC: Rf 0.33 (hexane:ethyl acetate=1:2);
¹H-NMR (CD3 OD): δ1.60-1.65, 3.13, 4.06, 5.06-5.21, 7.24-7.31, 7.35-7.38, 7.49, 7.58-7.63, 8.21-8.23, 8.98-9.01.

Example 5-3: N⁶-[4-(cyclopropylsulfonyl)-2-fluorophenyl]-3-(1H-indazol-4-yl)-1-isopropyl-1H-pyrazolo[3,4-d]pyrimidine-4,6-diamine ¹H-NMR (DMSO-$d_6$): δ1.04-1.06, 1.12-1.15, 1.53-1.55, 2.85-2.92, 5.00-5.06, 7.34-7.36, 7.48-7.52, 7.62-7.75, 8.16, 8.70-8.75, 8.82, 13.24.
Purity (LC-MS/ELSD): 100% (Retention time: 0.92 minutes);
MASS (ESI, Pos.): 507 (M+H)⁺.

Example 5-4: N⁶-(3-chloro-1-methyl-1H-pyrazol-4-yl)-3-(7-fluoro-1H-indazol-4-yl)-1-isopropyl-1H-pyrazolo[3,4-d]pyrimidine-4,6-diamine TLC: Rf 0.42 (hexane:ethyl acetate=1:2);
¹H-NMR (CDCl₃): δ1.62-1.68, 3.92, 5.00-5.15, 5.20-5.32, 6.64-6.71, 7.18-7.25, 7.35-7.40, 8.09, 8.34-8.37.

Example 5-5: 1-(4-{[4-Amino-3-(7-fluoro-1H-indazol-4-yl)-1-isopropyl-1H-pyrazolo[3,4-d]pyrimidin-6-yl]amino}-3-fluorophenyl)ethanone di(trifluoroacetate)

¹H-NMR (CD3 OD): δ1.61-1.65, 2.59, 5.09-5.19, 7.26-7.31, 7.36-7.40, 7.75-7.79, 7.88-7.91, 8.22-8.23, 8.86-8.92.
Purity (LC-MS/ELSD): 93.2% (Retention time: 0.95 minutes);
MASS (ESI, Pos.): 463 (M+H)⁺.

Examples 6-1 to 6-9

A similar procedure to Reference Example 1→Reference Example 8→Reference Example 9→Example 1 was carried out by using a corresponding amine compound instead of 1,3-dimethylpyrazol-4-amine hydrochloride and using a corresponding boronic acid instead of 1-(tert-butyldimethylsilyl)-1H-indol-5-ylboronic acid to give the compound of the present invention having the following physical properties. In Examples 6-4 to 6-9, HPLC preparative purification was performed instead of silica gel column chromatography in Example 1.

Example 6-1: 3-(1H-indol-5-yl)-1-isopropyl-N⁶-(3-methyl-1H-pyrazol-4-yl)-1H-pyrazolo[3,4-d]pyrimidine-4,6-diamine

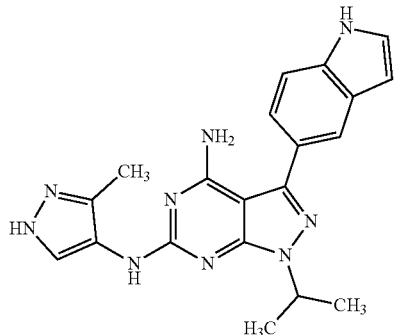

TLC: Rf 0.35 (hexane:ethyl acetate=1:3);
¹H-NMR (CDCl₃): δ1.56-1.62, 2.31, 4.95-5.08, 5.23-5.37, 6.39, 6.61-6.64, 7.27-7.31, 7.48-7.53, 7.94, 8.10, 8.28-8.35.

Example 6-2: N⁶-[1-(difluoromethyl)-3-methyl-1H-pyrazol-4-yl]-3-(1H-indol-5-yl)-1-isopropyl-1H-pyrazolo[3,4-d]pyrimidine-4,6-diamine

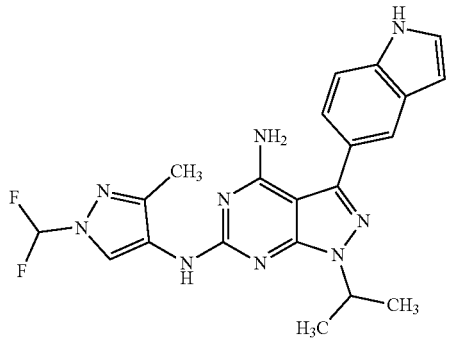 [SMILES: Cc1nn(C(F)F)cc1Nc1nc(N)c2c(-c3ccc4[nH]ccc4c3)nn(C(C)C)c2n1]

TLC: Rf 0.26 (hexane:ethyl acetate=1:1);
¹H-NMR (CDCl₃): δ1.60-1.65, 2.32, 4.95-5.05, 5.23-5.31, 6.42, 6.62-6.65, 6.90-7.33, 7.50-7.54, 7.95, 8.28-8.34, 8.44.

Example 6-3: N⁶-(1,3-dimethyl-1H-pyrazol-5-yl)-3-(1H-indol-5-yl)-1-isopropyl-1H-pyrazolo[3,4-d]pyrimidine-4,6-diamine TLC: Rf 0.40 (hexane:ethyl acetate=1:3);
¹H-NMR (CDCl₃): δ1.55-1.61, 2.28, 3.74, 4.92-5.04, 5.27-5.37, 6.15, 6.55-6.66, 7.27-7.31, 7.47-7.54, 7.93, 8.26-8.34.

Example 6-4: 3-(1H-indol-5-yl)-1-isopropyl-N⁶-(5-pyrimidinyl)-1H-pyrazolo[3,4-d]pyrimidine-4,6-diamine trifluoroacetate Purity (LC-MS/ELSD): 85.0% (Retention time: 0.76 minutes);
MASS (ESI, Pos.): 386 (M+H)⁺.

Example 6-5: 3-(1H-indol-5-yl)-1-isopropyl-$N^6$-(6-methoxy-3-pyridinyl)-1H-pyrazolo[3,4-d]pyrimidine-4,6-diamine trifluoroacetate Purity (LC-MS/ELSD): 96.4% (Retention time: 0.85 minutes);
MASS (ESI, Pos.): 415 (M+H)$^+$.

Example 6-6: 5-{[4-Amino-3-(1H-indol-5-yl)-1-isopropyl-1H-pyrazolo[3,4-d]pyrimidin-6-yl]amino}-N,N-dimethyl-2-pyrimidinecarboxamide trifluoroacetate Purity (LC-MS/ELSD): 99.4% (Retention time: 0.76 minutes);
MASS (ESI, Pos.): 457 (M+H)$^+$.

Example 6-7: $N^6$-{4-[2-(dimethylamino)ethoxy]-2-fluorophenyl}-3-(1H-indol-5-yl)-1-isopropyl-1H-pyrazolo[3,4-d]pyrimidine-4,6-diamine di(trifluoroacetate)

Purity (LC-MS/ELSD): 99.9% (Retention time: 0.66 minutes);
MASS (ESI, Pos.): 489 (M+H)*.

Example 6-8: $N^6$-[2-fluoro-(4-morpholinylmethyl)phenyl]-3-(1H-indol-5-yl)-1-isopropyl-1H-pyrazolo[3,4-d]pyrimidine-4,6-diamine di(trifluoroacetate)

Purity (LC-MS/ELSD): 99.5% (Retention time: 0.68 minutes);
MASS (ESI, Pos.): 501 (M+H)$^+$.

Example 6-9: 5-{[4-Amino-3-(1H-indol-5-yl)-1-isopropyl-1H-pyrazolo[3,4-d]pyrimidin-6-yl]amino}-1-indanone trifluoroacetate Purity (LC-MS/ELSD): 100% (Retention time: 0.89 minutes);
MASS (ESI, Pos.): 438 (M+H)$^+$.

Example 7: 3-(6-Amino-5-methoxy-3-pyridinyl)-$N^6$-[2-fluoro-4-(methylsulfonyl)phenyl]-1-isopropyl-1H-pyrazolo[3,4-d]pyrimidine-4,6-diamine

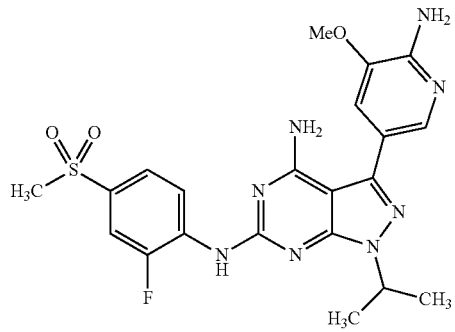 [SMILES: COc1cc(-c2nn(C(C)C)c3nc(Nc4ccc(S(C)(=O)=O)cc4F)nc(N)c23)cnc1N]

A similar procedure to Reference Example 9 was carried out by using the compound prepared in Reference Example 13 instead of the compound prepared in Reference Example 8 and using 6-amino-5-methoxypyridine-3-boronic acid pinacol ester instead of 1-(tert-butyldimethylsilyl)-1H-indol-5-ylboronic acid to give the compound of the present invention having the following physical properties.

TLC: Rf 0.25 (hexane:ethyl acetate=1:2);
$^1$H-NMR (CDCl$_3$): δ1.59-1.64, 3.06, 3.94, 4.86-4.94, 4.97-5.11, 5.36-5.42, 7.23-7.26, 7.39-7.43, 7.62-7.69, 7.72-7.80, 7.95-7.97, 8.98-9.05.

Example 8: 3-(1-Benzofuran-5-yl)-$N^6$-(1,3-dimethyl-1H-pyrazol-4-yl)-1-(2,2,2-trifluoroethyl)-1H-pyrazolo[3,4-d]pyrimidine-4,6-diamine di(trifluoroacetate)

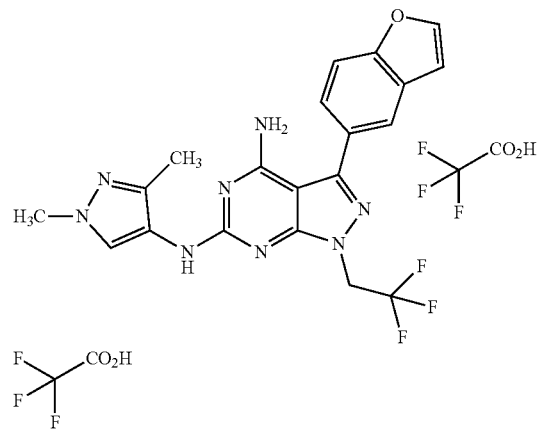

A similar procedure to Reference Example 4→Reference Example 5→Reference Example 6→Reference Example 7→Reference Example 8→Reference Example 9 was carried out by using 2,2,2-trifluoroethanol instead of isopropanol and using benzofuran-5-boronic acid instead of 1-(tert-butyldimethylsilyl)-1H-indol-5-ylboronic acid to give the compound of the present invention having the following physical properties. Meanwhile, HPLC preparative purification was performed instead of silica gel column chromatography in Reference Example 9.

$^1$H-NMR (DMSO-d$_6$): δ2.13, 3.74, 5.02-5.13, 6.25-6.70, 7.07-7.08, 7.57-7.59, 7.74-7.76, 7.92, 7.99, 8.08-8.09, 8.45.
Purity (LC-MS/ELSD): 99.7% (Retention time: 0.85 minutes);
MASS (ESI, Pos.): 443 (M+H)$^+$.

Example 9: $N^6$-(1,3-dimethyl-1H-pyrazol-4-yl)-3-(7-fluoro-1H-indazol-4-yl)-1-(3-oxetanyl)-1H-pyrazolo[3,4-d]pyrimidine-4,6-diamine

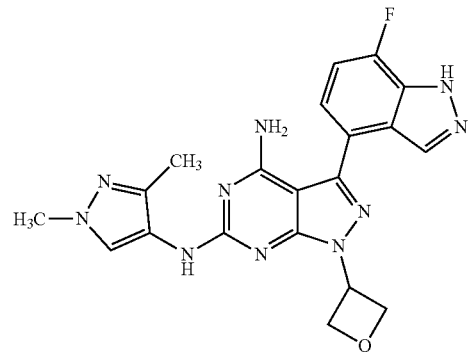 [SMILES: Cc1nn(C)cc1Nc1nc(N)c2c(-c3ccc(F)c4[nH]ncc34)nn(C3COC3)c2n1]

A similar procedure to Reference Example 4→Reference Example 5→Reference Example 6→Reference Example 7→Reference Example 8→Reference Example 9→Example 2 was carried out by using oxetan-3-ol instead of isopropanol and using the boronic acid prepared in Reference Example 11 instead of 1-(tert-butyldimethylsilyl)-1H-indol-5-ylboronic acid to give the compound of the present invention having the following physical properties.

$^1$H-NMR (DMSO-$d_6$): δ2.13, 3.76, 4.98-5.02, 5.12-5.16, 5.89-5.96, 6.30-6.80, 7.30-7.37, 8.03, 8.29-8.31, 8.45, 13.85.

Purity (LC-MS/ELSD): 99.0% (Retention time: 0.61 minutes);

MASS (ESI, Pos.): 435 (M+H)$^+$.

Example 10: 1-Cyclobutyl-$N^6$-(1,3-dimethyl-1H-pyrazol-4-yl)-3-(1H-indol-6-yl)-1H-pyrazolo[3,4-d]pyrimidine-4,6-diamine trifluoroacetate

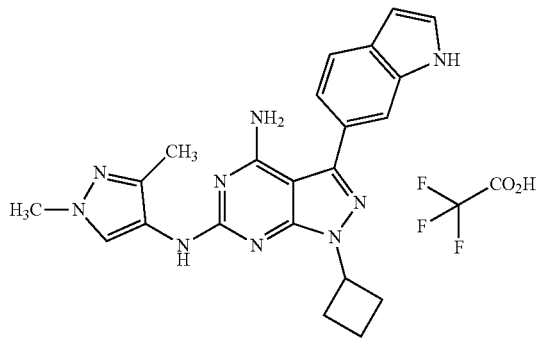 [SMILES: Cc1nn(C)cc1Nc1nc(N)c2c(-c3ccc4cc[nH]c4c3)nn(C3CCC3)c2n1 ; O=C(O)C(F)(F)F]

A similar procedure to Reference Example 4→Reference Example 5→Reference Example 6→Reference Example 7→Reference Example 8→Reference Example 9→Example 1 was carried out by using cyclobutanol instead of isopropanol and using 1-(tert-butyldimethylsilyl)-1H-indol-6-ylboronic acid instead of 1-(tert-butyldimethylsilyl)-1H-indol-5-ylboronic acid to give the compound of the present invention having the following physical properties. Meanwhile, HPLC preparative purification was performed instead of silica gel column chromatography in Example 1.

$^1$H-NMR (DMSO-$d_6$): δ1.83-1.90, 2.13, 2.36-2.41, 2.65-2.73, 3.76, 5.14-5.22, 6.51-6.52, 7.29-7.31, 7.44-7.46, 7.67-7.70, 7.96, 8.25-8.50, 11.27.

Purity (LC-MS/ELSD): 96.2% (Retention time: 0.81 minutes);

MASS (ESI, Pos.): 414 (M+H)$^+$.

Reference Example 14: 1-tert-Butyl-6-chloro-N-(4-methoxybenzyl)-1H-pyrazolo[3,4-d]pyrimidin-4-amine To a solution of 2,4,6-trichloropyrimidine-5-carbaldehyde (1.1 g) in ethanol (25 mL), a suspension of t-butylhydrazine hydrochloride (620 mg) in ethanol (10 mL) and triethylamine (3.3 mL) were added slowly at −78° C., and the mixture was stirred at −78° C. for 2 hours. While stirring the reaction solution, the temperature was raised over 2 hours to 0° C., and the solution was stirred at 0° C. for 1 hour. To the reaction solution, 4-methoxybenzylamine (656 mg) was added at 0*C, and the solution was stirred at room temperature for 16 hours. To the reaction solution, water, ethyl acetate, and hexane were added, the solution was stirred, and the precipitate was taken by filtering. The filtrate was extracted with ethyl acetate, and the organic layer was washed with a saturated saline solution. The obtained organic layer was dried over anhydrous sodium sulfate, and thereafter, was concentrated under a reduced pressure. The residue was washed with ethyl acetate/hexane. The residue was combined with the precipitate taken by filtering previously to give the title compound (1.47 g) having the following physical properties.

TLC: Rf 0.35 (hexane:ethyl acetate=3:1);

$^1$H-NMR (CDCl$_3$): δ1.76, 3.18, 4.70-4.76, 6.84-6.92, 7.21-7.34, 7.73.

Example 11: 3-(7-Fluoro-1H-indazol-4-yl)-$N^6$-[2-fluoro-4-(methylsulfonyl)phenyl]-1-(2-methyl-2-propanyl)-1H-pyrazolo[3,4-d]pyrimidine-4,6-diamine

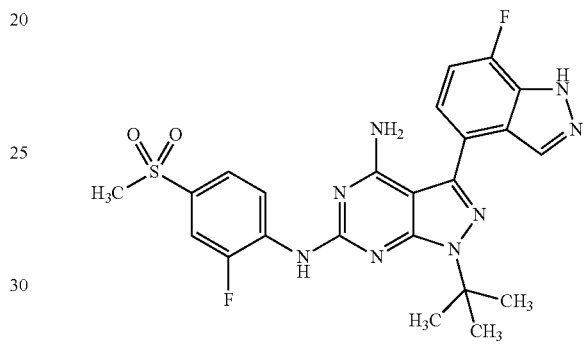

A similar procedure to Reference Example 2→Reference Example 5→Reference Example 6→Reference Example 7→Reference Example 8→Reference Example 9→Example 2 was carried out by using the compound prepared in Reference Example 14 instead of 4,6-dichloro-1H-pyrazolo[3,4-d]pyrimidine and using the boronic acid prepared in Reference Example 11 instead of 1-(tert-butyldimethylsilyl)-1H-indol-5-ylboronic acid to give the compound of the present invention having the following physical properties.

TLC: Rf 0.64 (hexane:ethyl acetate=1:2);

$^1$H-NMR (CDCl$_3$): δ1.89, 3.08, 5.23-5.31, 7.17-7.25, 7.34-7.40, 7.41-7.45, 7.65-7.71, 7.76, 7.82, 8.35-8.38, 8.97-9.03.

Example 12: 4-{[4-Amino-1-cyclopentyl-3-(3-hydroxyphenyl)-1H-pyrazolo[3,4-d]pyrimidin-6-yl]amino}-3-fluoro-N,N-dimethylbenzamide

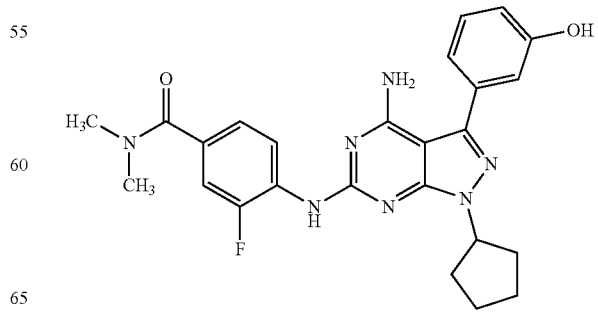

A similar procedure to Reference Example 1→Reference Example 4→Reference Example 5→Reference Example 6→Reference Example 7→Reference Example 8→Reference Example 9 was carried out by using 4-amino-3-fluoro-N,N-dimethylbenzamide instead of 1,3-dimethylpyrazol-4-amine hydrochloride, using cyclopentanol instead of isopropanol, and using 3-hydroxyphenylboronic acid instead of 1-(tert-butyldimethylsilyl)-1H-indol-5-ylboronic acid to give the compound of the present invention having the following physical properties.

$^1$H-NMR (DMSO-d$_6$): δ1.65-1.68, 1.75-1.87, 2.02-2.12, 2.98, 5.00-5.11, 6.84-6.87, 7.04-7.06, 7.24-7.26, 7.29-7.35, 8.20-8.27, 8.72, 9.60-9.75.

Purity (LC-MS/ELSD): 100% (Retention time: 0.89 minutes);

MASS (ESI, Pos.): 476 (M+H)$^+$.

Examples 13-1 to 13-15

A similar procedure to Reference Example 1→Reference Example 2→Reference Example 3→Reference Example 4→Reference Example 5→Reference Example 6→Reference Example 7→Reference Example 8→Reference Example 9→Example 2 was carried out by using 1,3-dimethylpyrazol-4-amine hydrochloride or a corresponding amine compound instead of 1,3-dimethylpyrazol-4-amine hydrochloride, using 2,4-dichloro-7H-pyrrolo[2,3-d]pyrimidine instead of 4,6-dichloro-1H-pyrazolo[3,4-d]pyrimidine, and using a corresponding boronic acid instead of 1-(tert-butyldimethylsilyl)-1H-indol-5-ylboronic acid to give the compound of the present invention having the following physical properties. Meanwhile, in Example 13-7, HPLC preparative purification was performed instead of silica gel column chromatography in Example 2.

Example 13-1: 4-(4-Amino-2-{[2-fluoro-4-(methylsulfonyl)phenyl]amino}-7-isopropyl-7H-pyrrolo[2,3-d]pyrimidin-5-yl)-1H-indazole-7-carbonitrile

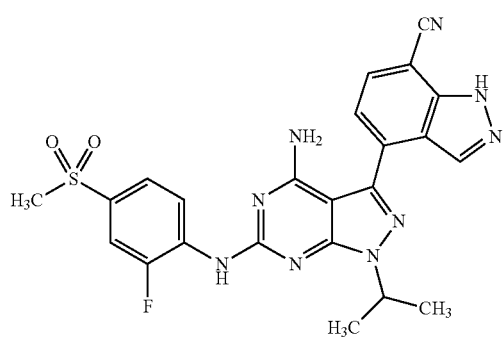 [SMILES: CC(C)n1nc(-c2ccc(C#N)c3[nH]ncc23)c2c(N)nc(Nc3ccc(S(C)(=O)=O)cc3F)nc21]

TLC: Rf 0.18 (hexane:ethyl acetate=1:1);

$^1$H-NMR (CDCl$_3$): δ1.59-1.64, 3.07, 4.94-5.08, 7.19, 7.27-7.31, 7.36-7.40, 7.62-7.68, 7.75-7.80, 7.81-7.84, 8.27, 8.99-9.06.

Example 13-2: 5-{[4-Amino-5-(1H-indazol-4-yl)-7-isopropyl-7H-pyrrolo[2,3-d]pyrimidin-2-yl]amino}-N,N-dimethyl-2-pyridinecarboxamide

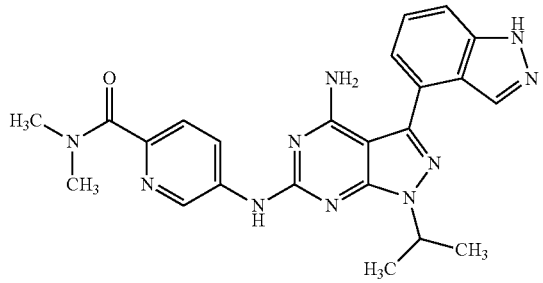 [SMILES: CC(C)n1nc(-c2cccc3[nH]ncc23)c2c(N)nc(Nc3ccc(C(=O)N(C)C)nc3)nc21]

TLC: Rf 0.32 (ethyl acetate:methanol=10:1);

$^1$H-NMR (CDCl$_3$): δ1.54-1.61, 3.08-3.23, 4.90-5.12, 7.01, 7.07, 7.19-7.23, 7.43-7.50, 7.68-7.72, 8.13, 8.23-8.27, 8.93-8.95, 10.21-10.36.

Example 13-3: 1-(4-{[4-Amino-5-(1H-indazol-4-yl)-7-isopropyl-7H-pyrrolo[2,3-d]pyrimidin-2-yl]amino}-3-methyl-1H-pyrazol-1-yl)-2-methyl-2-propanol TLC: Rf 0.31 (ethyl acetate:methanol=9:1);

$^1$H-NMR (CD$_3$OD): δ1.26, 1.57-1.62, 2.29, 4.09, 4.90-5.07, 7.20-7.23, 7.42, 7.49-7.56, 7.59-7.63, 8.01, 8.08.

Example 13-4: 2-(4-{[4-Amino-5-(1H-indazol-4-yl)-7-isopropyl-7H-pyrrolo[2,3-d]pyrimidin-2-yl]amino}-3-methyl-1H-pyrazol-1-yl)-N,N-dimethylacetamide TLC: Rf 0.40 (ethyl acetate:methanol=9:1);

$^1$H-NMR (CDCl$_3$): δ 1.52-1.58, 2.28, 3.00, 3.07, 4.85-5.03, 6.25, 6.99, 7.19-7.23, 7.43-7.49, 8.08, 8.13.

Example 13-5: 2-(4-{[4-Amino-5-(1H-indazol-4-yl)-7-isopropyl-7H-pyrrolo[2,3-d]pyrimidin-2-yl]amino}-3-methyl-1H-pyrazol-1-yl)-1-(4-morpholinyl)ethanone TLC: Rf 0.31 (ethyl acetate:methanol=9:1);

$^1$H-NMR (CD3 OD): δ1.54-1.61, 2.29, 3.60-3.64, 3.66-3.75, 4.95-5.04, 5.08, 7.17, 7.19-7.22, 7.47-7.57, 8.06, 8.12.

Example 13-6: 2-(4-{[4-Amino-5-(1H-indazol-4-yl)-7-isopropyl-7H-pyrrolo[2,3-d]pyrimidin-2-yl]amino}-3-methyl-1H-pyrazol-1-yl)-2-methyl-1,3-propanediol TLC: Rf 0.51 (ethyl acetate:methanol=10:1);

$^1$H-NMR (CD3 OD): δ1.57-1.62, 2.27, 3.83-3.88, 3.92-3.97, 4.95-5.02, 7.16, 7.18-722, 7.46-7.56, 8.06, 8.16.

Example 13-7: 6-{[4-Amino-5-(1H-indazol-4-yl)-7-isopropyl-7H-pyrrolo[2,3-d]pyrimidin-2-yl]amino}-1-methyl-1,3-dihydro-2H-indol-2-one trifluoroacetate TLC: Rf 0.35 (ethyl acetate, NH silica);
$^1$H-NMR (DMSO-$d_6$): δ1.56-1.62, 3.19, 3.56, 4.85-4.98, 7.13-7.00, 7.02-7.27, 7.44-7.51, 7.54-7.60, 7.74, 8.14, 9.58-9.74, 13.10-13.36.

Example 13-8: [4-({4-Amino-7-isopropyl-5-[4-(trifluoromethyl)phenyl]-7H-pyrrolo[2,3-d]pyrimidin-2-yl}amino)-3-fluorophenyl](1-piperazinyl)methanone TLC: Rf 0.28 (ethyl acetate:methanol=20:1, NH silica);
$^1$H-NMR (CDCl$_3$): δ1.53-1.58, 2.82-2.96, 3.55-3.75, 4.94-5.07, 6.93, 7.16-7.27, 7.59-7.63, 7.68-7.73, 8.76-8.83.

Example 13-9: 4-(4-Amino-2-{[2-fluoro-4-(1-piperazinylcarbonyl)phenyl]amino}-7-isopropyl-7H-pyrrolo[2,3-d]pyrimidin-5-yl)benzonitrile TLC: Rf 0.24 (ethyl acetate:methanol=20:1, NH silica);
$^1$H-NMR (CDCl$_3$): δ1.44-1.60, 2.83-2.94, 3.57-3.72, 4.86-5.04, 6.96, 7.15-7.27, 7.57-7.62, 7.69-7.76, 8.74-8.81.

Example 13-10: [4-({4-Amino-7-isopropyl-5-[4-(trifluoromethoxy)phenyl]-7H-pyrrolo[2,3-d]pyrimidin-2-yl}amino)-3-fluorophenyl](1-piperazinyl)methanone TLC: Rf 0.23 (ethyl acetate:methanol=20:1, NH silica);
$^1$H-NMR (CDCl$_3$): δ1.51-1.58, 2.92-3.01, 3.63-3.78, 4.96-5.08, 6.88, 7.17-7.34, 7.48-7.56, 8.76-8.83.

Example 13-11: (4-{[4-Amino-7-isopropyl-5-(3-methoxyphenyl)-7H-pyrrolo[2,3-d]pyrimidin-2-yl]amino}-3-fluorophenyl 1-piperazinyl)methanone TLC: Rf 0.20 (ethyl acetate:methanol=20:1, NH silica);
$^1$H-NMR (CDCl$_3$): δ1.52-1.57, 2.82-2.94, 3.50-3.70, 3.86, 4.92-5.10, 6.85-6.91, 7.00-7.03, 7.04-7.12, 7.13-7.25, 7.34-7.40, 8.76-8.84.

Example 13-12: N$^2$-(1,3-dimethyl-1H-pyrazol-4-yl)-5-(6-fluoro-1H-indazol-4-yl)-7-isopropyl-7H-pyrrolo[2,3-d]pyrimidine-2,4-diamine TLC: Rf 0.60 (ethyl acetate:methanol=10:1);
$^1$H-NMR (CDCl$_3$): δ1.52-1.58, 2.72, 3.86, 4.80-5.04, 6.21, 6.98-7.04, 7.05-7.12, 7.91, 8.10.

Example 13-13: N$^2$-(1,3-dimethyl-1H-pyrazol-4-yl)-7-isopropyl-5-(6-methyl-1H-indazol-4-yl)-7H-pyrrolo[2,3-d]pyrimidine-2,4-diamine TLC: Rf 0.20 (ethyl acetate:methanol=20:1);
$^1$H-NMR (DMSO-$d_6$): δ1.40-1.48, 2.11, 2.45, 3.72, 4.80-4.93, 5.55-6.05, 6.90, 7.20-7.30, 7.48-7.68, 7.85-7.98, 12.98.

Example 13-14: N$^2$-(1,3-dimethyl-1H-pyrazol-4-yl)-7-isopropyl-5-(7-methyl-1H-indazol-4-yl)-7H-pyrrolo[2,3-d]pyrimidine-2,4-diamine TLC: Rf 0.51 (ethyl acetate:methanol=10:1);
$^1$H-NMR (CDCl$_3$): δ1.52-1.58, 2.27, 2.60, 3.86, 4.82-5.04, 6.22, 6.95, 7.12-7.18, 7.21-7.30, 7.92, 8.13.

Example 13-15: N$^2$-(1,3-dimethyl-1H-pyrazol-4-yl)-7-isopropyl-5-(5-methyl-1H-indazol-4-yl)-7H-pyrrolo[2,3-d]pyrimidine-2,4-diamine TLC: Rf 0.27 (ethyl acetate:methanol=20:1);
$^1$H-NMR (CDCl$_3$): δ1.48-1.60, 2.26, 2.37, 3.85, 4.48-4.62, 4.91-5.06, 6.26, 6.80, 7.26, 7.32-7.43, 7.82, 7.92.

Examples 14-1 to 14-13

A similar procedure to Reference Example 1→Reference Example 2→Reference Example 3→Reference Example 4→Reference Example 5→Reference Example 6→Reference Example 7→Reference Example 8→Reference Example 9 was carried out by using 1,3-dimethylpyrazol-4-amine hydrochloride or a corresponding amine compound instead of 1,3-dimethylpyrazol-4-amine hydrochloride, using 2,4-dichloro-7H-pyrrolo[2,3-d]pyrimidine instead of 4,6-dichloro-1H-pyrazolo[3,4-d]pyrimidine and using a corresponding boronic acid instead of 1-(tert-butyldimethylsilyl)-1H-indol-5-ylboronic acid to give the compound of the present invention having the following physical properties.

Example 14-1: 5-(1-Benzofuran-3-yl)-N$^2$-(1,3-dimethyl-1H-pyrazol-4-yl)-7-isopropyl-7H-pyrrolo[2,3-d]pyrimidine-2,4-diamine

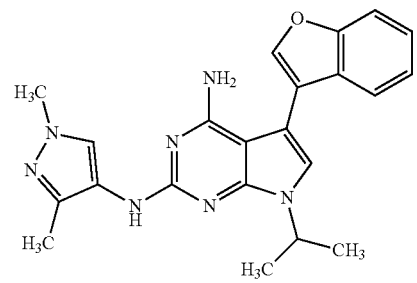 [SMILES: Cc1nn(C)cc1Nc1nc(N)c2c(-c3coc4ccccc34)cn(C(C)C)c2n1]

TLC: Rf 0.65 (ethyl acetate:methanol=10:1);
$^1$H-NMR (CDCl$_3$): δ1.50-1.60, 2.26, 3.86, 4.82-5.02, 6.24, 6.90, 7.22-7.44, 7.54-7.59, 7.61-7.65, 7.72, 7.91.

Example 14-2: 5-(1,2-Benzothiazol-5-yl)-N$^2$-(1,3-dimethyl-1H-pyrazol-4-yl)-7-isopropyl-7H-pyrrolo[2,3-d]pyrimidine-2,4-diamine

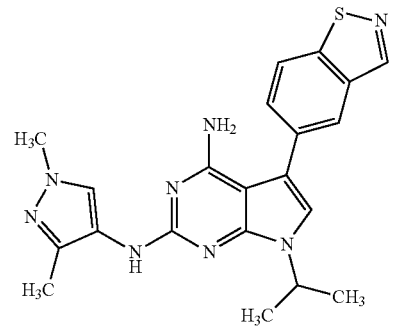 [SMILES: Cc1nn(C)cc1Nc1nc(N)c2c(-c3ccc4sncc4c3)cn(C(C)C)c2n1]

TLC: Rf 0.54 (ethyl acetate, NH silica);
$^1$H-NMR (CDCl$_3$): δ1.48-1.58, 2.27, 3.87, 4.84-5.02, 6.18-6.23, 6.87, 7.68-7.72, 7.91, 8.01-8.05, 8.16-8.17, 8.95.

Example 14-3: 5-(2,1-Benzothiazol-5-yl)-N$^2$-(1,3-dimethyl-1H-pyrazol-4-yl)-7-isopropyl-7H-pyrrolo[2,3-d]pyrimidine-2,4-diamine TLC: Rf 0.23 (ethyl acetate);
$^1$H-NMR (CDCl$_3$): δ1.51-1.57, 2.27, 3.86, 4.88-5.02, 6.20, 6.89, 7.61-7.66, 7.84, 7.89-7.94, 9.18.

Example 14-4: N$^2$-(1,3-dimethyl-1H-pyrazol-4-yl)-7-isopropyl-5-(1H-pyrrolo[2,3-b]pyridin-3-yl)-7H-pyrrolo[2,3-d]pyrimidine-2,4-diamine TLC: Rf 0.36 (ethyl acetate:methanol=5:1);
$^1$H-NMR (CDCl$_3$): δ1.51-1.58, 2.27, 3.86, 4.79-4.83, 4.91-5.02, 6.17, 6.83, 7.14-7.18, 7.37-7.40, 7.93, 7.98-8.01, 8.37-8.40, 8.79.

Example 14-5: 5-(4-Amino-2-{[2-fluoro-4-(methylsulfonyl)phenyl]amino}-7-isopropyl-7H-pyrrolo[2,3-d]pyrimidin-5-yl)-1 (2H)-isoquinolinone TLC: Rf 0.27 (ethyl acetate);
$^1$H-NMR (CD3 OD): δ1.56-1.64, 3.13, 4.98-5.07, 6.43-6.67, 7.12, 7.13-7.17, 7.58-7.79, 8.36-8.41, 9.08-9.16.

Example 14-6: N$^2$-[2-fluoro-4-(methylsulfonyl)phenyl]-7-isopropyl-5-(5-quinolinyl)-7H-pyrrolo[2,3-d]pyrimidine-2,4-diamine TLC: Rf 0.23 (ethyl acetate);
$^1$H-NMR (CDCl$_3$): δ1.52-1.68, 3.07, 4.52-4.62, 4.98-5.10, 6.98, 7.31-7.38, 7.39-7.44, 7.60-7.67, 7.74-7.82, 8.15-8.19, 8.28-8.32, 8.95-8.99, 9.01-9.09.

Example 14-7: Methyl(4-{[4-amino-5-(1-benzofuran-5-yl)-7-isopropyl-7H-pyrrolo[2,3-d]pyrimidin-2-yl]amino}-3-methyl-1H-pyrazol-1-yl)acetate TLC: Rf 0.50 (ethyl acetate);
$^1$H-NMR (CDCl$_3$): δ1.49-1.55, 2.29, 3.78, 4.86, 4.90-5.00, 6.26, 6.78-6.81, 7.39-7.43, 7.54-7.59, 7.67-7.70, 8.05.

Example 14-8: 5-(1-Benzofuran-5-yl)-N$^2$-(1,5-dimethyl-1H-pyrazol-4-yl)-7-isopropyl-7H-pyrrolo[2,3-d]pyrimidine-2,4-diamine TLC: Rf 0.58 (ethyl acetate);
$^1$H-NMR (CDCl$_3$): δ1.44-1.51, 2.23, 3.80, 4.83-5.02, 6.01, 6.77, 6.78-6.81, 7.39-7.44, 7.53-7.58, 7.66-7.70, 7.84.

Example 14-9: 5-(1-Benzofuran-5-yl)-N$^2$-[1-(difluoromethyl)-3-methyl-1H-pyrazol-4-yl]-7-isopropyl-7H-pyrrolo[2,3-d]pyrimidine-2,4-diamine TLC: Rf 0.56 (hexane:ethyl acetate=2:3);
$^1$H-NMR (CDCl$_3$): δ1.53-1.60, 2.32, 4.89-5.03, 6.29, 6.79-6.84, 7.40-7.45, 7.55-7.61, 7.65-7.72, 8.45.

Example 14-10: 5-(1-Benzofuran-5-yl)-N$^2$-(2,5-dimethyl-1,3-thiazol-4-yl)-7-isopropyl-7H-pyrrolo[2,3-d]pyrimidine-2,4-diamine TLC: Rf 0.25 (hexane:ethyl acetate=1:2);
$^1$H-NMR (CDCl$_3$): δ1.52-1.59, 2.37, 2.63, 4.89-5.03, 6.59-6.66, 6.80-6.84, 7.39-7.43, 7.56-7.60, 7.67-7.71.

Example 14-11: 5-(1-Benzofuran-5-yl)-7-isopropyl-N$^2$-(3-methoxy-1-methyl-1H-pyrazol-4-yl)-7H-pyrrolo[2,3-d]pyrimidine-2,4-diamine TLC: Rf 0.48 (hexane:ethyl acetate=1:4);
$^1$H-NMR (CDCl$_3$): δ1.46-1.54, 3.77, 3.96, 4.80-5.01, 6.32, 6.70-6.81, 7.40-7.44, 7.54-7.58, 7.66-7.70, 7.86.

Example 14-12: 5-[4-(Difluoromethoxy)phenyl]-N$^2$-[2-fluoro-4-(methylsulfonyl)phenyl]-7-isopropyl-7H-pyrrolo[2,3-d]pyrimidine-2,4-diamine TLC: Rf 0.33 (hexane:ethyl acetate=2:1);
$^1$H-NMR (CDCl$_3$): δ1.53-1.58, 3.07, 4.92-5.03, 6.32-6.81, 6.89, 7.18-7.27, 7.28-7.34, 7.47-7.51, 7.62-7.67, 7.73-7.77, 9.00-9.07.

Example 14-13: 4-{[4-Amino-5-(4-chloro-3-methoxyphenyl)-7-isopropyl-7H-pyrrolo[2,3-d]pyrimidin-2-yl]amino}-3-fluoro-N-methylbenzamide TLC: Rf 0.47 (hexane:ethyl acetate=1:4);
$^1$H-NMR (CDCl$_3$): δ1.50-1.60, 3.00-3.03, 3.96, 4.92-5.03, 6.00-6.08, 6.89, 7.00-7.12, 7.18-7.21, 7.40-7.45, 7.52-7.59, 8.80-8.86.

Reference Example 15: Methyl 4-{[4-amino-5-(1-benzofuran-5-yl)-7-(propan-2-yl)-7H-pyrrolo[2,3-d]pyrimidin-2-yl]amino}-3-fluorobenzoate A similar procedure to Reference Example 1→Reference Example 2→Reference Example 3→Reference Example 4→Reference Example 5→Reference Example 6→Reference Example 7→Reference Example 8→Reference Example 9 was carried out by using methyl 4-amino-3-fluorobenzoate instead of 1,3-dimethylpyrazol-4-amine hydrochloride, using 2,4-dichloro-7H-pyrrolo[2,3-d]pyrimidine instead of 4,6-dichloro-1H-pyrazolo[3,4-d]pyrimidine, and using benzofuran-5-boronic acid instead of 1-(tert-butyldimethylsilyl)-1H-indol-5-ylboronic acid to give the title compound having the following physical properties.
TLC: Rf 0.81 (hexane:ethyl acetate=1:1);
$^1$H-NMR (CDCl$_3$): δ1.55-1.62, 3.90, 4.93-5.06, 6.81, 6.89, 7.22-7.28, 7.40-7.44, 7.56-7.61, 7.64-7.77, 7.84-7.91, 8.84-8.92.

Example 15: 4-{[4-Amino-5-(1-benzofuran-5-yl)-7-isopropyl-7H-pyrrolo[2,3-d]pyrimidin-2-yl]amino}-3-fluorobenzoic acid

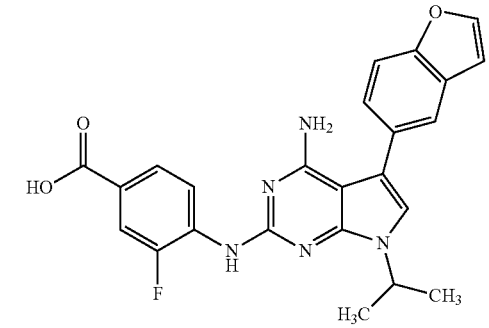 [SMILES: CC(C)n1cc(-c2ccc3occc3c2)c2c(N)nc(Nc3ccc(C(=O)O)cc3F)nc21]

To a solution of the compound (113 mg) prepared in Reference Example 15 in ethanol (5 mL), 2 N sodium hydroxide aqueous solution (1 mL) was added, and the mixture was stirred at 40° C. for 3 hours. The reaction solution was neutralized with 2 N hydrochloric acid, and thereafter, was extracted with ethyl acetate. The obtained organic layer was dried over anhydrous sodium sulfate, and was concentrated under a reduced pressure. The residue was purified by silica gel column chromatography to give the compound of the present invention (65 mg) having the following physical properties.

TLC: Rf 0.45 (hexane:ethyl acetate=2:3);
$^1$H-NMR (DMSO-$d_6$): δ1.43-1.49, 4.80-4.95, 6.00-6.30, 6.96-7.00, 7.26, 7.36-7.42, 7.60-7.76, 8.00-8.03, 8.25-8.43, 8.60-8.71.

Example 16: [(4-{[4-Amino-5-(1-benzofuran-5-yl)-7-isopropyl-7H-pyrrolo[2,3-d]pyrimidin-2-yl]amino}-3-fluorophenyl)sulfonyl]acetic acid

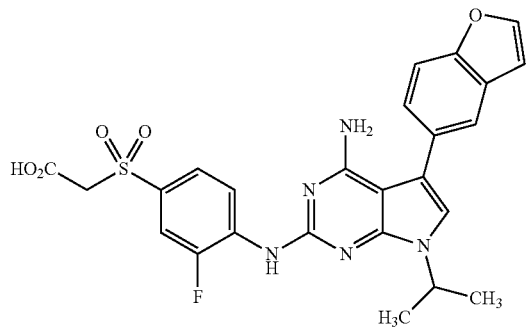 [SMILES: CC(C)n1cc(-c2ccc3occc3c2)c2c(N)nc(Nc3ccc(S(=O)(=O)CC(=O)O)cc3F)nc21]

A similar procedure to Reference Example 1→Reference Example 2→Reference Example 3→Reference Example 4→Reference Example 5→Reference Example 6→Reference Example 7→Reference Example 8→Reference Example 9→Example 15 was carried out by using ethyl[(4-amino-3-fluorophenyl)sulfonyl]acetate instead of 1,3-dimethylpyrazol-4-amine hydrochloride, using 2,4-dichloro-7H-pyrrolo[2,3-d]pyrimidine instead of 4,6-dichloro-1H-pyrazolo[3,4-d]pyrimidine and using benzofuran-5-boronic acid instead of 1-(tert-butyldimethylsilyl)-1H-indol-5-ylboronic acid to give the compound of the present invention having the following physical properties.

TLC: Rf 0.40 (ethyl acetate:methanol=3:1);
$^1$H-NMR (DMSO-$d_6$): δ1.40-1.50, 4.44, 4.87-4.98, 5.95-6.18, 6.98-7.01, 7.25, 7.37-7.42, 7.63-7.75, 8.00-8.02, 8.45-8.50, 8.81-8.90.

Example 17: N$^2$-(1,3-dimethyl-1H-pyrazol-4-yl)-5-(1H-indol-3-yl)-7-isopropyl-7H-pyrrolo[2,3-d]pyrimidine-2,4-diamine

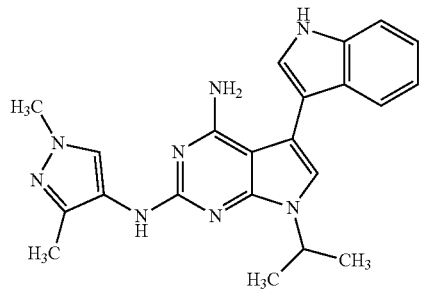 [SMILES: Cc1nn(C)cc1Nc1nc(N)c2c(-c3c[nH]c4ccccc34)cn(C(C)C)c2n1]

A similar procedure to Reference Example 1→Reference Example 2→Reference Example 3→Reference Example 4→Reference Example 5→Reference Example 6→Reference Example 7→Reference Example 8→Reference Example 9→Example 1 was carried out by using 2,4-dichloro-7H-pyrrolo[2,3-d]pyrimidine instead of 4,6-dichloro-1H-pyrazolo[3,4-d]pyrimidine, and using 1-(toluene-4-sulfonyl)-1H-indole-3-boronic acid N-tert-butyldimethylsilyl protected product instead of 1-(tert-butyldimethylsilyl)-1H-indol-5-ylboronic acid to give the compound of the present invention having the following physical properties.

TLC: Rf 0.40 (ethyl acetate:methanol=20:1);
$^1$H-NMR (CDCl$_3$): δ1.50-1.57, 2.26, 3.86, 4.81-5.02, 6.22, 6.84, 7.13-7.21, 7.25-7.31, 7.41-7.45, 7.64-7.70, 7.93, 8.29.

Examples 18-1 to 18-2

A similar procedure to Reference Example 1→Reference Example 2→Reference Example 3→Reference Example 4→Reference Example 5→Reference Example 6→Reference Example 7→Reference Example 8→Reference Example 9→Example 2→Example 15 was carried out by using a corresponding amine compound instead of 1,3-dimethylpyrazol-4-amine hydrochloride, using 2,4-dichloro-7H-pyrrolo[2,3-d]pyrimidine instead of 4,6-dichloro-1H-pyrazolo[3,4-d]pyrimidine, and using 1-(tetrahydro-2H-pyran-2-yl)-1H-indazol-4-yl-4-boronic acid instead of 1-(tert-butyldimethylsilyl)-1H-indol-5-ylboronic acid to give the compound of the present invention having the following physical properties.

Example 18-1: (4-{[4-Amino-5-(1H-indazol-4-yl)-7-isopropyl-7H-pyrrolo[2,3-d]pyrimidin-2-yl]amino}-2,5-difluorophenyl)acetic acid

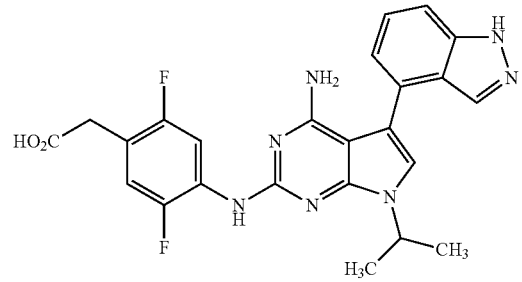 [SMILES: CC(C)n1cc(-c2cccc3[nH]ncc23)c2c(N)nc(Nc3cc(F)c(CC(=O)O)cc3F)nc21]

TLC: Rf 0.41 (ethyl acetate:methanol=20:1);
$^1$H-NMR (CD$_3$OD): δ1.57-1.63, 3.51, 4.95-5.03, 7.04-7.14, 7.17-7.22, 7.43-7.54, 8.04, 8.53-8.60.

Example 18-2: 2-(4-{[4-Amino-5-(1H-indazol-4-yl)-7-isopropyl-7H-pyrrolo[2,3-d]pyrimidin-2-yl]amino}-2,3-difluorophenyl)-2-methylpropanoic acid

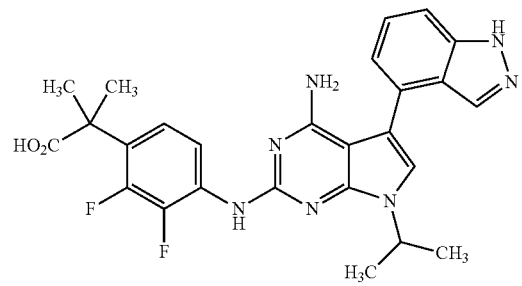 [SMILES: CC(C)n1cc(-c2cccc3[nH]ncc23)c2c(N)nc(Nc3ccc(C(C)(C)C(=O)O)c(F)c3F)nc21]

TLC: Rf 0.61 (ethyl acetate:methanol=20:1);
$^1$H-NMR (CD3 OD): δ1.54-1.60, 4.94-5.03, 7.07-7.21, 7.43-7.54, 8.03, 8.33-8.40.

Reference Example 16: Benzyl [4-({4-amino-7-(propan-2-yl)-5-[1-(tetrahydro-2H-pyran-2-yl)-1H-indazol-4-yl]-7H-pyrrolo[2,3-d]pyrimidin-2-yl}amino)-3-methyl-1H-pyrazol-1-yl]acetate A similar procedure to Reference Example 1→Reference Example 2→Reference Example 3→Reference Example 4→Reference Example 5→Reference Example 6→Reference Example 7→Reference Example 8→Reference Example 9 was carried out by using benzyl(4-amino-3-methyl-1H-pyrazol-1-yl)acetate instead of 1,3-dimethyl-pyrazol-4-amine hydrochloride, using 2,4-dichloro-7H-pyrrolo[2,3-d]pyrimidine instead of 4,6-dichloro-1H-pyrazolo[3,4-d]pyrimidine, and using 1-(tetrahydro-2H-pyran-2-yl)-1H-indazol-4-yl-4-boronic acid instead of 1-(tert-butyldimethylsilyl)-1H-indol-5-ylboronic acid to give the title compound having the following physical properties.
TLC: Rf 0.62 (ethyl acetate);
$^1$H-NMR (CDCl$_3$): δ1.42-1.58, 1.62-1.84, 2.04-2.23, 2.35, 2.54-2.67, 3.73-3.83, 4.03-4.11, 4.80-5.00, 5.22, 5.74-5.80, 6.22, 6.95, 7.19-7.38, 7.42-7.49, 7.52-7.57, 8.07.

Reference Example 17: [4-({4-Amino-7-(propan-2-yl)-5-[1-(tetrahydro-2H-pyran-2-yl)-1H-indazol-4-yl]-7H-pyrrolo[2,3-d]pyrimidin-2-yl}amino)-3-methyl-1H-pyrazol-1-yl]acetic acid To a solution of the compound (20 mg) prepared in Reference Example 16 in ethanol (1 mL), 10% palladium on carbon (Pd/C) (4 mg) was added, and the mixture was stirred under a hydrogen gas atmosphere at room temperature for 3 hours. The reaction solution was filtered through Celite, and the filtrate was concentrated under a reduced pressure to give the compound of the present invention (15 mg) having the following physical properties.
TLC: Rf 0.39 (ethyl acetate:methanol=1:1);
$^1$H-NMR (CDCl$_3$): δ1.42-1.58, 1.62-1.84, 2.00-2.65, 2.35, 3.68-3.83, 4.02-4.10, 4.78-4.95, 5.75-5.82, 6.98, 7.13-7.19, 7.42-7.48, 7.59-7.64, 7.71, 8.01.

Reference Example 18: 2-[4-({4-Amino-7-(propan-2-yl)-5-[1-(tetrahydro-2H-pyran-2-yl)-1H-indazol-4-yl]-7H-pyrrolo[2,3-d]pyrimidin-2-yl}amino)-3-methyl-1H-pyrazol-1-yl]acetamide To a solution of the compound (50 mg) prepared in Reference Example 17 in N,N-dimethylformamide (1 mL), diisopropylethylamine (25 µL), ammonium chloride (8 mg), and 2-(7-aza-1H-benzotriazol-1-yl)-1,1,3,3-tetramethyluronium hexafluorophosphate (hereinafter, abbreviated as HATU) (54 mg) were added at room temperature, and the mixture was stirred for 1 hour. The reaction solution was diluted with ethyl acetate, and was washed with water, and a saturated saline solution. The obtained organic layer was dried over anhydrous sodium sulfate, and was concentrated under a reduced pressure. The residue was purified by silica gel column chromatography to give the title compound (37 mg) having the following physical properties.
TLC: Rf 0.43 (ethyl acetate:methanol=9:1);
$^1$H-NMR (CDCl$_3$): δ1.51-1.59, 1.62-1.88, 2.06-2.24, 2.37, 2.54-2.67, 3.73-3.83, 4.03-4.11, 4.77, 4.87-5.01, 5.39-5.62, 5.75-5.80, 6.30, 6.99, 7.18-7.21, 7.43-7.49, 7.56-7.61, 8.03, 8.09.

Example 19: 2-(4-{[4-Amino-5-(1H-indazol-4-yl)-7-isopropyl-7H-pyrrolo[2,3-d]pyrimidin-2-yl]amino}-3-methyl-1H-pyrazol-1-yl)acetamide

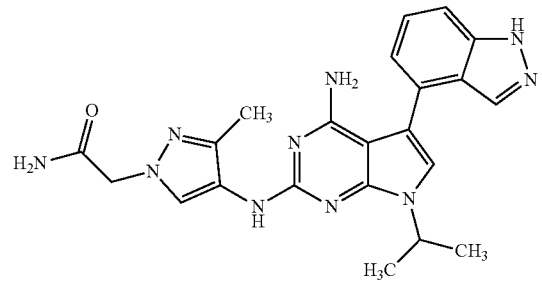 [SMILES: Cc1nn(CC(N)=O)cc1Nc1nc(N)c2c(-c3cccc4[nH]ncc34)cn(C(C)C)c2n1]

To a solution of the compound (10 mg) prepared in Reference Example 18 in dichloromethane (1 mL), trifluoroacetic acid (140 ILL) was added at room temperature, and the mixture was stirred for 6 hours. The reaction solution was diluted with dichloromethane, and was washed with a saturated sodium bicarbonate aqueous solution, and a saturated saline solution. The obtained organic layer was dried over anhydrous sodium sulfate, and was concentrated under a reduced pressure. The residue was purified by preparative thin-layer silica gel column chromatography to give the compound of the present invention (5.5 mg) having the following physical properties.
TLC: Rf 0.40 (ethyl acetate:methanol=1:1);
$^1$H-NMR (CD$_3$ OD): δ1.56-1.61, 2.29, 4.81, 4.95-5.04, 7.17, 7.19-7.22, 7.43-7.57, 8.05, 8.10.

Example 20: (4-{[4-Amino-5-(1H-indazol-4-yl)-7-isopropyl-7H-pyrrolo[2,3-d]pyrimidin-2-yl]amino}-3-methyl-1H-pyrazol-1-yl)acetonitrile

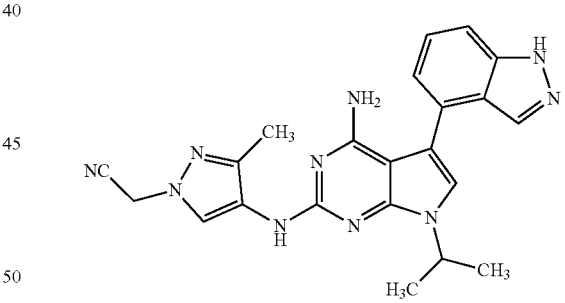

To a solution of the compound (20 mg) prepared in Reference Example 18 in dichloromethane (1.5 mL), pyridine (0.5 mL) and trifluoroacetic anhydride (27 µL) were added at 0° C., and the mixture was stirred at room temperature for 18 hours. To the reaction solution, a saturated sodium bicarbonate aqueous solution was added, and the solution was stirred at room temperature for 16 hours. The reaction solution was diluted with dichloromethane, and was washed with a saturated sodium bicarbonate aqueous solution and a saturated saline solution. The obtained organic layer was dried over anhydrous sodium sulfate, and was concentrated under a reduced pressure. The residue was purified by silica gel column chromatography to give a tetrahydropyran protected product of the title compound (15 mg). A similar procedure to Example 2 was carried out by using the tetrahydropyran protected product (15 mg) to give the compound of the present invention having the following physical properties.

TLC: Rf 0.29 (ethyl acetate);
$^1$H-NMR (CDCl$_3$): δ1.56-1.61, 2.29, 4.88-5.04, 6.41, 7.02, 7.20-7.23, 7.43-7.48, 8.14, 8.22.

Example 21: 4-{[4-Amino-5-(1-benzofuran-5-yl)-7-isopropyl-7H-pyrrolo[2,3-d]pyrimidin-2-yl]amino}-N-[2-(dimethylamino)ethyl]-3-fluorobenzamide

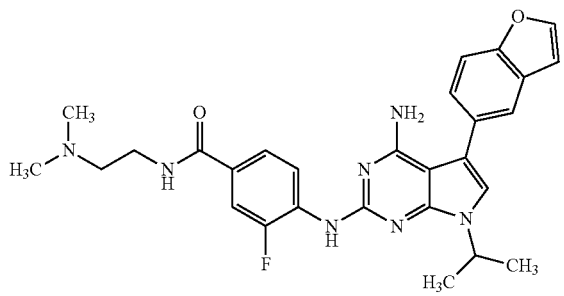 [SMILES: CC(C)n1cc(-c2ccc3occc3c2)c2c(N)nc(Nc3ccc(C(=O)NCCN(C)C)cc3F)nc21]

To a solution of the compound (20 mg) prepared in Example 15 in N,N-dimethylformamide (4 mL), diisopropylethylamine (23 μL), N,N-dimethylethylenediamine (10 μL), and HATU (26 mg) were added at room temperature, and the mixture was stirred for 16 hours. The reaction solution was diluted with ethyl acetate, and was washed with water and, a saturated saline solution. The obtained organic layer was dried over anhydrous sodium sulfate, and was concentrated under a reduced pressure. The residue was purified by silica gel column chromatography to give the compound of the present invention (19 mg) having the following physical properties.

TLC: Rf 0.30 (hexane:ethyl acetate=1:2, NH silica);
$^1$H-NMR (CDCl$_3$): δ1.53-1.60, 2.29, 2.49-2.57, 3.48-3.56, 4.94-5.08, 6.75-6.83, 6.88, 7.18-7.22, 7.40-7.45, 7.55-7.64, 7.68-7.72, 8.81-8.88.

Example 22: 4-{[4-Amino-5-(4-chloro-3-hydroxyphenyl)-7-isopropyl-7H-pyrrolo[2,3-d]pyrimidin-2-yl]amino}-3-fluoro-N-methylbenzamide

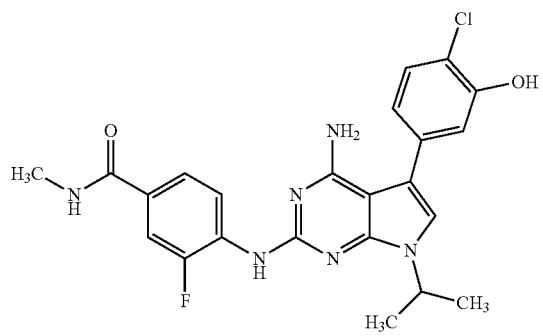 [SMILES: CNC(=O)c1ccc(Nc2nc(N)c3c(-c4ccc(Cl)c(O)c4)cn(C(C)C)c3n2)c(F)c1]

To a solution of the compound (32 mg) prepared in Example 14-13 in dichloromethane (2 mL), boron tribromide (38 μL) was added at 0° C., and the mixture was stirred at room temperature for 1 hour. The reaction solution was cooled to 0° C., and thereafter, ammonia water was added to the solution. The reaction solution was extracted with dichloromethane, and thereafter, the organic layer was concentrated under a reduced pressure. The residue was purified by preparative HPLC to give a trifluoroacetate of the compound of the present invention. To the trifluoroacetate, a saturated sodium bicarbonate aqueous solution was added, and the mixture was extracted with dichloromethane. The obtained organic layer was concentrated under a reduced pressure to give the compound of the present invention (8 mg) having the following physical properties.

TLC: Rf 0.24 (hexane:ethyl acetate=1:1);
$^1$H-NMR (DMSO-d$_6$): δ1.42-1.47, 2.76-2.80, 4.76-4.86, 6.91-6.97, 6.98-7.00, 7.17-7.22, 7.63-7.72, 8.36-8.41, 8.43-8.52, 10.28.

Reference Example 19: 2,4-Dichloro-5-iodo-7-(oxetan-3-yl)-7H-pyrrolo[2,3-d]pyrimidine A similar procedure to Reference Example 2→Reference Example 4 was carried out by using 2,4-dichloro-7H-pyrrolo[2,3-d]pyrimidine instead of 4,6-dichloro-1H-pyrazolo[3,4-d]pyrimidine, and using oxetan-3-ol instead of isopropanol to give the title compound having the following physical properties.

TLC: Rf 0.51 (hexane:ethyl acetate=2:1);
$^1$H-NMR (CDCl$_3$): δ4.84-4.92, 5.15-5.23, 5.92-6.02, 7.89.

Reference Example 20: 2-Chloro-5-iodo-7-(oxetan-3-yl)-7H-pyrrolo[2,3-d]pyrimidin-4-amine A solution of the compound (127 mg) prepared in Reference Example 19 in ammonia/methanol (1.5 mL, 8 M) was stirred in a sealed tube at 90° C. for 16 hours. The reaction solution was diluted with ethyl acetate, and thereafter, was washed with water, and a saturated saline solution. The obtained organic layer was dried over anhydrous magnesium sulfate, and was concentrated under a reduced pressure. The residue was washed with water, hexane, and ethyl acetate to give the title compound (88 mg) having the following physical properties.

TLC: Rf 0.33 (hexane:ethyl acetate=2:1);
$^1$H-NMR (CDCl$_3$): δ4.80-4.88, 5.09-5.20, 5.70-5.98, 7.56.

Example 23: 1-(4-{[4-Amino-5-(1H-indazol-4-yl)-7-(3-oxetanyl)-7H-pyrrolo[2,3-d]pyrimidin-2-yl]amino}-3-methyl-1H-pyrazol-1-yl)-2-methyl-2-propanol

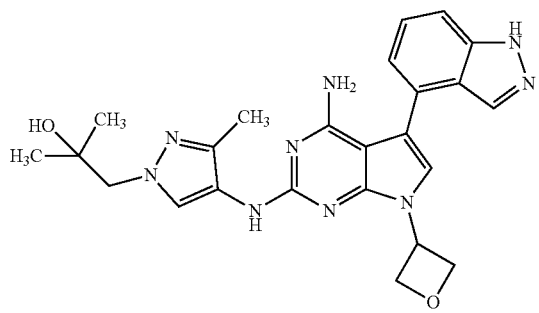 [SMILES: Cc1nn(CC(C)(C)O)cc1Nc1nc(N)c2c(-c3cccc4[nH]ncc34)cn(C3COC3)c2n1]

A similar procedure to Reference Example 1→Reference Example 6→Reference Example 7→Reference Example 8→Reference Example 9→Example 2 was carried out by using the compound prepared in Reference Example 20 instead of the compound prepared in Reference Example 8, using 1-(4-amino-3-methyl-1H-pyrazol-1-yl)-2-methylpropan-2-ol instead of 1,3-dimethylpyrazol-4-amine hydrochloride, and using [1-(tetrahydro-2H-pyran-2-yl)-1H-indazol-4-yl]boronic acid instead of the boronic acid prepared in Reference Example 11 to give the compound of the present invention having the following physical properties.

TLC: Rf 0.51 (ethyl acetate:methanol=9:1);

$^1$H-NMR (CDCl$_3$): δ1.19, 2.29, 4.01, 4.84-4.96, 5.12-5.18, 5.34-5.40, 5.65-5.77, 6.33, 7.12, 7.20-7.23, 7.45-7.50, 8.12, 8.23.

Reference Example 21: 2,4-Dichloro-7-(difluoromethyl)-7H-pyrrolo[2,3-d]pyrimidine 2,4-Dichloro-7H-pyrrolo[2,3-d]pyrimidine (188 mg) was dissolved in an aqueous solution (2.7 mL) of potassium hydroxide (898 mg). To the solution, a solution of 1-chloro-4-chlorodifluoromethanesulfonylbenzene (392 mg) in acetonitrile (3 mL) was added at −78° C., and the mixture was stirred at 80° C. for 1 hour. To the reaction solution, 1 N hydrochloric acid was added, the mixture was extracted with ethyl acetate, and the organic layer was washed with a saturated saline solution. The obtained organic layer was dried over anhydrous sodium sulfate, and thereafter, was concentrated under a reduced pressure. The residue was washed with methanol, and thereafter, was filtrated to give the title compound (96 mg) having the following physical properties.

TLC: Rf 0.25 (hexane:ethyl acetate=1:1);

$^1$H-NMR (CDCl$_3$): δ6.78-6.80, 7.52-7.92.

Example 24: 4-{[4-Amino-5-(1-benzofuran-5-yl)-7-(difluoromethyl)-7H-pyrrolo[2,3-d]pyrimidin-2-yl]amino}-3-fluoro-N,N-dimethylbenzamide

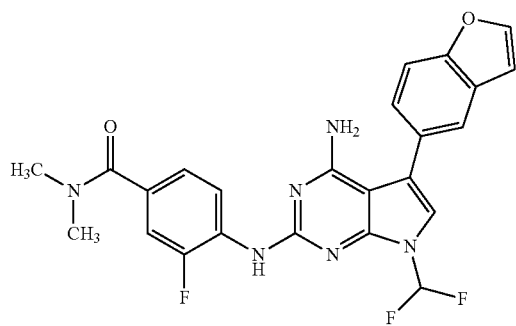 [SMILES: CN(C)C(=O)c1ccc(Nc2nc(N)c3c(-c4ccc5occc5c4)cn(C(F)F)c3n2)c(F)c1]

A similar procedure to Reference Example 1→Reference Example 2→Reference Example 3→Reference Example 5→Reference Example 6→Reference Example 7→Reference Example 8→Reference Example 9 was carried out by using the compound prepared in Reference Example 21 instead of 4,6-dichloro-1H-pyrazolo[3,4-d]pyrimidine, using benzofuran-5-boronic acid instead of 1-(tert-butyldimethylsilyl)-1H-indol-4-ylboronic acid, and using 4-amino-3-fluoro-N,N-dimethylbenzamide instead of 2-fluoro-4-(methylsulfonyl)aniline to give the compound of the present invention having the following physical properties.

TLC: Rf 0.37 (dichloromethane:methanol=9:1);

$^1$H-NMR (CDCl$_3$): δ3.00-3.18, 5.02-5.12, 6.82-6.84, 7.05, 7.16-7.19, 7.21-7.27, 7.40-7.45, 7.48-7.89, 8.58-8.64.

Reference Example 22: N,N-dibenzyl-2-chloropyrrolo[2,1-f][1,2,4]triazin-4-amine To a solution of 2,4-dichloropyrrolo[2,1-f][1,2,4]triazine (19 mg) in isopropanol (1 mL), dibenzylamine (20 mg) was added, and the mixture was stirred at room temperature for 2 hours. The reaction solution was concentrated under a reduced pressure, and thereafter, the residue was purified by silica gel column chromatography to give the title compound (30 mg) having the following physical properties.

$^1$H-NMR (CDCl$_3$): δ4.99, 6.49-6.53, 7.28-7.36, 7.55-7.59.

Reference Example 23: 4-{[4-(Dibenzylamino)pyrrolo[2,1-f][1,2,4]triazin-2-yl]amino}-3-fluoro-N,N-dimethylbenzamide To a solution of the compound (30 mg) prepared in Reference Example 22 and 4-amino-3-fluoro-N,N-dimethylbenzamide (31.5 mg) in tert-butanol (2 mL), potassium carbonate (36 mg) and Xantphos (10 mg) were added, and the mixture was deaerated. Under a nitrogen atmosphere, to the reaction solution, tris(dibenzylideneacetone)dipalladium (0)(Pd$_2$ (dba)$_3$) (8 mg) was added, and the mixture was heated at 120° C. for 1 hour by using a microwave. The reaction solution was diluted with ethyl acetate, and was washed with water, and a saturated saline solution. The obtained organic layer was dried over anhydrous sodium sulfate, and was concentrated under a reduced pressure. The residue was purified by silica gel column chromatography to give the title compound (40 mg) having the following physical properties.

$^1$H-NMR (CDCl$_3$): 53.06, 5.01, 6.42-6.49, 6.73, 7.15, 7.20, 7.28-7.38, 7.50-7.51, 8.50.

Reference Example 24: 4-{[7-Bromo-4-(dibenzylamino)pyrrolo[2,1-f][1,2,4]triazin-2-yl]amino}-3-fluoro-N,N-dimethylbenzamide To a solution of the compound (30 mg) prepared in Reference Example 23 in dichloromethane (5 mL), N-bromosuccinimide (11 mg) was added at 0° C., and the mixture was stirred for 15 minutes. The reaction solution was diluted with dichloromethane, and was washed with water, and a saturated saline solution. The obtained organic layer was dried over anhydrous sodium sulfate, and was concentrated under a reduced pressure. The residue was purified by silica gel column chromatography to give the title compound (40 mg) having the following physical properties.

$^1$H-NMR (CDCl$_3$): δ3.07, 4.99, 6.52, 6.85, 6.87, 7.19-7.23, 7.27-7.38, 8.68.

Reference Example 25: 4-{[4-(Dibenzylamino)-7-(prop-1l-en-2-yl)pyrrolo[2,1-f][1,2,4]triazin-2-yl]amino}-3-fluoro-N,N-dimethylbenzamide To a solution of the compound (40 mg) prepared in Reference Example 24 in N,N-dimethylformamide (3 mL), 4,4,5,5-tetramethyl-2-(prop-1-en-2-yl)-1,3,2-dioxaborolane (24 mg), 2 M sodium bicarbonate aqueous solution (0.11 mL), and 1,1'-bis(diphenylphosphino)ferrocene-palladium (II) dichloride-dichloromethane complex (PdCl$_2$ (dppf).CH$_2$Cl$_2$ complex) (6 mg) were added. The reaction solution was deaerated, and thereafter, under a nitrogen atmosphere, the solution was stirred at 80° C. for 2 hours. The reaction solution was diluted with ethyl acetate, and was washed with water, and a saturated saline solution. The obtained organic layer was dried over anhydrous sodium sulfate, and was concentrated under a reduced pressure. The residue was purified by silica gel column chromatography to give the title compound (35 mg) having the following physical properties.

$^1$H-NMR (CDCl$_3$): δ2.22, 3.06, 5.01, 5.38, 6.21, 6.47, 6.50, 6.75, 7.12-7.21, 7.27-7.38, 8.41.

Reference Example 26: 4-{[4-Amino-7-(propan-2-yl)pyrrolo[2,1-f][1,2,4]triazin-2-yl]amino}-3-fluoro-N,N-dimethylbenzamide To a solution of the compound (35 mg) prepared in Reference Example 25 in ethanol (3 mL), palladium hydroxide on carbon (Pd(OH)$_2$/C) (3.5 mg, 10 wt %) was added, and under a hydrogen gas atmosphere, the mixture was stirred at 80° C. for 16 hours. The reaction solution was filtered through Celite, and thereafter, the filtrate was concentrated under a reduced pressure. The residue was purified by silica gel column chromatography to give the title compound (15 mg) having the following physical properties.

$^1$H-NMR (CDCl$_3$): δ1.34, 3.08, 3.46-3.53, 5.20, 6.38, 6.55, 6.80, 7.20-7.29, 8.61.

Reference Example 27: 4-{[4-Amino-5-bromo-7-(propan-2-yl)pyrrolo[2,1-f][1,2,4]triazin-2-yl]amino}-3-fluoro-N,N-dimethylbenzamide To a solution of the compound (100 mg) prepared in Reference Example 26 in tetrahydrofuran (30 mL), N-bromosuccinimide (50 mg) was added at −78° C., and the mixture was stirred for 15 minutes. The reaction solution was diluted with dichloromethane, and was washed with water, and a saturated saline solution. The obtained organic layer was dried over anhydrous sodium sulfate, and was concentrated under a reduced pressure. The residue was purified by silica gel column chromatography to give the title compound (130 mg) having the following physical properties.

$^1$H-NMR (CDCl$_3$): δ1.34, 3.08, 3.40-3.47, 6.19, 6.36, 6.96, 7.21-7.27, 8.48.

Reference Example 28: 4-({4-Amino-5-[3-(benzyloxy)phenyl]-7-(propan-2-yl)pyrrolo[2,1-f][1,2,4]triazin-2-yl}amino)-3-fluoro-N,N-dimethylbenzamide To a solution of the compound (130 mg) prepared in Reference Example 27 in 1,4-dioxane (15 mL), 3-benzyloxyphenylboronic acid (137 mg), 2 M tripotassium phosphatean aqueous solution (0.45 mL), and tetrakis(triphenylphosphine)palladium (Pd(PPh$_3$)$_4$) (69 mg) were added. The reaction solution was deaerated, and thereafter, under a nitrogen atmosphere, the solution was stirred at 100° C. for 16 hours. The reaction solution was diluted with ethyl acetate, and was washed with water, and a saturated saline solution. The obtained organic layer was dried over anhydrous sodium sulfate, and was concentrated under a reduced pressure. The residue was purified by silica gel column chromatography to give the title compound (33 mg) having the following physical properties.

$^1$H-NMR (CDCl$_3$): δ1.42, 3.09, 3.48-3.55, 5.13, 6.37, 6.78, 6.97-7.00, 7.07-7.09, 7.21-7.24, 7.28-7.29, 7.34-7.46, 8.61.

Example 25: 4-{[4-Amino-5-(3-hydroxyphenyl)-7-isopropylpyrrolo[2,1-f][1,2,4]triazin-2-yl]amino}-3-fluoro-N,N-dimethylbenzamide

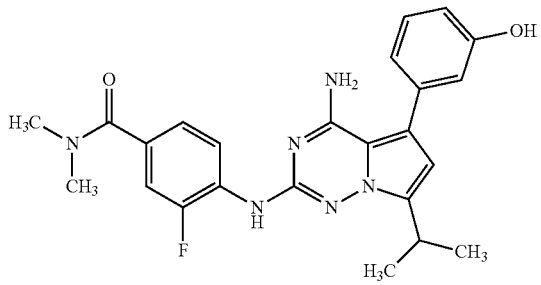 [SMILES: CC(C)c1cc(-c2cccc(O)c2)c2c(N)nc(Nc3ccc(C(=O)N(C)C)cc3F)nn12]

To a solution of the compound (33 mg) prepared in Reference Example 28 in ethanol (10 mL), palladium hydroxide on carbon (Pd(OH)$_2$/C) (6.6 mg, 20 wt %) was added, and under a hydrogen gas atmosphere, the mixture was stirred at room temperature for 2 hours. The reaction solution was filtered through Celite, and thereafter, the filtrate was concentrated under a reduced pressure. The residue was purified by reverse-phase column chromatography (C18, 10-90% acetonitrile/water, Isco Combiflash Companion MPLC system) to give the compound of the present invention (17 mg) having the following physical properties.

$^1$H-NMR (CDCl$_3$): δ1.41, 3.09, 3.47-3.54, 5.27, 5.95, 6.34, 6.73-6.88, 6.99-7.02, 7.19-7.25, 8.61.

Purity (LC-MS/ELSD): 100% (Retention time: 0.96 minutes);

MASS (ESI, Pos.): 449 (M+H)*.

Examples 26-1 to 26-3

A similar procedure to Reference Example 23→Reference Example 24→Reference Example 25→Reference Example 26→Reference Example 27→Reference Example 28→Example 2 was carried out by using 4-amino-3-fluoro-N,N-dimethylbenzamide or a corresponding amine compound instead of 4-amino-3-fluoro-N,N-dimethylbenzamide, and using 1-(tetrahydro-2H-pyran-2-yl)-4-(4,4,5,5-tetramethyl-1,3,2-dioxaborolan-2-yl)-1H-indazole instead of 4-benzyloxyphenylboronic acid to give the compound of the present invention having the following physical properties. Meanwhile, HPLC preparative purification was performed instead of silica gel column chromatography in Example 2.

Example 26-1: 4-{[4-Amino-5-(1H-indazol-4-yl)-7-isopropylpyrrolo[2,1-f][1,2,4]triazin-2-yl]amino}-3-fluoro-N,N-dimethylbenzamide trifluoroacetate

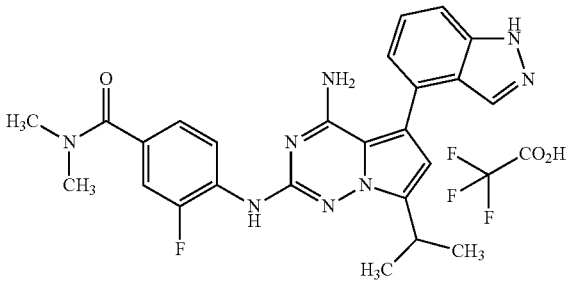

$^1$H-NMR (CDCl$_3$): δ1.35, 2.98, 3.36-3.45, 6.55, 7.13-7.55, 7.97, 8.07, 8.61, 13.21.
Purity (LC-MS/ELSD): 100% (Retention time: 0.94 minutes);
MASS (ESI, Pos.): 473 (M+H)$^+$.

Example 26-2: N$^2$-[2-fluoro-4-(methylsulfonyl)phenyl]-5-(1H-indazol-4-yl)-7-isopropylpyrrolo[2,1-f][1,2,4]triazine-2,4-diamine trifluoroacetate

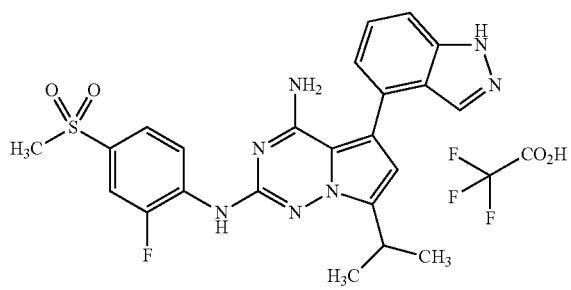

$^1$H-NMR (DMSO-d$_6$): δ1.38, 3.23, 3.41-3.51, 6.59, 7.23, 7.41-7.56, 7.71-7.77, 7.98, 8.46, 8.55.
Purity (LC-MS/ELSD): 100%/(Retention time: 0.97 minutes);
MASS (ESI, Pos.): 480 (M+H)$^+$.

Example 26-3: N$^2$-(1,3-dimethyl-1H-pyrazol-4-yl)-5-(1H-indazol-4-yl)-7-isopropylpyrrolo[2, 1-f][1,2,4]triazine-2,4-diamine trifluoroacetate $^1$H-NMR (DMSO-d$_6$): δ1.36, 2.15, 3.38-3.45, 3.75, 6.50, 7.10-7.12, 7.40-7.44, 7.52-7.54, 7.84-7.97, 7.98, 13.21.
Purity (LC-MS/ELSD): 99.8% (Retention time: 0.81 minutes);
MASS (ESI, Pos.): 402 (M+H)$^+$.

Pharmacological Experimental Examples

Pharmacological Experimental Example 1: Measurement of Brk Inhibitory Activity

Measurement of an inhibitory activity on Brk enzyme was performed by using LanthaScreen (registered trademark) system (Invitrogen) in accordance with the attached manual. Reagents used are described below.

Reaction Buffer: A solution containing 50 mmol/L HEPES (pH 7.5), 0.01% Brij 35, 10 mmol/L MgCl$_2$ and 1 mmol/L EGTA was prepared by using purified water.

A solution of a test substance (the compound of the present invention): A solution of each concentration of a test compound in DMSO was diluted 20-fold with Reaction Buffer, and a solution containing a test compound at a concentration 5 times a final concentration was prepared.

An enzyme solution: A solution containing 480 ng/mL of Brk enzyme was prepared by using Reaction Buffer.

A substrate solution: A solution containing 57 µmol/L of ATP and 500 nmol/L of Fluorescein-Poly GT (Invitrogen) was prepared by using Reaction Buffer.

A detection solution: A solution containing 20 mmol/L of EDTA and 4 nmol/L of PY20 (Invitrogen) was prepared by using Dilution B (Invitrogen).

To a 96-well plate (Nunc), a solution of 10 mmol/L of a test compound in DMSO was dispensed, and further, a dilution series at a common ratio of three was prepared by using DMSO. To each of wells of the 96-well plate for the measurement, 5 µL of Reaction Buffer containing DMSO was added for a blank group and a vehicle group and 5 µL of a test substance solution was added for a test substance group. Next, 10 µL per well of Reaction Buffer was added for the blank group, and 10 µL per well of the enzyme solution was added for the vehicle group and the test compound group, and thereafter, the mixture was stirred at room temperature for 10 minutes. After completion of stirring, 10 µL of the substrate solution was added to each of wells, and the mixture was stirred at room temperature under a shading condition for 1 hour. After completion of the reaction, 25 µL of the detection solution was added to each well, and the mixture was left to stand at room temperature under a shading condition for 30 minutes. After being left standing, fluorescence intensities at 520 nm and 495 nm were measured by using Analyst GT (Molecular Devices, LLC) when being irradiated with an excitation light at 340 nm. The phosphorylation of the artificial substrate was quantified by Tune-Resolved Fluorescence Resonance Energy Transfer (TR-FRET). With regard to each well, the TR-FRET ratio was calculated by divining the fluorescence signal at 520 nm by the fluorescence signal at 495 nm, and the inhibition rate (%) in the test compound group was calculated according to the following Numerical Formula 1.

Inhibition rate (%)={1−(TR-FRET ratio of test compound group−A)(B−A)}×100    [Numerical Formula 1]

A: Mean value of TR-FRET ratio of blank group
B: Mean value of TR-FRET ratio of vehicle group The value (IC$_{50}$ value) of 50% inhibition rate of the test compound was calculated from the inhibition curve based on the inhibition rate at each concentration of the test compound.

As a result, it was found that each IC$_{50}$ value of the compounds of the present invention was equal to or lower than 0.1 µmol/L, and the compound of the present invention has a potent Brk inhibitory activity. For example, IC$_{50}$ values of several compounds of the present invention were as shown in the following Table 1.

TABLE 1

| Example No. | Brk inhibitory activity (IC$_{50}$, nM) |
| --- | --- |
| 1 | 2.1 |
| 2 | 5.4 |
| 4-1 | 5.1 |
| 4-2 | 9.3 |
| 4-3 | 8.5 |
| 8 | 7.6 |
| 10 | 6.9 |
| 12 | 5.1 |
| 13-1 | 3.3 |
| 13-9 | 4.1 |
| 14-4 | 12 |
| 14-11 | 50 |
| 18-1 | 7.7 |
| 23 | 9.7 |
| 25 | 3.4 |
| 26-1 | 3.7 |

Pharmacological Experimental Example 2: Tests of Enzyme Inhibitory Activities on Kinases Other than Brk (Experiment on Selectivity)

2-1: Lck Inhibitory Activity

Tyrosine phosphorylation of Lck was performed by using Z'-LYTE Kinase Assay Kit-Tyr 2 Peptide (Invitrogen) containing the following reagents (Tyr 2 Peptide, Tyr 2 Phospho-Peptide, 5× Kinase Buffer, ATP, Coloring Reagent A, Coloring Buffer, and Stop Reagent) and Lck. The Lck activity was determined by using Fluorescence Resonance Energy Transfer (FRET) method.

A dilute solution (5 μL) of the compound of the present invention in dimethylsulfoxide (DMSO; Sigma-Aldrich Co. LLC) was added to a 96-well assay plate. In addition, Peptide/Kinase Buffer composed of DL-dithiothreitol (DTT; 2 mM), Tyr 2 Peptide (2 μM), Kinase Buffer and Lck was added to the assay plate, and the reaction solution was preincubated at 25° C. for 20 minutes. Then, ATP solution (5 μL) composed of adenosine triphosphate (ATP; 45 μM) and Kinase Buffer was added, and the reaction solution was incubated at 25° C. for 1 hour. After incubation, Coloring Solution A (10 μL) composed of Coloring Reagent B and Coloring Buffer was added, and the reaction solution was incubated at 25° C. for 1 hour. Stop Reagent (10 μL) was added to each well such that the enzymatic reaction stopped. The fluorescent coloring of each well was measured on a fluorescent plate reader by using wavelengths of 445 nm and 520 nm. The ratio of phosphorylation was determined by a ratio of coloring at 445 nm to that at 520 nm according to the attached manual.

The inhibition rate (%) of the compound of the present invention was calculated according to the following Numerical Formula 2.

Inhibition rate (%)={1−(AX−AB)/(AC−AB)}×100   [Numerical Formula 2]

AX: Ratio of phosphorylation at addition of the compound of the present invention
AB: Ratio of phosphorylation in blank
AC: Ratio of phosphorylation at addition of only DMSO The value of 50% inhibition rate ($IC_{50}$) of the compound of the present invention was determined from the inhibition curve based on the inhibition rate at each concentration of the compound of the present invention.

2-2: Syk Inhibitory Activity

The compound of the present invention was dissolved in DMSO to prepare a solution with a concentration of 100 times the test concentration of 1 μmol/L. The solution was further diluted 25-fold with Assay Buffer (20 mmol/L HEPES, 0.01% Triton X-100, 2 mmol/L DTT, pH 7.5) to give a test substance solution. With regard to a positive control substance (Staurosporine), a solution of the positive control substance was prepared in a similar manner.

Five microliters of a test substance solution with a concentration of four times prepared by using Assay Buffer, 5 μL of a solution of a substrate (Blk/Lyntide)/ATP/a metal (Mg) with a concentration of four times and 10 μL of a solution of Syk kinase with a concentration of two times were mixed in a well of a 384-well plate made of polypropylene, and the mixture was subjected to a reaction at room temperature for 1 hour (the final concentration of the substrate was 1,000 nmol/L, and the final concentration of ATP was 26 μmol/L). To the mixture, 60 μL of Termination Buffer (QuickScout Screening Assist MSA; Carna Biosciences, Inc.) was added to stop the reaction. The substrate peptide and the phosphorylated peptide in the reaction solution were separated, and were quantified. The kinase reaction was evaluated by a product ratio (P/(P+S)) calculated from a peak height (S) of the substrate peptide and a peak height (P) of the phosphorylated peptide.

The inhibition rates of the compounds of the present invention on Lck and Syk kinases in Pharmacological Example 2, for example, in the cases of the compounds of the present invention of Example 1, Example 4-3, and Example 13-1, were as shown in the following Table 2.

TABLE 2

| Example No. | Lck inhibitory activity ($IC_{50}$, μM) | Syk inhibitory activity (Inhibition rate at 1 μM of compound) |
|---|---|---|
| 1 | >10 | 0% |
| 4-3 | 2.5 | 0% |
| 13-1 | >10 | 0% |

From the result, with regard to a selective inhibitory activity on Brk to Lck, in the case of the compound of Example 1, the selective inhibitory activity on Brk to Lck was 4,762-fold, in the case of the compound of Example 4-3, the selective inhibitory activity on Brk to Lck was 294-fold, and in the case of the compound of Example 13-1, the selective inhibitory activity on Brk to Lck was 3,030-fold. In addition, on Syk, each of three compounds had no inhibitory activity at 1 μM. Accordingly, it was found that the compound of the present invention has a potent Brk inhibitory activity and is excellent in Brk selectivity.

Preparation Examples

Preparation Example 1

The following ingredients can be mixed in a conventional manner and compressed to give 10,000 tablets each containing 10 mg of the active ingredient.
$N^6$-(1,3-dimethyl-1H-pyrazol-4-yl)-3-(1H-indol-5-yl)-1-isopropyl-1H-pyrazolo[3,4-d]pyrimidine-4,6-diamine . . . 100 g
Carboxymethyl cellulose calcium (a disintegrating agent) . . . 20 g
Magnesium stearate (a lubricant) . . . 10 g
Microcrystalline cellulose . . . 870 g

INDUSTRIAL APPLICABILITY

The compound of the present invention has a Brk inhibitory activity, and is effective for the prevention and/or treatment of diseases in which Brk involves, for example, cancer and the like.

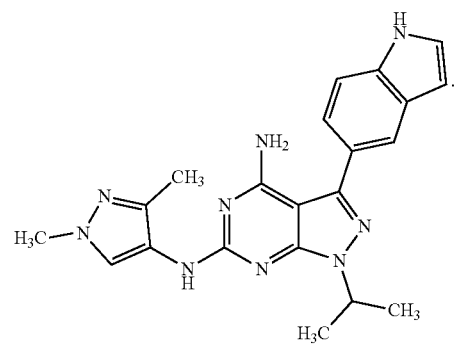 [SMILES: Cc1nn(C)cc1Nc1nc(N)c2c(-c3ccc4[nH]ccc4c3)nn(C(C)C)c2n1]

3. A salt of a compound represented by structural formula as below,
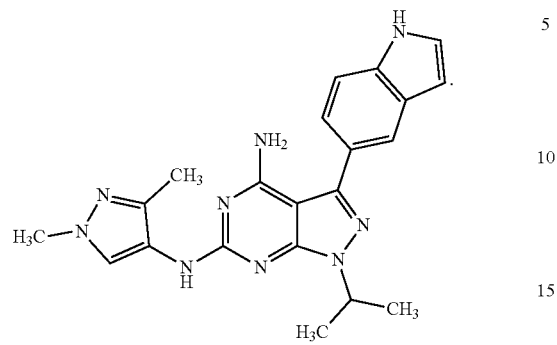

The invention claimed is:

1. $N^6$-(1,3-dimethyl-1H-pyrazol-4-yl)-3-(1H-indol-5-yl)-1-isopropyl-1H-pyrazolo[3,4-d]pyrimidine-4,6-diamine;
   a salt thereof, a solvate thereof, or an N-oxide thereof.

2. A compound represented by structural formula as below,